(12) United States Patent
Ellis et al.

(10) Patent No.: US 8,969,039 B2
(45) Date of Patent: *Mar. 3, 2015

(54) BACTERIAL HOST STRAIN COMPRISING A MUTANT SPR GENE AND HAVING REDUCED TSP ACTIVITY

(75) Inventors: Mark Ellis, Slough (GB); David Paul Humphreys, Slough (GB)

(73) Assignee: UCB Pharma S.A., Brussels (BE)

(*) Notice: Subject to any disclaimer, the term of this patent is extended or adjusted under 35 U.S.C. 154(b) by 29 days.

This patent is subject to a terminal disclaimer.

(21) Appl. No.: 13/522,087

(22) PCT Filed: Jan. 13, 2011

(86) PCT No.: PCT/EP2011/050413
§ 371 (c)(1),
(2), (4) Date: Jul. 25, 2012

(87) PCT Pub. No.: WO2011/086136
PCT Pub. Date: Jul. 21, 2011

(65) Prior Publication Data
US 2012/0295309 A1 Nov. 22, 2012

(30) Foreign Application Priority Data
Jan. 14, 2010 (GB) .................................. 1000587.4

(51) Int. Cl.
*C12N 15/70* (2006.01)
*C12N 15/09* (2006.01)
*C07K 14/245* (2006.01)
*C12N 9/52* (2006.01)

(52) U.S. Cl.
CPC .............. *C12N 15/70* (2013.01); *C07K 14/245* (2013.01); *C12N 9/52* (2013.01)
USPC ........................ 435/69.1; 435/252.3; 435/183

(58) Field of Classification Search
CPC ................................. C12N 15/70; C12N 15/09
USPC ..................................... 435/69.1, 252.3, 183
See application file for complete search history.

(56) References Cited

U.S. PATENT DOCUMENTS

| 5,264,365 | A | 11/1993 | Georgiou et al. |
| 6,306,619 | B1 | 10/2001 | Jones et al. |
| 7,662,587 | B1 | 2/2010 | Cheng et al. |
| 2006/0204493 | A1 | 9/2006 | Huang et al. |
| 2012/0258492 | A1 | 10/2012 | Ellis et al. |
| 2012/0288894 | A1 | 11/2012 | Ellis et al. |
| 2012/0301920 | A1 | 11/2012 | Ellis et al. |

FOREIGN PATENT DOCUMENTS

| WO | WO 02/48376 | 6/2002 |
| WO | WO 02/061090 | 8/2002 |
| WO | WO 2011/036454 | 3/2011 |
| WO | WO 2011/086138 | 7/2011 |
| WO | WO 2011/086139 | 7/2011 |

OTHER PUBLICATIONS

Database UniProt [Online] EBI Accession No. UNIPROT:B7UFJ2, Subname: Full=Predicted peptidase, outer membrane lipoprotein, Feb. 10, 2009, XP-002630316, p. 1.
Database UniProt [Online] EBI Accession No. UNIPROT:B7LAJ9, Subname: Full=Putative peptidase, outer membrane lipoprotein, Feb. 10, 2009, XP-002630317, p. 1.
Database UniProt [Online] EBI Accession No. UNIPROT:B7LJR7, Subname: Full=Putative peptidase, outer membrane lipoprotein, Feb. 10, 2009, XP-002630318, p. 1.
Database UniProt [Online] EBI Accession No. UNIPROT:C1M6L5, Subname: Full=Putative uncharacterized protein, May 26, 2009, XP-002630319, p. 1.
Aramini, J. et al. "Solution NMR Structure of the NlpC/P60 Domain of Lipoprotein Spr from *Escherichia coli*: Structural Evidence for a Novel Cysteine Peptidase Catalytic Triad" *Biochemistry*, 2008, pp. 9715-9717, vol. 47.
Tadokoro, A. et al. "Interaction of the *Escherichia coli* Lipoprotein Nlpl with Periplasmic Prc (Tsp) Protease" *Journal of Biochemistry*, 2004, pp. 185-191, vol. 135.
Written Opinion in International Application No. PCT/EP2011/050415, Jun. 20, 2011, pp. 1-15.
Baneyx, F. et al. "Construction and Characterization of *Escherichia coli* Strains Deficient in Multiple Secreted Proteases: Protease III Degrades High-Molecular-Weight Substrates In Vivo" *Journal of Bacteriology*, Apr. 1991, pp. 2696-2703, vol. 173, No. 8.
Spiess, C. et al. "A Temperature-Dependent Switch from Chaperone to Protease in a Widely Conserved Heat Shock Protein" *Cell*, Apr. 30, 1999, p. 339-347, vol. 97.
Skorko-Glonek, J. et al. "The proteolytic activity of the HtrA (DegP) protein from *Escherichia coli* at low temperatures" *Microbiology*, 2008, pp. 3649-3658, vol. 154.
Meerman, H. J. et al. "Construction and Characterization of a Set of *E. coli* Strains Deficient in All Known Loci Affecting the Proteolytic Stability of Secreted Recombinant Proteins" *Bio/Technology*, Nov. 1994, pp. 1107-1110, vol. 12.
Written Opinion in International Application No. PCT/GB2010/001790, Feb. 3, 2011, pp. 1-9.
O'Dwyer, R. et al. "Microarray-based analysis of recombinant protein production in *E. coli*" *Microbial Cell Factories*, 2006, pp. 1-2 vol. 5, Supp 1.

(Continued)

*Primary Examiner* — Karen Cochrane Carlson
(74) *Attorney, Agent, or Firm* — Saliwanchik, Lloyd & Eisenschenk

(57) ABSTRACT

The present invention provides a recombinant gram-negative bacterial cell comprising a mutant spr gene encoding a spr protein having a mutation at one or more amino acids selected from D133, H145, H157, N31, R62, I70, Q73, C94, S95, V98, Q99, R100, L108, Y115, V135, L136, G140, R144 and G147 and wherein the cell has reduced Tsp protein activity compared to a wild-type cell.

27 Claims, 12 Drawing Sheets

(56) References Cited

OTHER PUBLICATIONS

Hu, X. et al. "Optimisation of production of a domoic acid-binding scFv antibody fragment in *Escherichia coli* using molecular chaperones and functional immobilisation on a mesoporous silicate support" *Protein Expression and Purification*, 2007, pp. 194-201, vol. 52.

Maskos, K. et al. "DsbA and DsbC-catalyzed Oxidative Folding of Proteins with Complex Disulfide Bridge Patterns In Vitro and In Vivo" *Journal of Molecular Biology*, 2003, pp. 495-513, vol. 325.

Written Opinion in International Application No. PCT/EP2011/050416, Apr. 26, 2011, pp. 1-7.

Baba, T. et al. "Construction of *Escherichia coli* K-12 in-frame, single-gene knockout mutants: the Keio collection" *Molecular Systems Biology*, 2006, pp. 1-11.

Silber, K. R. et al. "Deletion of the *prc* (*tsp*) gene provides evidence for additional tail-specific proteolytic activity in *Escherichia coli* K-12" *Mol. Gen Genet*, 1994, vol. 242, pp. 237-240.

Chen, C. et al. "High-Level Accumulation of a Recombinant Antibody Fragment in the Periplasm of *Escherichia coli* Requires a Triple-Mutant (*degP prc spr*) Host Strain" *Biotechnology and Bioengineering*, Mar. 5, 2004, pp. 463-474, vol. 85, No. 5.

Hara, H. et al. "Overproduction of Penicillin-Binding Protein 7 Suppresses Thermosensitive Growth Defect at Low Osmolarity due to an *spr* Mutation of *Escherichia coli*" *Microbial Drug Resistance*, Nov. 1, 1996, pp. 63-72, vol. 2, No. 1.

Written Opinion in International Application No. PCT/EP2011/050413, Apr. 8, 2011, pp. 1-7.

Figure 11a

Wild type ptr (protease III) 5'.

```
     *   M   P   R   S   T   W   F   K   A   L   L   L   V
    TGA ATG CCC CGC AGC ACC TGG TTC AAA GCA TTA TTG TTG TTA GTT

A   L   W   A   P   L   S
    GCC CTT TGG GCA CCC TTA AGT
```

Mutated Δ ptr (protease III) 5'.

```
        EcoR I
        ~~~~~~~~
     *   I   P   R   S   T   W   F   K   A   L   L   L   V
    TGA ATT CCC CGC AGC ACC TGG TTC AAA GCA TTA TTG TTG TTA GTT

Ase I
                          ~~~~~~~~
     A   L   W   A   H   *   C
    GCC CTT TGG GCA CAT TAA TGT
```

Figure 11b

Wild type Tsp 5'.

```
     M   N   M   F   F   R   L   T   A   L   A   G   L   L   A
    ATG AAC ATG TTT TTT AGG CTT ACC GCG TTA GCT GGC CTG CTT GCA

I   A   G   Q   T   F   A
    ATA GCA GGC CAG ACC TTC GCT
```

Mutated Δ Tsp 5'.

```
        EcoR I
        ~~~~~~~~
     M   N   S   F   L   G   L   P   R   *   L   A   C   L   Q
    ATG AAT TCG TTT TTA GGC TTA CCG CGT TAG CTG GCC TGC TTG CAA

Ase I
                         ~~~~~~~~
     *   Q   A   R   H   *   L
    TAG CAG GCC AGA CAT TAA TTG
```

Figure 11c

Wild type DegP

```
202    D   A   A   I   N   R   G   N   S   G   G
949    GAT GCA GCG ATC AAC CGT GGT AAC TCC GGT GGT
```

Mutated DegP S210A

```
                           Ase I
                       ~~~~~~~~
202    D   A   A   I   N   R   G   N   A   G   G
949    GAT GCA GCG ATT AAT CGT GGT AAC GCC GGT GGT
```

```
                              SEQUENCE LISTING

<160> NUMBER OF SEQ ID NOS: 37

<210> SEQ ID NO 1
<211> LENGTH: 2049
<212> TYPE: DNA
<213> ORGANISM: E. coli

<400> SEQUENCE: 1
atgaacatgt tttttaggct taccgcgtta gctggcctgc ttgcaatagc aggccagacc        60
ttcgctgtag aagatatcac gcgtgctgat caaattccgg tattaaagga agagacgcag       120
catgcgacgg taagtgagcg cgtaacgtcg cgcttcaccc gttctcatta tcgccagttc       180
gacctcgatc aggcattttc ggccaaaatc tttgaccgct acctgaatct gctcgattac       240
agccacaacg tgctgctggc aagcgatgtt gaacagttcg cgaaaaagaa aaccgagtta       300
ggcgatgaac tgcgttcagg caaactcgac gttttctacg atctctacaa tctggcgcaa       360
aagcgccgtt ttgagcgtta ccagtacgct ttgtcggtac tggaaaagcc gatggatttc       420
accggcaacg acacttataa ccttgaccgc agcaaagcgc cctggccgaa aaacgaggct       480
gagttgaacg cgctgtggga cagtaaagtc aaattcgacg agttaagcct gaagctgaca       540
ggaaaaacgg ataaagaaat tcgtgaaacc ctgactcgcc gctacaaatt tgccattcgt       600
cgtctggcgc aaaccaacag cgaagatgtt ttctcgctgg caatgacggc gtttgcgcgt       660
gaaatcgacc cgcataccaa ctatctttcc ccgcgtaata ccgaacagtt caacactgaa       720
atgagtttgt cgctggaagg tattggcgca gtgctgcaaa tggatgatga ctacaccgtt       780
atcaattcga tggtggcagg tggtccggca gcgaagagta aagctatcag cgttggtgac       840
aaaattgtcg gtgttggtca aacaggcaag ccgatggttg acgtgattgg ctggcgtctt       900
gatgatgtgg ttgccttaat taaagggccg aagggcagta agttcgtctc ggaaatttta       960
cctgctggta aagggaccaa gacccgtact gtaacgttga cccgtgaacg tattcgtctc      1020
gaagaccgcg cggttaaaat gtcggtgaag accgtcggta aagagaaagt cggcgtgctg      1080
gatattccgg gcttctatgt gggtttgaca gacgatgtca aagtgcaact gcagaaactg      1140
gaaaaacaga atgtcagcag cgtcatcatc gacctgcgta gcaatggcgg tggggcgtta      1200
actgaagccg tatcgctctc cggtctgttt attcctgcgg gtcccattgt tcaggtccgc      1260
gataacaacg gcaaggttcg tgaagatagc gataccgacg gacaggtttt ctataaaggc      1320
ccgctggtgg tgctggttga ccgcttcagt gcttcggctt cagaaatctt tgccgcggca      1380
```

-continued

```
atgcaggatt acggtcgtgc gctggttgtg ggtgaaccga cgtttggtaa aggcaccgtt    1440
cagcaatacc gttcattgaa ccgtatttac gatcagatgt tacgtcctga atggccagcg    1500
ctgggttctg tgcagtacac gatccagaaa ttctatcgcg ttaacggcgg cagtacgcaa    1560
cgtaaaggcg taacgccaga catcatcatg ccgacgggta atgaagaaac ggaaacgggt    1620
gagaaattcg aagataacgc gctgccgtgg gatagcattg atgccgcgac ttatgtgaaa    1680
tcaggagatt taacggcctt tgaaccggag ctgctgaagg aacataatgc gcgtatcgcg    1740
aaagatcctg agttccagaa catcatgaag gatatcgcgc gcttcaacgc tatgaaggac    1800
aagcgcaata tcgtttctct gaattacgct gtgcgtgaga agagaataa tgaagatgat    1860 gcgacgcgtc tggcgcgttt gaacgaacgc tttaaacgcg aaggtaaacc ggagttgaag    1920
aaactggatg atctaccgaa agattaccag gagccggatc cttatctgga tgagacggtg    1980
aatatcgcac tcgatctggc gaagcttgaa aaagccagac ccgcggaaca acccgctccc    2040
gtcaagtaa                                                            2049
```

<210> SEQ ID NO 2
<211> LENGTH: 682
<212> TYPE: PRT
<213> ORGANISM: E. coli

<400> SEQUENCE: 2

```
Met Asn Met Phe Phe Arg Leu Thr Ala Leu Ala Gly Leu Leu Ala Ile
1               5                   10                  15

Ala Gly Gln Thr Phe Ala Val Glu Asp Ile Thr Arg Ala Asp Gln Ile
            20                  25                  30

Pro Val Leu Lys Glu Thr Gln His Ala Thr Val Ser Glu Arg Val
        35                  40                  45

Thr Ser Arg Phe Thr Arg Ser His Tyr Arg Gln Phe Asp Leu Asp Gln
    50                  55                  60

Ala Phe Ser Ala Lys Ile Phe Asp Arg Tyr Leu Asn Leu Leu Asp Tyr
65                  70                  75                  80

Ser His Asn Val Leu Leu Ala Ser Asp Val Glu Gln Phe Ala Lys Lys
                85                  90                  95

Lys Thr Glu Leu Gly Asp Glu Leu Arg Ser Gly Lys Leu Asp Val Phe
            100                 105                 110

Tyr Asp Leu Tyr Asn Leu Ala Gln Lys Arg Arg Phe Glu Arg Tyr Gln
        115                 120                 125

Tyr Ala Leu Ser Val Leu Glu Lys Pro Met Asp Phe Thr Gly Asn Asp
    130                 135                 140

Thr Tyr Asn Leu Asp Arg Ser Lys Ala Pro Trp Pro Lys Asn Glu Ala
145                 150                 155                 160

Glu Leu Asn Ala Leu Trp Asp Ser Lys Val Lys Phe Asp Glu Leu Ser
                165                 170                 175

Leu Lys Leu Thr Gly Lys Thr Asp Lys Glu Ile Arg Glu Thr Leu Thr
            180                 185                 190

Arg Arg Tyr Lys Phe Ala Ile Arg Arg Leu Ala Gln Thr Asn Ser Glu
        195                 200                 205

Asp Val Phe Ser Leu Ala Met Thr Ala Phe Ala Arg Glu Ile Asp Pro
    210                 215                 220

His Thr Asn Tyr Leu Ser Pro Arg Asn Thr Glu Gln Phe Asn Thr Glu
225                 230                 235                 240
```

```
Met Ser Leu Ser Leu Glu Gly Ile Gly Ala Val Leu Gln Met Asp
            245                 250                 255
Asp Tyr Thr Val Ile Asn Ser Met Val Ala Gly Gly Pro Ala Lys
            260                 265                 270
Ser Lys Ala Ile Ser Val Gly Asp Lys Ile Val Gly Val Gly Gln Thr
            275                 280                 285
Gly Lys Pro Met Val Asp Val Ile Gly Trp Arg Leu Asp Asp Val Val
            290                 295                 300
Ala Leu Ile Lys Gly Pro Lys Gly Ser Lys Val Arg Leu Glu Ile Leu
305                 310                 315                 320
Pro Ala Gly Lys Gly Thr Lys Thr Arg Thr Val Thr Leu Thr Arg Glu
                    325                 330                 335
Arg Ile Arg Leu Glu Asp Arg Ala Val Lys Met Ser Val Lys Thr Val
                    340                 345                 350
Gly Lys Glu Lys Val Gly Val Leu Asp Ile Pro Gly Phe Tyr Val Gly
            355                 360                 365
Leu Thr Asp Asp Val Lys Val Gln Leu Gln Lys Leu Glu Lys Gln Asn
            370                 375                 380
Val Ser Ser Val Ile Ile Asp Leu Arg Ser Asn Gly Gly Gly Ala Leu
385                 390                 395                 400
Thr Glu Ala Val Ser Leu Ser Gly Leu Phe Ile Pro Ala Gly Pro Ile
                    405                 410                 415
Val Gln Val Arg Asp Asn Asn Gly Lys Val Arg Glu Asp Ser Asp Thr
                    420                 425                 430
Asp Gly Gln Val Phe Tyr Lys Gly Pro Leu Val Val Leu Val Asp Arg
            435                 440                 445
Phe Ser Ala Ser Ala Ser Glu Ile Phe Ala Ala Ala Met Gln Asp Tyr
450                 455                 460
Gly Arg Ala Leu Val Val Gly Glu Pro Thr Phe Gly Lys Gly Thr Val
465                 470                 475                 480
Gln Gln Tyr Arg Ser Leu Asn Arg Ile Tyr Asp Gln Met Leu Arg Pro
                    485                 490                 495
Glu Trp Pro Ala Leu Gly Ser Val Gln Tyr Thr Ile Gln Lys Phe Tyr
            500                 505                 510
Arg Val Asn Gly Gly Ser Thr Gln Arg Lys Gly Val Thr Pro Asp Ile
            515                 520                 525
Ile Met Pro Thr Gly Asn Glu Val Thr Glu Thr Gly Glu Lys Phe Glu
530                 535                 540
Asp Asn Ala Leu Pro Trp Asp Ser Ile Asp Ala Ala Thr Tyr Val Lys
545                 550                 555                 560
Ser Gly Asp Leu Thr Ala Phe Glu Pro Glu Leu Leu Lys Glu His Asn
                    565                 570                 575
Ala Arg Ile Ala Lys Asp Pro Glu Phe Gln Asn Ile Met Lys Asp Ile
                    580                 585                 590
Ala Arg Phe Asn Ala Met Lys Asp Lys Arg Asn Ile Val Ser Leu Asn
            595                 600                 605
Tyr Ala Val Arg Glu Lys Glu Asn Asn Glu Asp Ala Thr Arg Leu
            610                 615                 620
Ala Arg Leu Asn Glu Arg Phe Lys Arg Glu Gly Lys Pro Glu Leu Lys
625                 630                 635                 640
Lys Leu Asp Asp Leu Pro Lys Asp Tyr Gln Glu Pro Asp Pro Tyr Leu
                    645                 650                 655
```

Asp Glu Thr Val Asn Ile Ala Leu Asp Leu Ala Lys Leu Glu Lys Ala
            660                 665                 670

Arg Pro Ala Glu Gln Pro Ala Pro Val Lys
            675                 680

<210> SEQ ID NO 3
<211> LENGTH: 2048
<212> TYPE: DNA
<213> ORGANISM: E. coli

<400> SEQUENCE: 3

| | | | | | |
|---|---|---|---|---|---|
| atgaattcgt | ttttaggctt | accgcgttag | ctggcctgct | tgcaatagca | ggccagacat | 60 |
| taattgtaga | agatatcacg | cgtgctgatc | aaattccggt | attaaaggaa | gagacgcagc | 120 |
| atgcgacggt | aagtgagcgc | gtaacgtcgc | gcttcacccg | ttctcattat | cgccagttcg | 180 |
| acctcgatca | ggcattttcg | gccaaaatct | ttgaccgcta | cctgaatctg | ctcgattaca | 240 |
| gccacaacgt | gctgctggca | agcgatgttg | aacagttcgc | gaaaaagaaa | accgagttag | 300 |
| gcgatgaact | gcgttcaggc | aaactcgacg | ttttctacga | tctctacaat | ctggcgcaaa | 360 |
| agcgccgttt | tgagcgttac | cagtacgctt | tgtcggtact | ggaaaagccg | atggatttca | 420 |
| ccggcaacga | cacttataac | cttgaccgca | gcaaagcgcc | ctggccgaaa | aacgaggctg | 480 |
| agttgaacgc | gctgtgggac | agtaaagtca | aattcgacga | gttaagcctg | aagctgacag | 540 |
| gaaaaacgga | taaagaaatt | cgtgaaaccc | tgactcgccg | ctacaaattt | gccattcgtc | 600 |
| gtctggcgca | aaccaacagc | gaagatgttt | tctcgctggc | aatgacggcg | tttgcgcgtg | 660 |
| aaatcgaccc | gcataccaac | tatctttccc | cgcgtaatac | cgaacagttc | aacactgaaa | 720 |
| tgagtttgtc | gctggaaggt | attggcgcag | tgctgcaaat | ggatgatgac | tacaccgtta | 780 |
| tcaattcgat | ggtggcaggt | ggtccggcag | cgaagagtaa | agctatcagc | gttggtgaca | 840 |
| aaattgtcgg | tgttggtcaa | acaggcaagc | cgatggttga | cgtgattggc | tggcgtcttg | 900 |
| atgatgtggt | tgccttaatt | aaagggccga | agggcagtaa | agttcgtctg | gaaattttac | 960 |
| ctgctggtaa | agggaccaag | accgtactg | taacgttgac | ccgtgaacgt | attcgtctcg | 1020 |
| aagaccgcgc | ggttaaaatg | tcggtgaaga | ccgtcggtaa | agagaaagtc | ggcgtgctgg | 1080 |
| atattccggg | cttctatgtg | ggtttgacag | acgatgtcaa | agtgcaactg | cagaaactgg | 1140 |
| aaaaacagaa | tgtcagcagc | gtcatcatcg | acctgcgtag | caatggcggt | ggggcgttaa | 1200 |
| ctgaagccgt | atcgctctcc | ggtctgtttta | ttcctgcggg | tcccattgtt | caggtccgcg | 1260 |
| ataacaacgg | caaggttcgt | gaagatagcg | ataccgacgg | acaggttttc | tataaaggcc | 1320 |
| cgctggtggt | gctggttgac | cgcttcagtg | cttcggcttc | agaaatcttt | gccgcggcaa | 1380 |
| tgcaggatta | cggtcgtgcg | ctggttgtgg | gtgaaccgac | gtttggtaaa | ggcaccgttc | 1440 |
| agcaataccg | ttcattgaac | cgtatttacg | atcagatgtt | acgtcctgaa | tggccagcgc | 1500 |
| tgggttctgt | gcagtacacg | atccagaaat | ctatcgcgt | taacggcggc | agtacgcaac | 1560 |
| gtaaaggcgt | aacgccagac | atcatcatgc | cgacgggtaa | tgaagaaacg | gaaacgggtg | 1620 |
| agaaattcga | agataacgcg | ctgccgtggg | atagcattga | tgccgcgact | tatgtgaaat | 1680 |
| caggagattt | aacggccttt | gaaccggagc | tgctgaagga | acataatgcg | cgtatcgcga | 1740 |
| agatcctga | gttccagaac | atcatgaagg | atatcgcgcg | cttcaacgct | atgaaggaca | 1800 |
| agcgcaatat | cgtttctctg | aattacgctg | tgcgtgagaa | agagaataat | gaagatgatg | 1860 |
| cgacgcgtct | ggcgcgtttg | aacgaacgct | ttaaacgcga | aggtaaaccg | agttgaagaa | 1920 |
| aactggatga | tctaccgaaa | gattaccagg | agccggatcc | ttatctggat | gagacggtga | 1980 |

| | |
|---|---:|
| atatcgcact cgatctggcg aagcttgaaa aagccagacc cgcggaacaa cccgctcccg | 2040 |
| tcaagtaa | 2048 |

<210> SEQ ID NO 4
<211> LENGTH: 2889
<212> TYPE: DNA
<213> ORGANISM: E. coli

<400> SEQUENCE: 4

| | |
|---|---:|
| atgccccgca gcacctggtt caaagcatta ttgttgttag ttgccctttg ggcacccttg | 60 |
| agtcaggcag aaacgggatg gcagccgatt caggaaacca tccgtaaaag tgataaagat | 120 |
| aaccgccagt atcaggctat acgtctggat aacggtatgg tggtcttgct ggtttctgat | 180 |
| ccgcaggcag ttaaatcgct ctcggcgctg gtggtgcccg ttgggtcgct ggaagatccc | 240 |
| gaggcgtacc aggggctggc acattacctt gaacatatga gtctgatggg gtcgaaaaag | 300 |
| tacccgcagg ctgacagtct ggccgaatat ctcaaaatgc acggcggtag tcacaatgcc | 360 |
| agcactgcgc cgtatcgcac ggcttttctat ctggaagttg agaacgacgc cttgcctggt | 420 |
| gcggtagacc gcctggccga tgctattgct gaaccttttgc tcgacaagaa atatgccgaa | 480 |
| cgtgagcgta atgcggtgaa cgctgaatta accatggcgc gtacgcgtga cgggatgcgc | 540 |
| atggcacagg tcagcgcaga aaccattaac ccggcacacc ccggttcaaa gttttctggt | 600 |
| ggtaacctcg aaactttaag cgacaaacct ggtaatccgg tgcagcaggc gctgaaagat | 660 |
| ttccacgaga agtactattc cgccaatttg atgaaggcgg ttatttacag taataaaccg | 720 |
| ctgccggagt tggcaaaaat ggcggcggac acctttggtc gcgtgccgaa caaagagagc | 780 |
| aaaaaaccgg aaatcaccgt gccggtagtc accgacgcgc aaaagggcat tatcattcat | 840 |
| tacgtccctg cgctgccgcg taaagtgttg cgcgttgagt ttcgcatcga taacaactca | 900 |
| gcgaagttcc gtagtaaaac cgatgaattg attacctatc tgattggcaa tcgcagccca | 960 |
| ggtacacttt ctgactggct gcaaaagcag ggattagttg agggcattag cgccaactcc | 1020 |
| gatcctatcg tcaacggcaa cagcggcgta ttagcgatct ctgcgtcttt aaccgataaa | 1080 |
| ggcctggcta atcgcgatca ggttgtggcg gcaatttta gctatctcaa tctgttacgt | 1140 |
| gaaaaaggca ttgataaaca atacttcgat gaactggcga atgtgctgga tatcgacttc | 1200 |
| cgttatccgt cgatcacccg tgatatggat tacgtcgaat ggctggcaga taccatgatt | 1260 |
| cgcgttcctg ttgagcatac gctggatgca gtcaatattg ccgatcggta cgatgctaaa | 1320 |
| gcagtaaagg aacgtctggc gatgatgacg ccgcagaatg cgcgtatctg gtatatcagc | 1380 |
| ccgaaagagc gcacaacaa acggcttac tttgtcgatg cgccgtatca ggtcgataaa | 1440 |
| atcagcgcac aaactttcgc cgactggcag aaaaagccg ccgacattgc gctctctttg | 1500 |
| ccagagctta acccttatat tcctgatgat ttctcgctga ttaagtcaga aagaaatac | 1560 |
| gaccatccag agctgattgt tgatgagtcg aatctgcgcg tggtgtatgc gccaagccgt | 1620 |
| tattttgcca gcgagcccaa agctgatgtc agcctgatt tgcgtaatcc gaaagccatg | 1680 |
| gacagcgccc gcaatcaggt gatgtttgcg ctcaatgatt atctcgcagg gctggcgctt | 1740 |
| gatcagttaa gcaaccaggc gtcggttggt ggcataagtt tttccaccaa cgctaacaac | 1800 |
| ggccttatgg ttaatgctaa tggttacacc cagcgtctgc cgcagctgtt ccaggcattg | 1860 |
| ctcgaggggt actttagcta taccgctacg gaagatcagc ttgagcaggc gaagtcctgg | 1920 |
| tataaccaga tgatggattc cgcagaaaag ggtaaagcgt ttgagcaggc gattatgccc | 1980 |

```
gcgcagatgc tctcgcaagt gccgtacttc tcgcgagatg aacggcgtaa aattttgccc    2040
tccattacgt tgaaagaggt gctggcctat cgcgacgcct taaaatcagg ggctcgacca    2100
gagtttatgg ttatcggcaa catgaccgag gcccaggcaa caacgctggc acgcgatgtg    2160
caaaaacagt tgggcgctga tggttcagag tggtgtcgaa acaaagatgt agtggtcgat    2220
aaaaaacaat ccgtcatctt tgaaaaagcc ggtaacagca ccgactccgc actggcagcg    2280
gtatttgtac cgactggcta cgatgaatac accagctcag cctatagctc tctgttgggg    2340
cagatcgtac agccgtggtt ctacaatcag ttgcgtaccg aagaacaatt gggctatgcc    2400
gtgtttgcgt ttccaatgag cgtggggcgt cagtggggca tgggcttcct tttgcaaagc    2460
aatgataaac agccttcatt cttgtgggag cgttacaagg cgttttttccc aaccgcagag    2520 gcaaaattgc gagcgatgaa gccagatgag tttgcgcaaa tccagcaggc ggtaattacc    2580
cagatgctgc aggcaccgca aacgctcggc gaagaagcat cgaagttaag taaagatttc    2640
gatcgcggca atatgcgctt cgattcgcgt gataaaatcg tggcccagat aaaactgctg    2700
acgccgcaaa aacttgctga tttcttccat caggcggtgg tcgagccgca aggcatggct    2760
attctgtcgc agatttccgg cagccagaac gggaaagccg aatatgtaca ccctgaaggc    2820
tggaaagtgt gggagaacgt cagcgcgttg cagcaaacaa tgcccctgat gagtgaaaag    2880
aatgagtga                                                            2889
```

<210> SEQ ID NO 5
<211> LENGTH: 962
<212> TYPE: PRT
<213> ORGANISM: E. coli

<400> SEQUENCE: 5

```
Met Pro Arg Ser Thr Trp Phe Lys Ala Leu Leu Leu Val Ala Leu
1               5                   10                  15

Trp Ala Pro Leu Ser Gln Ala Glu Thr Gly Trp Gln Pro Ile Gln Glu
                20                  25                  30

Thr Ile Arg Lys Ser Asp Lys Asp Asn Arg Gln Tyr Gln Ala Ile Arg
            35                  40                  45

Leu Asp Asn Gly Met Val Val Leu Leu Val Ser Asp Pro Gln Ala Val
        50                  55                  60

Lys Ser Leu Ser Ala Leu Val Val Pro Val Gly Ser Leu Glu Asp Pro
65                  70                  75                  80

Glu Ala Tyr Gln Gly Leu Ala His Tyr Leu Glu His Met Ser Leu Met
                85                  90                  95

Gly Ser Lys Lys Tyr Pro Gln Ala Asp Ser Leu Ala Glu Tyr Leu Lys
            100                 105                 110

Met His Gly Gly Ser His Asn Ala Ser Thr Ala Pro Tyr Arg Thr Ala
        115                 120                 125

Phe Tyr Leu Glu Val Glu Asn Asp Ala Leu Pro Gly Ala Val Asp Arg
    130                 135                 140

Leu Ala Asp Ala Ile Ala Glu Pro Leu Leu Asp Lys Lys Tyr Ala Glu
145                 150                 155                 160

Arg Glu Arg Asn Ala Val Asn Ala Glu Leu Thr Met Ala Arg Thr Arg
                165                 170                 175

Asp Gly Met Arg Met Ala Gln Val Ser Ala Glu Thr Ile Asn Pro Ala
            180                 185                 190

His Pro Gly Ser Lys Phe Ser Gly Gly Asn Leu Glu Thr Leu Ser Asp
        195                 200                 205
```

```
Lys Pro Gly Asn Pro Val Gln Gln Ala Leu Lys Asp Phe His Glu Lys
210                 215                 220

Tyr Tyr Ser Ala Asn Leu Met Lys Ala Val Ile Tyr Ser Asn Lys Pro
225                 230                 235                 240

Leu Pro Glu Leu Ala Lys Met Ala Ala Asp Thr Phe Gly Arg Val Pro
                245                 250                 255

Asn Lys Glu Ser Lys Lys Pro Glu Ile Thr Val Pro Val Val Thr Asp
                260                 265                 270

Ala Gln Lys Gly Ile Ile Ile His Tyr Val Pro Ala Leu Pro Arg Lys
                275                 280                 285

Val Leu Arg Val Glu Phe Arg Ile Asp Asn Asn Ser Ala Lys Phe Arg
290                 295                 300

Ser Lys Thr Asp Glu Leu Ile Thr Tyr Leu Ile Gly Asn Arg Ser Pro
305                 310                 315                 320

Gly Thr Leu Ser Asp Trp Leu Gln Lys Gln Gly Leu Val Glu Gly Ile
                325                 330                 335

Ser Ala Asn Ser Asp Pro Ile Val Asn Gly Asn Ser Gly Val Leu Ala
                340                 345                 350

Ile Ser Ala Ser Leu Thr Asp Lys Gly Leu Ala Asn Arg Asp Gln Val
                355                 360                 365

Val Ala Ala Ile Phe Ser Tyr Leu Asn Leu Leu Arg Glu Lys Gly Ile
370                 375                 380

Asp Lys Gln Tyr Phe Asp Glu Leu Ala Asn Val Leu Asp Ile Asp Phe
385                 390                 395                 400

Arg Tyr Pro Ser Ile Thr Arg Asp Met Asp Tyr Val Glu Trp Leu Ala
                405                 410                 415

Asp Thr Met Ile Arg Val Pro Val Glu His Thr Leu Asp Ala Val Asn
                420                 425                 430

Ile Ala Asp Arg Tyr Asp Ala Lys Ala Val Lys Glu Arg Leu Ala Met
                435                 440                 445

Met Thr Pro Gln Asn Ala Arg Ile Trp Tyr Ile Ser Pro Lys Glu Pro
                450                 455                 460

His Asn Lys Thr Ala Tyr Phe Val Asp Ala Pro Tyr Gln Val Asp Lys
465                 470                 475                 480

Ile Ser Ala Gln Thr Phe Ala Asp Trp Gln Lys Ala Ala Asp Ile
                485                 490                 495

Ala Leu Ser Leu Pro Glu Leu Asn Pro Tyr Ile Pro Asp Phe Ser
                500                 505                 510

Leu Ile Lys Ser Glu Lys Lys Tyr Asp His Pro Glu Leu Ile Val Asp
                515                 520                 525

Glu Ser Asn Leu Arg Val Val Tyr Ala Pro Ser Arg Tyr Phe Ala Ser
                530                 535                 540

Glu Pro Lys Ala Asp Val Ser Leu Ile Leu Arg Asn Pro Lys Ala Met
545                 550                 555                 560

Asp Ser Ala Arg Asn Gln Val Met Phe Ala Leu Asn Asp Tyr Leu Ala
                565                 570                 575

Gly Leu Ala Leu Asp Gln Leu Ser Asn Gln Ala Ser Val Gly Gly Ile
                580                 585                 590

Ser Phe Ser Thr Asn Ala Asn Asn Gly Leu Met Val Asn Ala Asn Gly
                595                 600                 605

Tyr Thr Gln Arg Leu Pro Gln Leu Phe Gln Ala Leu Leu Glu Gly Tyr
                610                 615                 620
```

-continued

```
Phe Ser Tyr Thr Ala Thr Glu Asp Gln Leu Glu Gln Ala Lys Ser Trp
625                 630                 635                 640

Tyr Asn Gln Met Met Asp Ser Ala Glu Lys Gly Lys Ala Phe Glu Gln
            645                 650                 655

Ala Ile Met Pro Ala Gln Met Leu Ser Gln Val Pro Tyr Phe Ser Arg
        660                 665                 670

Asp Glu Arg Arg Lys Ile Leu Pro Ser Ile Thr Leu Lys Glu Val Leu
    675                 680                 685

Ala Tyr Arg Asp Ala Leu Lys Ser Gly Ala Arg Pro Glu Phe Met Val
690                 695                 700

Ile Gly Asn Met Thr Glu Ala Gln Ala Thr Thr Leu Ala Arg Asp Val
705                 710                 715                 720

Gln Lys Gln Leu Gly Ala Asp Gly Ser Glu Trp Cys Arg Asn Lys Asp
                725                 730                 735

Val Val Val Asp Lys Lys Gln Ser Val Ile Phe Glu Lys Ala Gly Asn
            740                 745                 750

Ser Thr Asp Ser Ala Leu Ala Ala Val Phe Val Pro Thr Gly Tyr Asp
        755                 760                 765

Glu Tyr Thr Ser Ser Ala Tyr Ser Ser Leu Leu Gly Gln Ile Val Gln
    770                 775                 780

Pro Trp Phe Tyr Asn Gln Leu Arg Thr Glu Glu Gln Leu Gly Tyr Ala
785                 790                 795                 800

Val Phe Ala Phe Pro Met Ser Val Gly Arg Gln Trp Gly Met Gly Phe
                805                 810                 815

Leu Leu Gln Ser Asn Asp Lys Gln Pro Ser Phe Leu Trp Glu Arg Tyr
            820                 825                 830

Lys Ala Phe Phe Pro Thr Ala Glu Ala Lys Leu Arg Ala Met Lys Pro
        835                 840                 845

Asp Glu Phe Ala Gln Ile Gln Gln Ala Val Ile Thr Gln Met Leu Gln
    850                 855                 860

Ala Pro Gln Thr Leu Gly Glu Glu Ala Ser Lys Leu Ser Lys Asp Phe
865                 870                 875                 880

Asp Arg Gly Asn Met Arg Phe Asp Ser Arg Asp Lys Ile Val Ala Gln
                885                 890                 895

Ile Lys Leu Leu Thr Pro Gln Lys Leu Ala Asp Phe His Gln Ala
            900                 905                 910

Val Val Glu Pro Gln Gly Met Ala Ile Leu Ser Gln Ile Ser Gly Ser
        915                 920                 925

Gln Asn Gly Lys Ala Glu Tyr Val His Pro Gly Gly Trp Lys Val Trp
    930                 935                 940

Glu Asn Val Ser Ala Leu Gln Gln Thr Met Pro Leu Met Ser Glu Lys
945                 950                 955                 960

Asn Glu

<210> SEQ ID NO 6
<211> LENGTH: 2915
<212> TYPE: DNA
<213> ORGANISM: E. coli

<400> SEQUENCE: 6
attccccgca gcacctggtt caaagcatta ttgttgttag ttgccctttg ggcacattaa      60
tgtcaggcag aaacgggatg gcagccgatt caggaaacca tccgtaaaag tgataaagat     120
aaccgccagt atcaggctat acgtctggat aacggtatgg tggtcttgct ggtttctgat     180
```

```
ccgcaggcag ttaaatcgct ctcggcgctg gtggtgcccg ttgggtcgct ggaagatccc    240
gaggcgtacc aggggctggc acattacctt gaacatatga gtctgatggg gtcgaaaaag    300
tacccgcagg ctgacagtct ggccgaatat ctcaaaatgc acggcggtag tcacaatgcc    360
agcactgcgc cgtatcgcac ggctttctat ctggaagttg agaacgacgc cttgcctggt    420
gcggtagacc gcctggccga tgctattgct gaacctttgc tcgacaagaa atatgccgaa    480
cgtgagcgta atgcggtgaa cgctgaatta accatggcgc gtacgcgtga cgggatgcgc    540
atggcacagg tcagcgcaga aaccattaac ccggcacacc ccggttcaaa gttttctggt    600
ggtaacctcg aaactttaag cgacaaacct ggtaatccgg tgcagcaggc gctgaaagat    660
ttccacgaga agtactattc cgccaatttg atgaaggcgg ttatttacag taataaaccg    720
ctgccggagt tggcaaaaat ggcggcggac acctttggtc gcgtgccgaa caaagagagc    780
aaaaaaccgg aaatcaccgt gccggtagtc accgacgcgc aaaagggcat tatcattcat    840
tacgtccctg cgctgccgcg taaagtgttg cgcgttgagt ttcgcatcga taacaactca    900
gcgaagttcc gtagtaaaac cgatgaattg attacctatc tgattggcaa tcgcagccca    960
ggtacacttt ctgactggct gcaaaagcag ggattagttg agggcattag cgccaactcc   1020
gatcctatcg tcaacggcaa cagcggcgta ttagcgatct ctgcgtcttt aaccgataaa   1080
ggcctggcta atcgcgatca ggttgtggcg gcaatttta gctatctcaa tctgttacgt    1140
gaaaaaggca ttgataaaca atacttcgat gaactggcga atgtgctgga tatcgacttc   1200
cgttatccgt cgatcacccg tgatatggat tacgtcgaat ggctggcaga taccatgatt   1260
cgcgttcctg ttgagcatac gctggatgca gtcaatattg ccgatcggta cgatgctaaa   1320
gcagtaaagg aacgtctggc gatgatgacg ccgcagaatg cgcgtatctg gtatatcagc   1380
ccgaaagagc cgcacaacaa aacggcttac tttgtcgatg cgccgtatca ggtcgataaa   1440
atcagcgcac aaactttcgc cgactggcag aaaaaagccg ccgacattgc gctctctttg   1500
ccagagctta acccttatat tcctgatgat ttctcgctga ttaagtcaga gaagaaatac   1560
gaccatccag agctgattgt tgatgagtcg aatctgcgcg tggtgtatgc gccaagccgt   1620
tattttgcca gcgagcccaa agctgatgtc agcctgattt tgcgtaatcc gaaagccatg   1680
gacagcgccc gcaatcaggt gatgtttgcg ctcaatgatt atctcgcagg gctggcgctt   1740
gatcagttaa gcaaccaggc gtcggttggt ggcataagtt tttccaccaa cgctaacaac   1800
ggccttatgg ttaatgctaa tggttacacc cagcgtctgc cgcagctgtt ccaggcattg   1860
ctcgaggggt actttagcta taccgctacg gaagatcagc ttgagcaggc gaagtcctgg   1920
tataaccaga tgatggattc cgcagaaaag ggtaaagcgt ttgagcaggc gattatgccc   1980
gcgcagatgc tctcgcaagt gccgtacttc tcgcgagatg aacggcgtaa aattttgccc   2040
tccattacgt tgaaagaggt gctggcctat cgcgacgcct aaaatcagg ggctcgacca    2100 gagtttatgg ttatcggcaa catgaccgag gcccaggcaa caacgctggc acgcgatgtg   2160
caaaaacagt tgggcgctga tggttcagag tggtgtcgaa acaaagatgt agtggtcgat   2220
aaaaaacaat ccgtcatcct tgaaaagcc ggtaacagca ccgactccgc actggcagcg    2280
gtatttgtac cgactggcta cgatgaatac accagctcag cctatagctc tctgttgggg   2340
cagatcgtac agccgtggtt ctacaatcag ttgcgtaccg aagaacaatt gggctatgcc   2400
gtgtttgcgt ttccaatgag cgtggggcgt cagtggggca tgggcttcct tttgcaaagc   2460
aatgataaac agccttcatt cttgtgggag cgttacaagg cgttttttccc aaccgcagag   2520 gcaaaattgc gagcgatgaa gccagatgag tttgcgcaaa tccagcaggc ggtaattacc   2580
```

```
cagatgctgc aggcaccgca aacgctcggc gaagaagcat cgaagttaag taaagatttc    2640
gatcgcggca atatgcgctt cgattcgcgt gataaaatcg tggcccagat aaaactgctg    2700
acgccgcaaa aacttgctga tttcttccat caggcggtgg tcgagccgca aggcatggct    2760
attctgtcgc agatttccgg cagccagaac gggaaagccg aatatgtaca ccctgaaggc    2820
tggaaagtgt gggagaacgt cagcgcgttg cagcaaacaa tgcccctgat gagtgaaaag    2880
aatgagtgat gtcgccgaga cactagatcc tttgc                               2915
```

<210> SEQ ID NO 7
<211> LENGTH: 1425
<212> TYPE: DNA
<213> ORGANISM: E. coli

<400> SEQUENCE: 7

```
atgaaaaaaa ccacattagc actgagtgca ctggctctga gtttaggttt ggcgttatct     60
ccgctctctg caacggcggc tgagacttct cagcaacga cagcccagca gatgccaagc    120
cttgcaccga tgctcgaaaa ggtgatgcct tcagtggtca gcattaacgt agaaggtagc    180
acaaccgtta atacgccgcg tatgccgcgt aatttccagc agttcttcgg tgatgattct    240
ccgttctgcc aggaaggttc tccgttccag agctctccgt tctgccaggg tggccagggc    300
ggtaatggtg gcggccagca acagaaattc atggcgctgg gttccggcgt catcattgat    360
gccgataaag gctatgtcgt caccaacaac cacgttgttg ataacgcgac ggtcattaaa    420
gttcaactga gcgatggccg taagttcgac gcgaagatgg ttggcaaaga tccgcgctct    480
gatatcgcgc tgatccaaat ccagaacccg aaaaacctga ccgcaattaa gatggcggat    540
tctgatgcac tgcgcgtggg tgattacacc gtagcgattg gtaacccgtt tggtctgggc    600
gagacggtaa cttccgggat tgtctctgcg ctggggcgta gcggcctgaa tgccgaaaac    660
tacgaaaact tcatccagac cgatgcagcg atcaaccgtg gtaactccgg tggtgcgctg    720
gttaacctga cggcgaact gatcggtatc aacaccgcga tcctcgcacc ggacggcggc    780
aacatcggta tcggtttgc tatcccgagt aacatggtga aaaacctgac ctcgcagatg    840
gtggaatacg ccaggtgaa acgcggtgag ctggtatta tggggactga gctgaactcc    900
gaactggcga agcgatgaa agttgacgcc cagcgcggtg ctttcgtaag ccaggttctg    960
cctaattcct ccgctgcaaa agcgggcatt aaagcgggtc atgtgatcac ctcactgaac   1020
ggtaagccga tcagcagctt tgccgcactg cgtgctcagg tgggtactat gccggtaggc   1080
agcaaactga cctgggctt actgcgcgac ggtaagcagg ttaacgtgaa cctggaactg   1140
cagcagagca gccagaatca ggttgattcc agctccatct tcaacggcat tgaaggcgct   1200
gagatgagca acaaaggcaa agatcagggc gtggtagtga acaacgtgaa aacgggcact   1260
ccggctgcgc agatcggcct gaagaaaggt gatgtgatta ttggcgcgaa ccagcaggca   1320
gtgaaaaaca tcgctgaact gcgtaaagtt ctcgacagca aaccgtctgt gctggcactc   1380
aacattcagc gcggcgacag caccatctac ctgttaatgc agtaa                   1425
```

<210> SEQ ID NO 8
<211> LENGTH: 474
<212> TYPE: PRT
<213> ORGANISM: E. coli

<400> SEQUENCE: 8

```
Met Lys Lys Thr Thr Leu Ala Leu Ser Ala Leu Ala Leu Ser Leu Gly
1               5                   10                  15
```

```
Leu Ala Leu Ser Pro Leu Ser Ala Thr Ala Ala Glu Thr Ser Ser Ala
             20                  25                  30

Thr Thr Ala Gln Gln Met Pro Ser Leu Ala Pro Met Leu Glu Lys Val
         35                  40                  45

Met Pro Ser Val Val Ser Ile Asn Val Glu Gly Ser Thr Thr Val Asn
 50                  55                  60

Thr Pro Arg Met Pro Arg Asn Phe Gln Gln Phe Phe Gly Asp Asp Ser
 65                  70                  75                  80

Pro Phe Cys Gln Glu Gly Ser Pro Phe Gln Ser Ser Pro Phe Cys Gln
                 85                  90                  95

Gly Gly Gln Gly Gly Asn Gly Gly Gln Gln Gln Lys Phe Met Ala
                100                 105                 110

Leu Gly Ser Gly Val Ile Ile Asp Ala Asp Lys Gly Tyr Val Val Thr
            115                 120                 125

Asn Asn His Val Val Asp Asn Ala Thr Val Ile Lys Val Gln Leu Ser
    130                 135                 140

Asp Gly Arg Lys Phe Asp Ala Lys Met Val Gly Lys Asp Pro Arg Ser
145                 150                 155                 160

Asp Ile Ala Leu Ile Gln Ile Gln Asn Pro Lys Asn Leu Thr Ala Ile
                165                 170                 175

Lys Met Ala Asp Ser Asp Ala Leu Arg Val Gly Asp Tyr Thr Val Ala
                180                 185                 190

Ile Gly Asn Pro Phe Gly Leu Gly Glu Thr Val Thr Ser Gly Ile Val
            195                 200                 205

Ser Ala Leu Gly Arg Ser Gly Leu Asn Ala Glu Asn Tyr Glu Asn Phe
    210                 215                 220

Ile Gln Thr Asp Ala Ala Ile Asn Arg Gly Asn Ser Gly Gly Ala Leu
225                 230                 235                 240

Val Asn Leu Asn Gly Glu Leu Ile Gly Ile Asn Thr Ala Ile Leu Ala
                245                 250                 255

Pro Asp Gly Gly Asn Ile Gly Ile Gly Phe Ala Ile Pro Ser Asn Met
                260                 265                 270

Val Lys Asn Leu Thr Ser Gln Met Val Glu Tyr Gly Asn Val Lys Arg
            275                 280                 285

Gly Glu Leu Gly Ile Met Gly Thr Glu Leu Asn Ser Glu Leu Ala Lys
    290                 295                 300

Ala Met Lys Val Asp Ala Gln Arg Gly Ala Phe Val Ser Gln Val Leu
305                 310                 315                 320

Pro Asn Ser Ser Ala Ala Lys Ala Gly Ile Lys Ala Gly Asp Val Ile
                325                 330                 335

Thr Ser Leu Asn Gly Lys Pro Ile Ser Ser Phe Ala Ala Leu Arg Ala
            340                 345                 350

Gln Val Gly Thr Met Pro Val Gly Ser Lys Leu Thr Leu Gly Leu Leu
    355                 360                 365

Arg Asp Gly Lys Gln Val Asn Val Asn Leu Glu Leu Gln Gln Ser Ser
370                 375                 380

Gln Asn Gln Val Asp Ser Ser Ile Phe Asn Gly Ile Glu Gly Ala
385                 390                 395                 400

Glu Met Ser Asn Lys Gly Lys Asp Gln Gly Val Val Asn Asn Val
                405                 410                 415

Lys Thr Gly Thr Pro Ala Ala Gln Ile Gly Leu Lys Lys Gly Asp Val
            420                 425                 430
```

Ile Ile Gly Ala Asn Gln Gln Ala Val Lys Asn Ile Ala Glu Leu Arg
            435                 440                 445

Lys Val Leu Asp Ser Lys Pro Ser Val Leu Ala Leu Asn Ile Gln Arg
        450                 455                 460

Gly Asp Ser Thr Ile Tyr Leu Leu Met Gln
465                 470

<210> SEQ ID NO 9
<211> LENGTH: 1425
<212> TYPE: DNA
<213> ORGANISM: E. coli

<400> SEQUENCE: 9
atgaaaaaaa ccacattagc actgagtgca ctggctctga gtttaggttt ggcgttatct     60
ccgctctctg caacggcggc tgagacttct tcagcaacga cagcccagca gatgccaagc    120
cttgcaccga tgctcgaaaa ggtgatgcct tcagtggtca gcattaacgt agaaggtagc    180
acaaccgtta atacgccgcg tatgccgcgt aatttccagc agttcttcgg tgatgattct    240
ccgttctgcc aggaaggttc tccgttccag agctctccgt tctgccaggg tggccagggc    300
ggtaatggtg gcggccagca acagaaattc atggcgctgg ttccggcgt catcattgat    360
gccgataaag gctatgtcgt caccaacaac cacgttgttg ataacgcgac ggtcattaaa    420
gttcaactga gcgatggccg taagttcgac gcgaagatgg ttggcaaaga tccgcgctct    480
gatatcgcgc tgatccaaat ccagaacccg aaaaacctga ccgcaattaa gatggcggat    540
tctgatgcac tgcgcgtggg tgattacacc gtagcgattg gtaacccgtt tggtctgggc    600
gagacggtaa cttccgggat tgtctctgcg ctggggcgta gcggcctgaa tgccgaaaac    660
tacgaaaact tcatccagac cgatgcagcg attaatcgtg gtaacgccgg tggtgcgctg    720
gttaacctga acggcgaact gatcggtatc aacaccgcga tcctcgcacc ggacggcggc    780
aacatcggta tcggttttgc tatcccgagt aacatggtga aaaacctgac ctcgcagatg    840
gtggaatacg gccaggtgaa acgcggtgag ctgggtatta tggggactga gctgaactcc    900
gaactggcga aagcgatgaa agttgacgcc cagcgcggtg ctttcgtaag ccaggttctg    960
cctaattcct ccgctgcaaa agcgggcatt aaagcgggtg atgtgatcac ctcactgaac   1020
ggtaagccga tcagcagctt tgccgcactg cgtgctcagg tgggtactat gccggtaggc   1080
agcaaactga cctgggctt actgcgcgac ggtaagcagg ttaacgtgaa cctggaactg   1140
cagcagagca gccagaatca ggttgattcc agctccatct tcaacggcat tgaaggcgct   1200
gagatgagca acaaaggcaa agatcagggc gtggtagtga acaacgtgaa aacgggcact   1260
ccggctgcgc agatcggcct gaagaaaggt gatgtgatta ttggcgcgaa ccagcaggca   1320
gtgaaaaaca tcgctgaact gcgtaaagtt ctcgacagca accgtctgt gctggcactc   1380
aacattcagc gcggcgacag caccatctac ctgttaatgc agtaa              1425

<210> SEQ ID NO 10
<211> LENGTH: 474
<212> TYPE: PRT
<213> ORGANISM: E. coli

<400> SEQUENCE: 10

Met Lys Lys Thr Thr Leu Ala Leu Ser Ala Leu Ala Leu Ser Leu Gly
1               5                   10                  15

Leu Ala Leu Ser Pro Leu Ser Ala Thr Ala Ala Glu Thr Ser Ser Ala
            20                  25                  30

-continued

```
Thr Thr Ala Gln Gln Met Pro Ser Leu Ala Pro Met Leu Glu Lys Val
         35                  40                  45
Met Pro Ser Val Val Ser Ile Asn Val Glu Gly Ser Thr Thr Val Asn
 50                  55                  60
Thr Pro Arg Met Pro Arg Asn Phe Gln Gln Phe Phe Gly Asp Asp Ser
 65                  70                  75                  80
Pro Phe Cys Gln Glu Gly Ser Pro Phe Gln Ser Ser Pro Phe Cys Gln
                 85                  90                  95
Gly Gly Gln Gly Gly Asn Gly Gly Gln Gln Gln Lys Phe Met Ala
                100                 105                 110
Leu Gly Ser Gly Val Ile Ile Asp Ala Asp Lys Gly Tyr Val Val Thr
             115                 120                 125
Asn Asn His Val Val Asp Asn Ala Thr Val Ile Lys Val Gln Leu Ser
    130                 135                 140
Asp Gly Arg Lys Phe Asp Ala Lys Met Val Gly Lys Asp Pro Arg Ser
145                 150                 155                 160
Asp Ile Ala Leu Ile Gln Ile Gln Asn Pro Lys Asn Leu Thr Ala Ile
                165                 170                 175
Lys Met Ala Asp Ser Asp Ala Leu Arg Val Gly Asp Tyr Thr Val Ala
            180                 185                 190
Ile Gly Asn Pro Phe Gly Leu Gly Glu Thr Val Thr Ser Gly Ile Val
    195                 200                 205
Ser Ala Leu Gly Arg Ser Gly Leu Asn Ala Glu Asn Tyr Glu Asn Phe
210                 215                 220
Ile Gln Thr Asp Ala Ala Ile Asn Arg Gly Asn Ala Gly Gly Ala Leu
225                 230                 235                 240
Val Asn Leu Asn Gly Glu Leu Ile Gly Ile Asn Thr Ala Ile Leu Ala
                245                 250                 255
Pro Asp Gly Gly Asn Ile Gly Ile Gly Phe Ala Ile Pro Ser Asn Met
            260                 265                 270
Val Lys Asn Leu Thr Ser Gln Met Val Glu Tyr Gly Gln Val Lys Arg
    275                 280                 285
Gly Glu Leu Gly Ile Met Gly Thr Glu Leu Asn Ser Glu Leu Ala Lys
290                 295                 300
Ala Met Lys Val Asp Ala Gln Arg Gly Ala Phe Val Ser Gln Val Leu
305                 310                 315                 320
Pro Asn Ser Ser Ala Ala Lys Ala Gly Ile Lys Ala Gly Asp Val Ile
                325                 330                 335
Thr Ser Leu Asn Gly Lys Pro Ile Ser Ser Phe Ala Ala Leu Arg Ala
            340                 345                 350
Gln Val Gly Thr Met Pro Val Gly Ser Lys Leu Thr Leu Gly Leu Leu
    355                 360                 365
Arg Asp Gly Lys Gln Val Asn Val Asn Leu Glu Leu Gln Gln Ser Ser
370                 375                 380
Gln Asn Gln Val Asp Ser Ser Ile Phe Asn Gly Ile Glu Gly Ala
385                 390                 395                 400
Glu Met Ser Asn Lys Gly Lys Asp Gln Gly Val Val Val Asn Asn Val
                405                 410                 415
Lys Thr Gly Thr Pro Ala Ala Gln Ile Gly Leu Lys Lys Gly Asp Val
            420                 425                 430
Ile Ile Gly Ala Asn Gln Gln Ala Val Lys Asn Ile Ala Glu Leu Arg
    435                 440                 445
```

Lys Val Leu Asp Ser Lys Pro Ser Val Leu Ala Leu Asn Ile Gln Arg
            450             455                 460
Gly Asp Ser Thr Ile Tyr Leu Leu Met Gln
465                 470

<210> SEQ ID NO 11
<211> LENGTH: 107
<212> TYPE: PRT
<213> ORGANISM: Artificial Sequence
<220> FEATURE:
<223> OTHER INFORMATION: hTNF40-gL1

<400> SEQUENCE: 11

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asn Val Gly Thr Asn
            20                  25                  30
Val Ala Trp Tyr Gln Gln Lys Pro Gly Lys Ala Pro Lys Ala Leu Ile
        35                  40                  45
Tyr Ser Ala Ser Phe Leu Tyr Ser Gly Val Pro Tyr Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ile Tyr Pro Leu
                85                  90                  95
Thr Phe Gly Gln Gly Thr Lys Val Glu Ile Lys
            100                 105

<210> SEQ ID NO 12
<211> LENGTH: 118
<212> TYPE: PRT
<213> ORGANISM: Artificial Sequence
<220> FEATURE:
<223> OTHER INFORMATION: gh3h TNF40.4

<400> SEQUENCE: 12

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Val Phe Thr Asp Tyr
            20                  25                  30
Gly Met Asn Trp Val Arg Gln Ala Pro Gly Lys Gly Leu Glu Trp Met
        35                  40                  45
Gly Trp Ile Asn Thr Tyr Ile Gly Glu Pro Ile Tyr Ala Asp Ser Val
    50                  55                  60
Lys Gly Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Arg Gly Tyr Arg Ser Tyr Ala Met Asp Tyr Trp Gly Gln Gly Thr
            100                 105                 110
Leu Val Thr Val Ser Ser
        115

<210> SEQ ID NO 13
<211> LENGTH: 214
<212> TYPE: PRT
<213> ORGANISM: Artificial Sequence
<220> FEATURE:
<223> OTHER INFORMATION: Grafted Light Chain

```
<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 229
<212> TYPE: PRT
<213> ORGANISM: Artificial Sequence
<220> FEATURE:
<223> OTHER INFORMATION: Grafted Heavy Chain

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 15
gcatcataat tttcttttta cctc                                         24

<210> SEQ ID NO 16
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 16
gggaaatgaa cctgagcaaa acgc                                         24

<210> SEQ ID NO 17
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 17
gtgccaggag atgcagcagc ttgc                                         24

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 18
tttgcagcca gtcagaaagt g                                            21

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 19
```
ctgcctgcga ttttcgccgg aacg                                          24

<210> SEQ ID NO 20
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 20
cgcatggtac gtgccacgat atcc                                          24

<210> SEQ ID NO 21
<211> LENGTH: 188
<212> TYPE: PRT
<213> ORGANISM: Escherichia coli

<400> SEQUENCE: 21

Met Val Lys Ser Gln Pro Ile Leu Arg Tyr Ile Leu Arg Gly Ile Pro
1               5                   10                  15

Ala Ile Ala Val Ala Val Leu Leu Ser Ala Cys Ser Ala Asn Asn Thr
            20                  25                  30

Ala Lys Asn Met His Pro Glu Thr Arg Ala Val Gly Ser Glu Thr Ser
        35                  40                  45

Ser Leu Gln Ala Ser Gln Asp Glu Phe Glu Asn Leu Val Arg Asn Val
    50                  55                  60

Asp Val Lys Ser Arg Ile Met Asp Gln Tyr Ala Asp Trp Lys Gly Val
65                  70                  75                  80

Arg Tyr Arg Leu Gly Gly Ser Thr Lys Lys Gly Ile Asp Cys Ser Gly
                85                  90                  95

Phe Val Gln Arg Thr Phe Arg Glu Gln Phe Gly Leu Glu Leu Pro Arg
            100                 105                 110

Ser Thr Tyr Glu Gln Gln Glu Met Gly Lys Ser Val Ser Arg Ser Asn
        115                 120                 125

Leu Arg Thr Gly Asp Leu Val Leu Phe Arg Ala Gly Ser Thr Gly Arg
    130                 135                 140

His Val Gly Ile Tyr Ile Gly Asn Asn Gln Phe Val His Ala Ser Thr
145                 150                 155                 160

Ser Ser Gly Val Ile Ile Ser Ser Met Asn Glu Pro Tyr Trp Lys Lys
                165                 170                 175

Arg Tyr Asn Glu Ala Arg Arg Val Leu Ser Arg Ser
            180                 185

<210> SEQ ID NO 22
<211> LENGTH: 162
<212> TYPE: PRT
<213> ORGANISM: Escherichia coli

<400> SEQUENCE: 22

Cys Ser Ala Asn Asn Thr Ala Lys Asn Met His Pro Glu Thr Arg Ala
1               5                   10                  15

Val Gly Ser Glu Thr Ser Ser Leu Gln Ala Ser Gln Asp Glu Phe Glu
            20                  25                  30

Asn Leu Val Arg Asn Val Asp Val Lys Ser Arg Ile Met Asp Gln Tyr
        35                  40                  45

Ala Asp Trp Lys Gly Val Arg Tyr Arg Leu Gly Gly Ser Thr Lys Lys
    50                  55                  60

```
Gly Ile Asp Cys Ser Gly Phe Val Gln Arg Thr Phe Arg Glu Gln Phe
 65                  70                  75                  80

Gly Leu Glu Leu Pro Arg Ser Thr Tyr Glu Gln Gln Glu Met Gly Lys
                 85                  90                  95

Ser Val Ser Arg Ser Asn Leu Arg Thr Gly Asp Leu Val Leu Phe Arg
            100                 105                 110

Ala Gly Ser Thr Gly Arg His Val Gly Ile Tyr Ile Gly Asn Asn Gln
        115                 120                 125

Phe Val His Ala Ser Thr Ser Ser Gly Val Ile Ile Ser Ser Met Asn
    130                 135                 140

Glu Pro Tyr Trp Lys Lys Arg Tyr Asn Glu Ala Arg Arg Val Leu Ser
145                 150                 155                 160

Arg Ser

<210> SEQ ID NO 23
<211> LENGTH: 951
<212> TYPE: DNA
<213> ORGANISM: Artificial Sequence
<220> FEATURE:
<223> OTHER INFORMATION: Mutated OmpT sequence

<400> SEQUENCE: 23
atgcgggcga aacttctggg aatagtcctg acaaccccta ttgcgatcag ctcttttgct      60
tctaccgaga ctttatcgtt tactcctgac aacataaatg cggacattag tcttggaact     120
ctgagcggaa aaacaaaaga gcgtgtttat ctagccgaag aaggaggccg aaaagtcagt     180
caactcgact ggaaattcaa taacgctgca attattaaag gtgcaattaa ttgggatttg     240
atgccccaga tatctatcgg ggctgctggc tggacaactc tcggcagccg aggtggcaat     300
atggtcgatc aggactggat ggattccagt aaccccggaa cctggacgga tgaaagtaga     360
caccctgata cacaactcaa ttatgccaac gaatttgatc tgaatatcaa aggctggctc     420
ctcaacgaac ccaattaccg cctgggactc atgccggat atcaggaaag ccgttatagc     480
tttacagcca gaggtggttc ctatatctac agttctgagg agggattcag agatgatatc     540
ggctccttcc cgaatggaga aagagcaatc ggctacaaac aacgttttaa aatgccctac     600
attggcttga ctggaagtta tcgttatgaa gattttgaac tcggtggcac atttaaatac     660
agcggctggg tggaatcatc tgataacgct gaagcttatg acccgggaaa aagaatcact     720
tatcgcagta aggtcaaaga ccaaaattac tattctgttg cagtcaatgc aggttattac     780
gtcacaccta acgcaaaagt ttatgttgaa ggcgcatgga atcgggttac gaataaaaaa     840
ggtaatactt cactttatga tcacaataat aacacttcag actacagcaa aaatggagca     900
ggtatagaaa actataactt catcactact gctggtctta agtacacatt t             951

<210> SEQ ID NO 24
<211> LENGTH: 317
<212> TYPE: PRT
<213> ORGANISM: Artificial Sequence
<220> FEATURE:
<223> OTHER INFORMATION: Mutated OmpT sequence

<400> SEQUENCE: 24

Met Arg Ala Lys Leu Leu Gly Ile Val Leu Thr Thr Pro Ile Ala Ile
 1               5                  10                  15

Ser Ser Phe Ala Ser Thr Glu Thr Leu Ser Phe Thr Pro Asp Asn Ile
                20                  25                  30
```

```
Asn Ala Asp Ile Ser Leu Gly Thr Leu Ser Gly Lys Thr Lys Glu Arg
             35                  40                  45

Val Tyr Leu Ala Glu Glu Gly Gly Arg Lys Val Ser Gln Leu Asp Trp
 50                  55                  60

Lys Phe Asn Asn Ala Ala Ile Ile Lys Gly Ala Ile Asn Trp Asp Leu
 65                  70                  75                  80

Met Pro Gln Ile Ser Ile Gly Ala Ala Gly Trp Thr Thr Leu Gly Ser
                 85                  90                  95

Arg Gly Gly Asn Met Val Asp Gln Asp Trp Met Asp Ser Ser Asn Pro
                100                 105                 110

Gly Thr Trp Thr Asp Glu Ser Arg His Pro Asp Thr Gln Leu Asn Tyr
            115                 120                 125

Ala Asn Glu Phe Asp Leu Asn Ile Lys Gly Trp Leu Leu Asn Glu Pro
130                 135                 140

Asn Tyr Arg Leu Gly Leu Met Ala Gly Tyr Gln Glu Ser Arg Tyr Ser
145                 150                 155                 160

Phe Thr Ala Arg Gly Gly Ser Tyr Ile Tyr Ser Ser Glu Glu Gly Phe
                165                 170                 175

Arg Asp Asp Ile Gly Ser Phe Pro Asn Gly Glu Arg Ala Ile Gly Tyr
                180                 185                 190

Lys Gln Arg Phe Lys Met Pro Tyr Ile Gly Leu Thr Gly Ser Tyr Arg
            195                 200                 205

Tyr Glu Asp Phe Glu Leu Gly Gly Thr Phe Lys Tyr Ser Gly Trp Val
210                 215                 220

Glu Ser Ser Asp Asn Ala Glu Ala Tyr Asp Pro Gly Lys Arg Ile Thr
225                 230                 235                 240

Tyr Arg Ser Lys Val Lys Asp Gln Asn Tyr Tyr Ser Val Ala Val Asn
                245                 250                 255

Ala Gly Tyr Tyr Val Thr Pro Asn Ala Lys Val Tyr Val Glu Gly Ala
                260                 265                 270

Trp Asn Arg Val Thr Asn Lys Lys Gly Asn Thr Ser Leu Tyr Asp His
            275                 280                 285

Asn Asn Asn Thr Ser Asp Tyr Ser Lys Asn Gly Ala Gly Ile Glu Asn
290                 295                 300

Tyr Asn Phe Ile Thr Thr Ala Gly Leu Lys Tyr Thr Phe
305                 310                 315

<210> SEQ ID NO 25
<211> LENGTH: 954
<212> TYPE: DNA
<213> ORGANISM: Artificial Sequence
<220> FEATURE:
<223> OTHER INFORMATION: Mutated OmpT sequence

<400> SEQUENCE: 25
attcgggcga aacttctggg aatagtcctg acaacccta ttgcgatcag ctcttttgct      60
tctaccgaga ctttatcgtt tactcctgac aacataaatg cggacattag tcttggaact    120
ctgagcggaa aaacaaaaga gcgtgtttat ctagccgaag aaggaggccg aaaagtcagt    180
caactcgact ggaaattcaa taacgctgca attattaaag gtgcaattaa ttgggatttg    240
atgccccaga tatctatcgg ggctgctggc tggacaactc tcggcagccg aggtggcaat    300
atggtcgatc aggactggat ggattccagt aaccccggaa cctggacgga tgaaagtaga    360
caccctgata cacaactcaa ttatgccaac gaatttgatc tgaatatcaa aggctggctc    420
ctcaacgaac ccaattaccg cctgggactc atggccggat atcaggaaag ccgttatagc    480
```

```
tttacagcca gaggtggttc ctatatctac agttctgagg agggattcag agatgatatc    540
ggctccttcc cgaatggaga aagagcaatc ggctacaaac aacgttttaa aatgccctac    600
attggcttga ctggaagtta tcgttatgaa gattttgaac tcggtggcac atttaaatac    660
agcggctggg tggaatcatc tgataacgat gaacactatg acccgggaaa agaatcact    720 tatcgcagta aggtcaaaga ccaaaattac tattctgttg cagtcaatgc aggttattac    780
gtcacaccta acgcaaaagt ttatgttgaa ggcgcatgga atcgggttac gaataaaaaa    840
ggtaatactt cactttatga tcacaataat aacacttcag actacagcaa aaatggagca    900
ggtatagaaa actataactt catcactact gctggtctta agtacacatt ttaa          954
```

```
<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence:hTNF40 CDRH1

<400> SEQUENCE: 26

Asp Tyr Gly Met Asn
1               5

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence:hTNF40 Human
      hybrid CDRH2

<400> SEQUENCE: 27

Trp Ile Asn Thr Tyr Ile Gly Glu Pro Ile Tyr Ala Asp Ser Val Lys
1               5                   10                  15

Gly

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence:hTNF40 CDRH3

<400> SEQUENCE: 28

Gly Tyr Arg Ser Tyr Ala Met Asp Tyr
1               5

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence:hTNF40 CDRL1

<400> SEQUENCE: 29

Lys Ala Ser Gln Asn Val Gly Thr Asn Val Ala
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence:hTNF40 CDRL2
```

-continued

<400> SEQUENCE: 30

Ser Ala Ser Phe Leu Tyr Ser
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence:hTNF40 CDRL3

<400> SEQUENCE: 31

Gln Gln Tyr Asn Ile Tyr Pro Leu Thr
1               5

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence:hTNF40 CDRH2

<400> SEQUENCE: 32

Trp Ile Asn Thr Tyr Ile Gly Glu Pro Ile Tyr Val Asp Asp Phe Lys
1               5                   10                  15

Gly

<210> SEQ ID NO 33
<211> LENGTH: 84
<212> TYPE: DNA
<213> ORGANISM: Artificial Sequence
<220> FEATURE:
<223> OTHER INFORMATION: OmpA oligonucleotide adaptor

<400> SEQUENCE: 33
tcgagttcta gataacgagg cgtaaaaaat gaaaaagaca gctatcgcaa ttgcagtggc    60
cttggctctg acgtacgagt cagg                                          84

<210> SEQ ID NO 34
<211> LENGTH: 67
<212> TYPE: DNA
<213> ORGANISM: Artificial Sequence
<220> FEATURE:
<223> OTHER INFORMATION: IGS cassette-1

<400> SEQUENCE: 34
gagctcacca gtaacaaaaa gttttaatag aggagagtgt taatgaagaa gactgctata    60
gcaattg                                                             67

<210> SEQ ID NO 35
<211> LENGTH: 69
<212> TYPE: DNA
<213> ORGANISM: Artificial Sequence
<220> FEATURE:
<223> OTHER INFORMATION: IGS cassette-2

<400> SEQUENCE: 35
gagctcacca gtaacaaaaa gttttaatag aggggagtgt taaaatgaag aagactgcta    60
tagcaattg                                                           69

<210> SEQ ID NO 36
<211> LENGTH: 81

```
<212> TYPE: DNA
<213> ORGANISM: Artificial Sequence
<220> FEATURE:
<223> OTHER INFORMATION: IGS cassette-3

<400> SEQUENCE: 36
gagctcacca gtaacaaaaa gctttaatag aggagagtgt tgaggaggaa aaaaaaatga        60
agaaaactgc tatagcaatt g                                                  81

<210> SEQ ID NO 37
<211> LENGTH: 81
<212> TYPE: DNA
<213> ORGANISM: Artificial Sequence
<220> FEATURE:
<223> OTHER INFORMATION: IGS cassette-4

<400> SEQUENCE: 37
gagctcacca gtaacaaaaa gttttaatag aggagagtgt tgacgaggat tatataatga        60
agaaaactgc tatagcaatt g                                                  81
```

US 8,969,039 B2

BACTERIAL HOST STRAIN COMPRISING A MUTANT SPR GENE AND HAVING REDUCED TSP ACTIVITY

CROSS-REFERENCE TO RELATED APPLICATION

This application is the U.S. national stage application of International Patent Application No. PCT/EP2011/050413, filed Jan. 13, 2011.

The Sequence Listing for this application is labeled "Seq-List.txt" which was created on Jul. 10, 2012 and is 58 KB. The entire contents of the sequence listing is incorporated herein by reference in its entirety.

The invention relates to a recombinant bacterial host strain, particularly E. coli. The invention also relates to a method for producing a protein of interest in such a cell.

BACKGROUND OF THE INVENTION

Bacterial cells, such as E. coli, are commonly used for producing recombinant proteins. There are many advantages to using bacterial cells, such as E. coli, for producing recombinant proteins particularly due to the versatile nature of bacterial cells as host cells allowing the gene insertion via plasmids. E. coli have been used to produce many recombinant proteins including human insulin.

Despite the many advantages to using bacterial cells to produce recombinant proteins, there are still significant limitations including the difficulty of producing protease sensitive proteins. Proteases play an important role in turning over old, damaged or miss-folded proteins in the E. coli periplasm and cytoplasm. Bacterial proteases act to degrade the recombinant protein of interest, thereby often significantly reducing the yield of active protein.

A number of bacterial proteases have been identified. In E. coli proteases including Protease III (ptr), DegP, OmpT, Tsp, prlC, ptrA, ptrB, pepA-T, tsh, espc, eatA, clpP and lon have been identified.

Tsp (also known as Prc) is a 60 kDa periplasmic protease. The first known substrate of Tsp was Penicillin-binding protein-3 (PBP3) (Determination of the cleavage site involved in C-terminal processing of penicillin-binding protein 3 of Escherichia coli; Nagasawa H, Sakagami Y, Suzuki A, Suzuki H, Hara H, Hirota Y. J. Bacteriol. 1989 November; 171(11): 5890-3 and Cloning, mapping and characterization of the Escherichia coli Tsp gene which is involved in C-terminal processing of penicillin-binding protein 3; Hara H, Yamamoto Y, Higashitani A, Suzuki H, Nishimura Y. J. Bacteriol. 1991 August; 173 (15):4799-813) but it was later discovered that the Tsp was also able to cleave phage tail proteins and, therefore, it was renamed as Tail Specific Protease (Tsp) (Silber et al., Proc. Natl. Acad. Sci. USA, 89: 295-299 (1992)). Silber et al. (Deletion of the prc(tsp) gene provides evidence for additional tail-specific proteolytic activity in Escherichia coli-12; Silber, K. R., Sauer, R. T.; Mol Gen Genet 1994 242:237-240) describes a prc deletion strain (KS1000) wherein the mutation was created by replacing a segment of the prc gene with a fragment comprising a Kan$^r$ marker.

The reduction of Tsp (prc) activity is desirable to reduce the proteolysis of proteins of interest. However, it was found that cells lacking protease prc show thermosensitive growth at low osmolarity. Hara et al isolated thermoresistant revertants containing extragenic suppressor (spr) mutations (Hara et al., Microbial Drug Resistance, 2: 63-72 (1996)). Spr is an 18 kDa membrane bound periplasmic protease and the substrates of spr are Tsp and peptidoglycans in the outer membrane involved in cell wall hydrolysis during cell division. The spr gene is designated as UniProtKB/Swiss-Prot P0AFV4 (SPR_ECOLI).

Improved protease deficient strains comprising mutant spr gene have been described. Chen et al describes the construction of E. coli strains carrying different combinations of mutations in prc (Tsp) and another protease, DegP, created by amplifying the upstream and downstream regions of the gene and ligating these together on a vector comprising selection markers and a sprW174R mutation (High-level accumulation of a recombinant antibody fragment in the periplasm of Escherichia coli requires a triple-mutant (ΔDegP Δprc sprW174R) host strain (Chen C, Snedecor B, Nishihara J C, Joly J C, McFarland N, Andersen D C, Battersby J E, Champion K M. Biotechnol Bioeng. 2004 Mar. 5; 85(5):463-74). The combination of the ΔDegP, Δprc and sprW174R mutations were found to provide the highest levels of antibody light chain, antibody heavy chain and F(ab')2-LZ. EP1341899 discloses an E. coli strain that is deficient in chromosomal DegP and prc encoding proteases DegP and Prc, respectively, and harbors a mutant spr gene that encodes a protein that suppresses growth phenotypes exhibited by strains harboring prc mutants.

The present invention provides new bacterial strains carrying alternative spr mutants which provide advantageous means for producing recombinant proteins.

SUMMARY OF THE INVENTION

In a first aspect of the present invention there is provided a recombinant gram-negative bacterial cell comprising a mutant spr gene encoding a spr protein having a mutation at one or more amino acids selected from N31, R62, I70, Q73, C94, S95, V98, Q99, R100, L108, Y115, D133, V135, L136, G140, R144, H145, G147 and H157 and wherein the cell has reduced Tsp protein activity compared to a wild-type cell.

In one embodiment, the cell's genome is isogenic to a wild-type bacterial cell except for the mutated spr gene and the modification required to reduce Tsp protein activity compared to a wild-type cell.

In a second aspect the present invention provides a recombinant gram-negative bacterial cell having reduced Tsp protein activity compared to a wild-type cell and comprising a mutant spr gene encoding a spr protein, wherein the cell's genome is isogenic to a wild-type bacterial cell except for the modification required to reduce Tsp protein activity compared to a wild-type cell and the mutated spr gene.

The cells provided by the first and second aspects of the present invention show advantageous growth and protein production phenotypes.

In a third aspect, the present invention provides a method for producing a protein of interest comprising expressing the protein of interest in a recombinant gram-negative bacterial cell as defined above.

BRIEF DESCRIPTION OF THE DRAWINGS

FIG. 11a shows the 5' end of the wild type ptr (protease III) and knockout mutated ptr (protease III) protein and gene sequences.

FIG. 11b shows the 5' end of the wild type Tsp and knockout mutated Tsp protein and gene sequences.

FIG. 11c shows a region of the wild type DegP and mutated DegP protein and gene sequences.

BRIEF DESCRIPTION OF THE SEQUENCES

Figure 1:
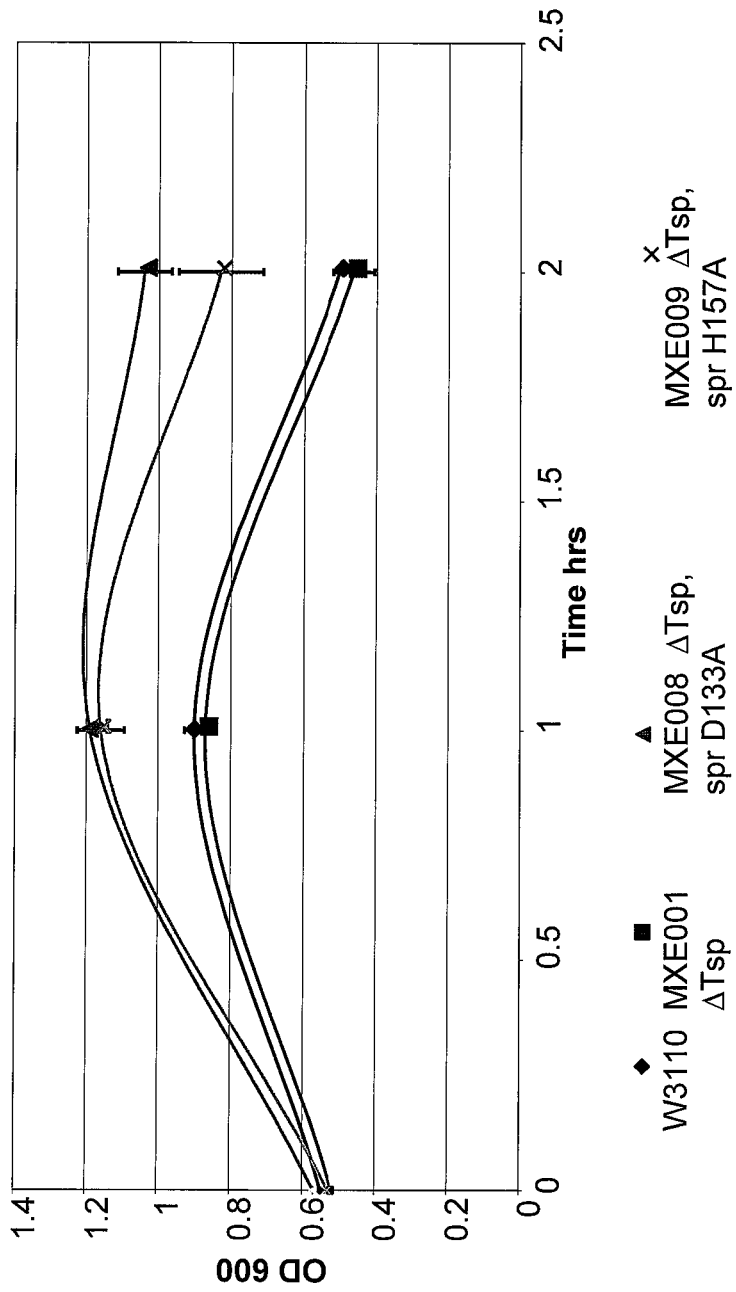
FIG. 1 shows the growth profile of anti-TNFα Fab' expressing strains MXE008 and MXE009 compared to anti-TNFα Fab' expressing wild type W3110 and MXE001 strains.

SEQ ID NO:1 is the DNA sequence of the wild-type Tsp gene including the 6 nucleotides ATGAAC upstream of the start codon.

SEQ ID NO:2 is the amino acid sequence of the wild-type Tsp protein.

SEQ ID NO:3 is the DNA sequence of a mutated knockout Tsp gene including the 6 nucleotides ATGAAT upstream of the start codon.

SEQ ID NO:4 is the DNA sequence of the wild-type Protease III gene.

SEQ ID NO:5 is the amino acid sequence of the wild-type Protease III protein.

SEQ ID NO:6 is the DNA sequence of a mutated knockout Protease III gene.

SEQ ID NO:7 is the DNA sequence of the wild-type DegP gene.

SEQ ID NO:8 is the amino acid sequence of the wild-type DegP protein.

SEQ ID NO:9 is the DNA sequence of a mutated DegP gene.

SEQ ID NO:10 is the amino acid sequence of a mutated DegP protein.

SEQ ID NO: 11 is the amino acid sequence of the light chain variable region of an anti-TNF antibody.

SEQ ID NO:12 is the amino acid sequence of the heavy chain variable region of an anti-TNF antibody.

SEQ ID NO:13 is the amino acid sequence of the light chain of an anti-TNF antibody.

SEQ ID NO:14 is the amino acid sequence of the heavy chain of an anti-TNF antibody.

SEQ ID NO: 15 is the sequence of the 3' oligonucleotide primer for the region of the mutated Tsp gene comprising the Ase I restriction site.

SEQ ID NO: 16 is the sequence of the 5' oligonucleotide primer for the region of the mutated Tsp gene comprising the Ase I restriction site.

SEQ ID NO: 17 is the sequence of the 3' oligonucleotide primer for the region of the mutated Protease III gene comprising the Ase I restriction site.

SEQ ID NO: 18 is the sequence of the 5' oligonucleotide primer for the region of the mutated Protease III gene comprising the Ase I restriction site.

SEQ ID NO: 19 is the sequence of the 5' oligonucleotide primer for the region of the mutated DegP gene comprising the Ase I restriction site.

SEQ ID NO: 20 is the sequence of the 3' oligonucleotide primer for the region of the mutated DegP gene comprising the Ase I restriction site.

SEQ ID NO: 21 is the sequence of the wild-type spr gene including the signal sequence which is the first 26 amino acid residues.

SEQ ID NO: 22 is the sequence of the non-mutated spr gene without the signal sequence.

SEQ ID NO: 23 is the nucleotide sequence of a mutated OmpT sequence comprising D210A and H212A mutations.

SEQ ID NO: 24 is the amino acid sequence of a mutated OmpT sequence comprising D210A and H212A mutations.

SEQ ID NO: 25 is the nucleotide sequence of a mutated knockout OmpT sequence.

SEQ ID NO: 26 shows the amino acid sequence of CDRH1 of hTNF40.

SEQ ID NO: 27 shows the amino acid sequence of CDRH2 of hTNF40 which is a hybrid CDR wherein the C-terminal six amino acids are from the H2CDR sequence of a human subgroup 3 germline antibody and the amino acid changes to the sequence resulting from this hybridisation are underlined as follows: WINTYIGEPI YADSVKG.

SEQ ID NO: 28 shows the amino acid sequence of CDRH3 of hTNF40.

SEQ ID NO: 29 shows the amino acid sequence of CDRL1 of hTNF40.

SEQ ID NO: 30 shows the amino acid sequence of CDRL2 of hTNF40.

SEQ ID NO: 31 shows the amino acid sequence of CDRL3 of hTNF40.

SEQ ID NO: 32 shows the amino acid sequence of CDRH2 of hTNF40.

SEQ ID NO: 33 shows the sequence of the OmpA oligonucleotide adapter.

SEQ ID NO: 34 shows the oligonucleotide cassette encoding intergenic sequence 1 (IGS1) for *E. coli* Fab expression.

SEQ ID NO: 35 shows the oligonucleotide cassette encoding intergenic sequence 2 (IGS2) for *E. coli* Fab expression.

SEQ ID NO: 36 shows the oligonucleotide cassette encoding intergenic sequence 3 (IGS3) for *E. coli* Fab expression.

SEQ ID NO: 37 shows the oligonucleotide cassette encoding intergenic sequence 4 (IGS4) for *E. coli* Fab expression.

DETAILED DESCRIPTION OF THE PREFERRED EMBODIMENTS OF THE INVENTION

The present inventors have provided a recombinant gram-negative bacterial cell suitable for expressing a protein of interest which comprises a mutated spr gene and the cell has reduced Tsp protein activity compared to a wild-type cell.

In the first aspect of the invention the new mutations to the spr provide new strains having improved cell growth phenotype compared to wild-type bacterial cells and cells carrying a mutated Tsp gene.

The present inventors have identified new spr mutations which are capable of suppressing the growth phenotype of a cell comprising a mutated Tsp gene. The inventors have surprisingly found that cells carrying the new mutated spr and having reduced Tsp activity exhibit increased cell growth rate and increase cell survival duration compared to a wild-type cell or a cell comprising a mutated Tsp gene. Specifically, cells carrying the new spr mutations and having reduced Tsp activity exhibit reduced cell lysis phenotype compared to cells carrying a mutated Tsp gene. Accordingly, the new strains reduce leakage of protein from the cells and allow prolonged periplasmic accumulation compared to cells carrying a mutated Tsp gene.

Further, cells carrying the new mutant spr and having reduced Tsp activity exhibit increased yield of a protein of interest compared to a wild-type bacterial cell or a cell comprising a mutated Tsp gene. The improved protein yield may be the periplasmic protein yield and/or the supernatant protein yield. In one embodiment the cells of the present invention show improved periplasmic protein yield compared to a cell carrying a mutated Tsp gene due to reduced leakage from the cell. The recombinant bacterial cells may be capable of faster rate of production of a protein of interest and, therefore, the same quantity of a protein of interest may be produced in a shorter time compared to a wild-type bacterial cell or a cell comprising a mutated Tsp gene. The faster rate of production of a protein of interest may be especially significant over the initial period of growth of the cell, for example over the first 5, 10, 20 or 30 hours post induction of protein expression.

The cells according to the present invention preferably express a maximum yield in the periplasm and/or media of approximately 1.0 g/L, 1.5 g/L, 1.8 g/L, 2.0 g/L, 2.4 g/L, 2.5 g/L, 3.0 g/L, 3.5 g/L or 4.0 g/L of a protein of interest.

The cells provided by the first and second aspects of the present invention have reduced protease activity of Tsp compared to a wild-type cell, which may reduce proteolysis of a protein of interest, particularly proteins of interest which are proteolytically sensitive to Tsp. Therefore, the cells provided by the first and second aspects of the present invention may provide higher yield of the intact proteins, preferably of the protein of interest and a lower yield, or preferably no proteolytic fragments of proteins, preferably of the protein of interest, compared to a wild-type bacterial cell.

In the second aspect of the invention and a preferred embodiment of the first aspect of the invention, the cells carry only the minimal mutations to the genome required to introduce the one or more spr mutations and the modification required to reduce Tsp protein activity compared to a wild-type cell. The bacterial cell only differs from a wild-type bacterial cell by the one or more mutations to the spr gene and the modification required to reduce Tsp protein activity compared to a wild-type cell. The cells do not carry any other mutations which may have deleterious effects on the cell's growth and/or ability to express a protein of interest. Accordingly, one or more of the recombinant host cells of the present invention may exhibit improved protein expression and/or improved growth characteristics compared to cells comprising further genetically engineered mutations to the genomic sequence. The cells provided by the present invention are also more suitable for use to produce therapeutic proteins compared to cells comprising further disruptions to the cell genome.

The skilled person would easily be able to test a candidate cell clone to see if it has the desired yield of a protein of interest using methods well known in the art including a fermentation method, ELISA and protein G HPLC. Suitable fermentation methods are described in Humphreys D P, et al. (1997). Formation of dimeric Fabs in *E. coli*: effect of hinge size and isotype, presence of interchain disulphide bond, Fab' expression levels, tail piece sequences and growth conditions. *J. IMMUNOL. METH.* 209: 193-202; Backlund E. Reeks D. Markland K. Weir N. Bowering L. Larsson G. Fedbatch design for periplasmic product retention in *Escherichia coli*, Journal Article. Research Support, Non-U.S. Gov't Journal of Biotechnology. 135(4):358-65, 2008 Jul. 31; Champion K M. Nishihara J C. Joly J C. Arnott D. Similarity of the *Escherichia coli* proteome upon completion of different biopharmaceutical fermentation processes. [Journal Article] Proteomics. 1(9):1133-48, 2001 September; and Horn U. Strittmatter W. Krebber A. Knupfer U. Kujau M. Wenderoth R. Muller K. Matzku S. Pluckthun A. Riesenberg D. High volumetric yields of functional dimeric miniantibodies in *Escherichia coli*, using an optimized expression vector and high-cell-density fermentation under non-limited growth conditions, Journal Article. Research Support, Non-U.S. Gov't Applied Microbiology & Biotechnology. 46(5-6):524-32, 1996 December. The skilled person would also easily be able to test secreted protein to see if the protein is correctly folded using methods well known in the art, such as protein G HPLC, circular dichroism, NMR, X-Ray crystallography and epitope affinity measurement methods.

The present invention will now be described in more detail. All embodiments herein described refer to the first, second and third aspects of the present invention unless specifically stated otherwise.

The terms "protein" and "polypeptide" are used interchangeably herein, unless the context indicates otherwise. "Peptide" is intended to refer to 10 or less amino acids.

The term "polynucleotide" includes a gene, DNA, cDNA, RNA, mRNA etc. unless the context indicates otherwise.

As used herein, the term "comprising" in context of the present specification should be interpreted as "including".

The non-mutated cell or control cell in the context of the present invention means a cell of the same type as the recombinant gram-negative cell of the invention wherein the cell has not been modified to carry the above reduce Tsp protein activity and to carry the mutant spr gene. For example, a non-mutated cell may be a wild-type cell and may be derived from the same population of host cells as the cells of the invention before modification to introduce any mutations.

The expressions "cell", "cell line", "cell culture" and "strain" are used interchangeably.

The expression "phenotype of a cell comprising a mutated Tsp gene" in the context of the present invention means the phenotype exhibited by a cell harbouring a mutant Tsp gene. Typically cells comprising a mutant Tsp gene may lyse, especially at high cell densities. The lysis of these cells causes any recombinant protein to leak into the supernatant. Cells carrying mutated Tsp gene may also show thermosensitive growth at low osmolarity. For example, the cells exhibit no or reduced growth rate or the cells die in hypotonic media at a high temperature, such as at 40° C. or more.

The term "isogenic" in the context of the present invention means that the genome of the cell of the present invention has substantially the same or the same genomic sequence compared to the wild-type cell from which the cell is derived except for mutated spr gene and the modification required to reduce Tsp protein activity compared to a wild-type cell. In this embodiment the genome of the cell comprises no further non-naturally occurring or genetically engineered mutations. In one embodiment the cell according to the present invention may have substantially the same genomic sequence compared to the wild-type cell except for the mutated spr gene and the modification required to reduce Tsp protein activity compared to a wild-type cell taking into account any naturally occurring mutations which may occur. In one embodiment, the cell according to the present invention may have exactly the same genomic sequence compared to the wild-type cell except for the mutated spr gene and the modification required to reduce Tsp protein activity compared to a wild-type cell.

The term "wild-type" in the context of the present invention means a strain of a gram-negative bacterial cell as it may occur in nature or may be isolated from the environment, which does not carry any genetically engineered mutations. An example of a wild-type strain of E. coli is W3110, such as W3110 K-12 strain.

Any suitable gram-negative bacterium may be used as the parental cell for producing the recombinant cell of the present invention. Suitable gram-negative bacterium include Salmonella typhimurium, Pseudomonas fluorescens, Erwinia carotovora, Shigella, Klebsiella pneumoniae, Legionella pneumophila, Pseudomonas aeruginosa, Acinetobacter baumannii and E. coli. Preferably the parental cell is E. coli. Any suitable strain of E. coli may be used in the present invention but preferably a wild-type W3110 strain, such as K-12 W3110, is used.

A drawback associated with the protease deficient bacterial strains previously created and used to express recombinant proteins is that they comprise additional mutations of genes involved in cell metabolism and DNA replication such as, for example phoA, fhuA, lac, rec, gal, ara, arg, thi and pro in E. coli strains. These mutations may have many deleterious effects on the host cell including effects on cell growth, stability, recombinant protein expression yield and toxicity. Strains having one or more of these genomic mutations, particularly strains having a high number of these mutations, may exhibit a loss of fitness which reduces bacterial growth rate to a level which is not suitable for industrial protein production. Further, any of the above genomic mutations may affect other genes in cis and/or in trans in unpredictable harmful ways thereby altering the strain's phenotype, fitness and protein profile. Further, the use of heavily mutated cells is not generally suitable for producing recombinant proteins for commercial use, particularly therapeutics, because such strains generally have defective metabolic pathways and hence may grow poorly or not at all in minimal or chemically defined media.

The cell according to the second aspect of the present is isogenic to a wild-type bacterial cell except for the mutated spr gene and the modification required to reduce Tsp protein activity compared to a wild-type cell. The cell according to the first aspect of the present invention is preferably also isogenic to a wild-type bacterial cell except for the mutated spr gene and the modification required to reduce Tsp protein activity compared to a wild-type cell. Only minimal mutations are made to the cell's genome to introduce the mutations. The cells do not carry any other mutations which may have deleterious effects on the cell's growth and/or ability to express a protein of interest. Accordingly, one or more of the recombinant host cells of the present invention may exhibit improved protein expression and/or improved growth characteristics compared to cells comprising further genetically engineered mutations to the genomic sequence. The cells provided by the present invention are also more suitable for use in the production of therapeutic proteins compared to cells comprising further disruptions to the cell genome.

In a preferred embodiment, the cell is isogenic to a wild-type E. coli cell, such as strain W3110, except for the mutated spr gene and the modification required to reduce Tsp protein activity compared to a wild-type cell.

The cell of the present invention may further differ from a wild-type cell by comprising a polynucleotide encoding the protein of interest. The polynucleotide sequence encoding the protein of interest may be exogenous or endogenous. The polynucleotide encoding the protein of interest may be contained within a suitable expression vector transformed into the cell and/or integrated into the host cell's genome. In the embodiment where the polynucleotide encoding the protein of interest is inserted into the host's genome, the cell of the present invention will also differ from a wild-type cell due to the inserted polynucleotide sequence encoding the protein of interest. Preferably the polynucleotide is in an expression vector in the cell thereby causing minimal disruption to the host cell's genome.

The spr protein is an E. coli membrane bound periplasmic protease.

The wild-type amino acid sequence of the spr protein is shown in SEQ ID NO:21 with the signal sequence at the N-terminus and in SEQ ID NO:22 without the signal sequence of 26 amino acids (according to UniProt Accession Number P0AFV4). The amino acid numbering of the spr protein sequence in the present invention includes the signal sequence. Accordingly, the amino acid 1 of the spr protein is the first amino acid (Met) shown in SEQ ID NO: 21.

The mutated spr gene is preferably the cell's chromosomal spr gene.

The mutated spr gene encodes a spr protein capable of suppressing the phenotype of a cell comprising a mutated Tsp gene. Cells carrying a mutated Tsp gene may have a good cell growth rate but one limitation of these cells is their tendency to lyse, especially at high cell densities. Accordingly the phenotype of a cell comprising a mutated Tsp gene is a tendency to lyse, especially at high cell densities. Cells carrying a mutated Tsp gene also show thermosensitive growth at low osmolarity. However, the spr mutations carried by the cells of the present invention, when introduced into a cell having reduced Tsp activity suppress the reduced Tsp phenotype and, therefore, the cell exhibits reduced lysis, particularly at a high cell density. The growth phenotype of a cell may be easily measured by a person skilled in the art during shake flask or high cell density fermentation technique. The suppression of the cell lysis phenotype may be been seen from the improved growth rate and/or recombinant protein production, particularly in the periplasm, exhibited by a cell carrying spr mutant and having reduced Tsp activity compared to a cell carrying the Tsp mutant and a wild-type spr.

The cells according to the first aspect of the present invention and a preferred embodiment of the second aspect comprise a mutant spr gene encoding a spr protein having a mutation at one or more amino acids selected from N31, R62, I70, Q73, C94, S95, V98, Q99, R100, L108, Y115, D133, V135, L136, G140, R144, H145, G147 and H157, preferably a mutation at one or more amino acids selected from C94, S95, V98, Y115, D133, V135, H145, G147 and H157. In this embodiment, the spr protein preferably does not have any further mutations.

The mutation of one or more of the above amino acids may be any suitable missense mutation to one, two or three of the nucleotides encoding the amino acid. The mutation changes the amino acid residue to any suitable amino acid which results in a mutated spr protein capable of suppressing the phenotype of a cell comprising a mutated Tsp gene. The missense mutation may change the amino acid to one which is a different size and/or has different chemical properties compared to the wild-type amino acid.

In one embodiment the mutant spr gene encodes an spr protein having one or more mutations selected from C94A, S95F, V98E, Y115F, D133A, V135D or G, H145A, G147C and H157A.

In one embodiment the mutation is to one, two or three of the catalytic triad of amino acid residues of C94, H145, and H157 (Solution NMR Structure of the NlpC/P60 Domain of Lipoprotein Spr from *Escherichia coli* Structural Evidence for a Novel Cysteine Peptidase Catalytic Triad, Biochemistry, 2008, 47, 9715-9717).

Accordingly, the mutated spr gene may comprise:
a mutation to C94; or
a mutation to H145; or
a mutation to H157; or
a mutation to C94 and H145; or
a mutation to C94 and H157; or
a mutation to H145 and H157; or
a mutation to C94, H145 and H157.

In this embodiment, the spr protein preferably does not have any further mutations.

One, two or three of C94, H145 and H157 may be mutated to any suitable amino acid which results in a spr protein capable of suppressing the phenotype of a cell comprising a mutated Tsp gene. For example, one, two or three of C94, H145, and H157 may be mutated to a small amino acid such as Gly or Ala. Accordingly, the spr protein may have one, two or three of the mutations C94A, H145A and H157A. Preferably, the spr gene comprises the missense mutation H145A, which has been found to produce a spr protein capable of suppressing the phenotype of a cell comprising a mutated Tsp gene.

The designation for a substitution mutant herein consists of a letter followed by a number followed by a letter. The first letter designates the amino acid in the wild-type protein. The number refers to the amino acid position where the amino acid substitution is being made, and the second letter designates the amino acid that is used to replace the wild-type amino acid.

In a preferred embodiment the mutant spr protein comprises a mutation at one or more amino acids selected from N31, R62, I70, Q73, S95, V98, Q99, R100, L108, Y115, D133, V135, L136, G140, R144 and G147, preferably a mutation at one or more amino acids selected from S95, V98, Y115, D133, V135 and G147. In this embodiment, the spr protein preferably does not have any further mutations. Accordingly, the mutated spr gene may comprise:
a mutation to N31; or
a mutation to R62; or
a mutation to I70; or
a mutation to Q73; or
a mutation to S95; or
a mutation to V98; or
a mutation to Q99; or
a mutation to R100; or
a mutation to L108; or
a mutation to Y115; or
a mutation to D133; or
a mutation to V135; or
a mutation to L136; or
a mutation to G140; or
a mutation to R144; or
a mutation to G147.

In one embodiment the mutant spr protein comprises multiple mutations to amino acids:
S95 and Y115; or
N31, Q73, R100 and G140; or
Q73, R100 and G140; or
R100 and G140; or
Q73 and G140; or
Q73 and R100; or
R62, Q99 and R144; or
Q99 and R144.

One or more of the amino acids N31, R62, I70, Q73, S95, V98, Q99, R100, L108, Y115, D133, V135, L136, G140, R144 and G147 may be mutated to any suitable amino acid which results in a spr protein capable of suppressing the phenotype of a cell comprising a mutated Tsp gene. For example, one or more of N31, R62, I70, Q73, S95, V98, Q99, R100, L108, Y115, D133, V135, L136, G140 and R144 may be mutated to a small amino acid such as Gly or Ala.

In a preferred embodiment the spr protein comprises one or more of the following mutations: N31Y, R62C, I70T, Q73R, S95F, V98E, Q99P, R100G, L108S, Y115F, D133A, V135D or V135G, L136P, G140C, R144C and G147C. Preferably the spr protein comprises one or more of the following mutations: S95F, V98E, Y115F, D133A, V135D or V135G and G147C. In this embodiment, the spr protein preferably does not have any further mutations.

In one embodiment the spr protein has one mutation selected from N31Y, R62C, I70T, Q73R, S95F, V98E, Q99P, R100G, L108S, Y115F, D133A, V135D or V135G, L136P, G140C, R144C and G147C. In this embodiment, the spr protein preferably does not have any further mutations.

In a further embodiment the spr protein has multiple mutations selected from:
S95F and Y115F
N31Y, Q73R, R100G and G140C;
Q73R, R100G and G140C;
R100G and G140C;
Q73R and G140C;
Q73R and R100G;
R62C, Q99P and R144C; or
Q99P and R144C.

Preferably the mutant spr gene encodes an spr protein having a mutation selected from H145A, H157A and D133A.

In the second aspect of the present invention, any suitable mutation or mutations may be made to the spr gene which results in a spr protein capable of suppressing the phenotype of a cell comprising a mutated Tsp gene. Preferably, the spr protein may have one or more of the following mutations: N31Y, R62C, I70T, Q73R, C94A, S95F, V98E, Q99P, R100G, L108S, Y115F, D133A, V135D, V135G, L136P, G140C, R144C, H145A, G147C, H157A and W174R. In one embodiment the spr protein does not comprise the mutation W174R. Preferably, the spr gene comprises one or more mutations discussed above with respect to the first aspect of the present invention.

The cells according to the present invention have reduced Tsp protein activity compared to a wild-type cell. The expression "reduced Tsp protein activity compared to a wild-type cell" means that the Tsp activity of the cell is reduced compared to the Tsp activity of a wild-type cell. The cell may be modified by any suitable means to reduce the activity of Tsp.

In one embodiment the reduced Tsp activity is from modification of the endogenous polynucleotide encoding Tsp and/or associated regulatory expression sequences. The modification may reduce or stop Tsp gene transcription and translation or may provide an expressed Tsp protein having reduced protease activity compared to the wild-type Tsp protein.

In one embodiment an associated regulatory expression sequence is modified to reduce Tsp expression. For example, the promoter for the Tsp gene may be mutated to prevent expression of the gene.

In a preferred embodiment the cells according to the present invention carry a mutated Tsp gene encoding a Tsp protein having reduced protease activity or a knockout mutated Tsp gene.

Preferably the chromosomal Tsp gene is mutated.

As used herein, "Tsp gene" means a gene encoding protease Tsp (also known as Prc) which is a periplasmic protease capable of acting on Penicillin-binding protein-3 (PBP3) and phage tail proteins. The sequence of the wild-type Tsp gene is shown in SEQ ID NO: 1 and the sequence of the wild-type Tsp protein is shown in SEQ ID NO: 2.

Reference to the mutated Tsp gene or mutated Tsp gene encoding Tsp, refers to either a mutated Tsp gene encoding a Tsp protein having reduced protease activity or a knockout mutated Tsp gene, unless otherwise indicated.

The expression "mutated Tsp gene encoding a Tsp protein having reduced protease activity" in the context of the present invention means that the mutated Tsp gene does not have the full protease activity compared to the wild-type non-mutated Tsp gene.

Preferably, the mutated Tsp gene encodes a Tsp protein having 50% or less, 40% or less, 30% or less, 20% or less, 10% or less or 5% or less of the protease activity of a wild-type non-mutated Tsp protein. More preferably, the mutated Tsp gene encodes a Tsp protein having no protease activity. In this embodiment the cell is not deficient in chromosomal Tsp i.e. the Tsp gene sequence has not been deleted or mutated to prevent expression of any form of Tsp protein.

Any suitable mutation may be introduced into the Tsp gene in order to produce a protein having reduced protease activity. The protease activity of a Tsp protein expressed from a gram-negative bacterium may be easily tested by a person skilled in the art by any suitable method in the art, such as the method described in Keiler et al (Identification of Active Site Residues of the Tsp Protease* THE JOURNAL OF BIOLOGICAL CHEMISTRY Vol. 270, No. 48, Issue of December 1, pp. 28864-28868, 1995 Kenneth C. Keiler and Robert T. Sauer) wherein the protease activity of Tsp was tested.

Tsp has been reported in Keiler et al (supra) as having an active site comprising residues S430, D441 and K455 and residues G375, G376, E433 and T452 are important for maintaining the structure of Tsp. Keiler et al (supra) reports findings that the mutated Tsp genes S430A, D441A, K455A, K455H, K455R, G375A, G376A, E433A and T452A had no detectable protease activity. It is further reported that the mutated Tsp gene S430C displayed about 5-10% wild-type activity. Accordingly, the Tsp mutation to produce a protein having reduced protease activity may comprise a mutation, such as a missense mutation to one or more of residues S430, D441, K455, G375, G376, E433 and T452. Preferably the Tsp mutation to produce a protein having reduced protease activity may comprise a mutation, such as a missense mutation to one, two or all three of the active site residues S430, D441 and K455.

Accordingly the mutated Tsp gene may comprise:
a mutation to S430; or
a mutation to D441; or
a mutation to K455; or
a mutation to S430 and D441; or
a mutation to S430 and K455; or
a mutation to D441 and K455; or
a mutation to S430, D441 and K455.

One or more of S430, D441, K455, G375, G376, E433 and T452 may be mutated to any suitable amino acid which results in a protein having reduced protease activity. Examples of suitable mutations are S430A, S430C, D441A, K455A, K455H, K455R, G375A, G376A, E433A and T452A. The mutated Tsp gene may comprise one, two or three mutations to the active site residues, for example the gene may comprise:
S430A or S430C; and/or
D441A; and/or
K455A or K455H or K455R.

Preferably, the Tsp gene has the point mutation S430A or S430C.

The expression "knockout mutated Tsp gene" in the context of the present invention means that the gene comprises one or more mutations which prevents expression of the Tsp protein encoded by the wild-type gene to provide a cell deficient in Tsp protein. The knockout gene may be partially or completely transcribed but not translated into the encoded protein. The knockout mutated Tsp gene may be mutated in any suitable way, for example by one or more deletion, insertion, point, missense, nonsense and frameshift mutations, to cause no expression of the protein. For example, the gene may be knocked out by insertion of a foreign DNA sequence, such as an antibiotic resistance marker, into the gene coding sequence.

In a preferred embodiment the Tsp gene is not mutated by insertion of a foreign DNA sequence, such as an antibiotic resistance marker, into the gene coding sequence. In this embodiment the Tsp gene may comprise a mutation to the gene start codon and/or one or more stop codons positioned downstream of the gene start codon and upstream of the gene stop codon thereby preventing expression of the Tsp protein. The mutation to the start codon may be a missense mutation of one, two or all three of the nucleotides of the start codon. Alternatively or additionally the start codon may be mutated by an insertion or deletion frameshift mutation. The Tsp gene comprises two ATG codons at the 5' end of the coding sequence, one or both of the ATG codons may be mutated by a missense mutation. The Tsp gene may be mutated at the second ATG codon (codon 3) to TCG, as shown in FIG. 11b. The Tsp gene may alternatively or additionally comprise one or more stop codons positioned downstream of the gene start codon and upstream of the gene stop codon. Preferably the knockout mutated Tsp gene comprises both a missense mutation to the start codon and one or more inserted stop codons. In a preferred embodiment the Tsp gene is mutated to delete "T" from the fifth codon thereby causing a frameshift resulting in stop codons at codons 11 and 16, as shown in FIG. 11b. In a preferred embodiment the Tsp gene is mutated to insert an Ase I restriction site to create a third in-frame stop codon at codon 21, as shown in FIG. 11b.

In a preferred embodiment the knockout mutated Tsp gene has the DNA sequence of SEQ ID NO: 3, which includes the 6 nucleotides ATGAAT upstream of the start codon. The mutations which have been made in the knockout mutated Tsp sequence of SEQ ID NO: 3 are shown in FIG. 11b. In one embodiment the mutated Tsp gene has the DNA sequence of nucleotides 7 to 2048 of SEQ ID NO:3.

In one embodiment the recombinant gram-negative bacterial cell further comprises a recombinant polynucleotide encoding DsbC. The polynucleotide encoding DsbC may be present on a suitable expression vector transformed into the cell and/or integrated into the host cell's genome. In the embodiment where the polynucleotide encoding DsbC is inserted into the host's genome, the cell of the present invention will also differ from a wild-type cell due to the inserted polynucleotide sequence encoding the DsbC. Preferably the polynucleotide encoding DsbC is in an expression vector in the cell thereby causing minimal disruption to the host cell's genome.

As used herein, a "recombinant polypeptide" refers to a protein that is constructed or produced using recombinant DNA technology. The polynucleotide sequence encoding DsbC may be identical to the endogenous sequence encoding DsbC found in bacterial cells. Alternatively, the recombinant polynucleotide sequence encoding DsbC is a mutated version of the wild-type DsbC sequence, for example having a restriction site removed, such as an EcoRI site, and/or a sequence encoding a his-tag.

DsbC is a prokaryotic protein found in the periplasm of *E. coli* which catalyzes the formation of disulphide bonds in *E. coli*. DsbC has an amino acid sequence length of 236 (including signal peptide) and a molecular weight of 25.6 KDa (UniProt No. P0AEG6). DsbC was first identified in 1994 (Missiakas et al. The *Escherichia coli* dsbC (xprA) gene encodes a periplasmic protein involved in disulfide bond formation, The EMBO Journal vol 13, no 8, p 2013-2020, 1994 and Shevchik et al. Characterization of DsbC, a periplasmic protein of *Erwinia chrysanthemi* and *Escherichia coli* with disulfide isomerase activity, The EMBO *Journal* vol 13, no 8, p 2007-2012, 1994).

In a preferred embodiment of the present invention the recombinant gram-negative bacterial cell further comprises a mutated DegP gene encoding a DegP protein having chaperone activity and reduced protease activity and/or a mutated ptr gene, wherein the mutated ptr gene encodes a Protease III protein having reduced protease activity or is a knockout mutated ptr gene and/or a mutated OmpT gene, wherein the mutated OmpT gene encodes an OmpT protein having reduced protease activity or is a knockout mutated OmpT gene.

In one embodiment the present invention provides a recombinant gram-negative bacterial cell comprising
  a. a mutated spr gene;
  b. a mutated Tsp gene encoding a Tsp protein having reduced protease activity or a knockout mutated Tsp gene; and
  c. a mutated DegP gene encoding a DegP protein having chaperone activity and reduced protease activity and/or a mutated OmpT wherein the mutated OmpT gene encodes an OmpT protein having reduced protease activity or is a knockout mutated OmpT gene.

Preferably in this embodiment the cell's genome is isogenic to a wild-type bacterial cell except for the above mutations.

In one embodiment the present invention provides a recombinant gram-negative bacterial cell comprising:
  a. a mutated spr gene;
  b. a mutated Tsp gene encoding a Tsp protein having reduced protease activity or a knockout mutated Tsp gene; and
  c. a mutated ptr gene, wherein the mutated ptr gene encodes a Protease III protein having reduced protease activity or is a knockout mutated ptr gene and/or a mutated OmpT wherein the mutated OmpT gene encodes an OmpT protein having reduced protease activity or is a knockout mutated OmpT gene.

Preferably in this embodiment the cell's genome is isogenic to a wild-type bacterial cell except for the above mutations.

In one embodiment the present invention provides a cell comprising
  a. a mutated spr gene;
  b. a mutated Tsp gene encoding a Tsp protein having reduced protease activity or a knockout mutated Tsp gene;
  c. a mutated DegP gene encoding a DegP protein having chaperone activity and reduced protease activity;
  d. a mutated ptr gene, wherein the mutated ptr gene encodes a Protease III protein having reduced protease activity or is a knockout mutated ptr gene; and
  e. optionally a mutated OmpT wherein the mutated OmpT gene encodes an OmpT protein having reduced protease activity or is a knockout mutated OmpT gene.

Preferably in this embodiment the cell's genome is isogenic to a wild-type bacterial cell except for the above mutations.

In one embodiment of the present invention the cell carries a mutated DegP gene. As used herein, "DegP" means a gene encoding DegP protein (also known as HtrA), which has dual function as a chaperone and a protease (Families of serine peptidases; Rawlings N D, Barrett A J. Methods Enzymol. 1994; 244:19-61). The sequence of the non-mutated DegP gene is shown in SEQ ID NO: 7 and the sequence of the non-mutated DegP protein is shown in SEQ ID NO: 8.

At low temperatures DegP functions as a chaperone and at high temperatures DegP has a preference to function as a protease (A Temperature-Dependent Switch from Chaperone to Protease in a Widely Conserved Heat Shock Protein. Cell, Volume 97, Issue 3, Pages 339-347. Spiess C, Beil A, Ehrmann M) and The proteolytic activity of the HtrA (DegP) protein from *Escherichia coli* at low temperatures, Skorko-Glonek J et al Microbiology 2008, 154, 3649-3658).

In the embodiments where the cell comprises the DegP mutation the DegP mutation in the cell provides a mutated DegP gene encoding a DegP protein having chaperone activity but not full protease activity.

The expression "having chaperone activity" in the context of the present invention means that the mutated DegP protein has the same or substantially the same chaperone activity compared to the wild-type non-mutated DegP protein. Preferably, the mutated DegP gene encodes a DegP protein having 50% or more, 60% or more, 70% or more, 80% or more, 90% or more or 95% or more of the chaperone activity of a wild-type non-mutated DegP protein. More preferably, the mutated DegP gene encodes a DegP protein having the same chaperone activity compared to wild-type DegP.

The expression "having reduced protease activity" in the context of the present invention means that the mutated DegP protein does not have the full protease activity compared to the wild-type non-mutated DegP protein. Preferably, the mutated DegP gene encodes a DegP protein having 50% or less, 40% or less, 30% or less, 20% or less, 10% or less or 5% or less of the protease activity of a wild-type non-mutated DegP protein. More preferably, the mutated DegP gene encodes a DegP protein having no protease activity. The cell is not deficient in chromosomal DegP i.e. the DegP gene sequences has not been deleted or mutated to prevent expression of any form of DegP protein.

Any suitable mutation may be introduced into the DegP gene in order to produce a protein having chaperone activity and reduced protease activity. The protease and chaperone activity of a DegP protein expressed from a gram-negative bacterium may be easily tested by a person skilled in the art by any suitable method such as the method described in Spiess et al wherein the protease and chaperone activities of DegP were tested on MalS, a natural substrate of DegP (A Temperature-Dependent Switch from Chaperone to Protease in a Widely Conserved Heat Shock Protein. Cell, Volume 97, Issue 3, Pages 339-347. Spiess C, Beil A, Ehrmann M) and also the method described in The proteolytic activity of the HtrA (DegP) protein from *Escherichia coli* at low temperatures, Skorko-Glonek J et al Microbiology 2008, 154, 3649-3658.

DegP is a serine protease and has an active center consisting of a catalytic triad of amino acid residues of His105, Asp135 and Ser210 (Families of serine peptidases, Methods Enzymol., 1994, 244:19-61 Rawlings N and Barrett A). The DegP mutation to produce a protein having chaperone activity and reduced protease activity may comprise a mutation, such as a missense mutation to one, two or three of His105, Asp135 and Ser210.

Accordingly, the mutated DegP gene may comprise:
a mutation to His105; or
a mutation to Asp135; or
a mutation to Ser210; or
a mutation to His105 and Asp135; or
a mutation to His105 and Ser210; or
a mutation to Asp135 and Ser210; or
a mutation to His105, Asp135 and Ser210.

One, two or three of His105, Asp135 and Ser210 may be mutated to any suitable amino acid which results in a protein having chaperone activity and reduced protease activity. For example, one, two or three of His105, Asp135 and Ser210 may be mutated to a small amino acid such as Gly or Ala. A further suitable mutation is to change one, two or three of His105, Asp135 and Ser210 to an amino acid having opposite properties such as Asp135 being mutated to Lys or Arg, polar His105 being mutated to a non-polar amino acid such as Gly, Ala, Val or Leu and small hydrophilic Ser210 being mutated to a large or hydrophobic residue such as Val, Leu, Phe or Tyr. Preferably, the DegP gene comprises the point mutation S210A, as shown in FIG. 11c, which has been found to produce a protein having chaperone activity but not protease activity (A Temperature-Dependent Switch from Chaperone to Protease in a Widely Conserved Heat Shock Protein. Cell, Volume 97, Issue 3, Pages 339-347. Spiess C, Beil A, Ehrmann M).

DegP has two PDZ domains, PDZ1 (residues 260-358) and PDZ2 (residues 359-448), which mediate protein-protein interaction (A Temperature-Dependent Switch from Chaperone to Protease in a Widely Conserved Heat Shock Protein. Cell, Volume 97, Issue 3, Pages 339-347. Spiess C, Beil A, Ehrmann M). In one embodiment of the present invention the degP gene is mutated to delete PDZ1 domain and/or PDZ2 domain. The deletion of PDZ1 and PDZ2 results in complete loss of protease activity of the DegP protein and lowered chaperone activity compared to wild-type DegP protein whilst deletion of either PDZ1 or PDZ2 results in 5% protease activity and similar chaperone activity compared to wild-type DegP protein (A Temperature-Dependent Switch from Chaperone to Protease in a Widely Conserved Heat Shock Protein. Cell, Volume 97, Issue 3, Pages 339-347. Spiess C, Beil A, Ehrmann M).

The mutated DegP gene may also comprise a silent non-naturally occurring restriction site, such as Ase I in order to aid in identification and screening methods, for example as shown in FIG. 11c.

The preferred sequence of the mutated DegP gene comprising the point mutation S210A and an Ase I restriction marker site is provided in SEQ ID NO: 9 and the encoded protein sequence is shown in SEQ ID NO: 10. The mutations which have been made in the mutated DegP sequence of SEQ ID NO: 9 are shown in FIG. 11c.

In the embodiments of the present invention wherein the cell comprises a mutated DegP gene encoding a DegP protein having chaperone activity and reduced protease activity, one or more of the cells provided by the present invention may provide improved yield of correctly folded proteins from the cell relative to mutated cells wherein the DegP gene has been mutated to knockout DegP preventing DegP expression, such as chromosomal deficient DegP. In a cell comprising a knockout mutated DegP gene preventing DegP expression, the chaperone activity of DegP is lost completely whereas in the cell according to the present invention the chaperone activity of DegP is retained whilst the full protease activity is lost. In these embodiments, one or more cells according to the present invention have a lower protease activity to prevent proteolysis of the protein whilst maintaining the chaperone activity to allow correct folding and transportation of the protein in the host cell.

The skilled person would easily be able to test secreted protein to see if the protein is correctly folded using methods well known in the art, such as protein G HPLC, circular dichroism, NMR, X-Ray crystallography and epitope affinity measurement methods.

In these embodiments, one or more cells according to the present invention may have improved cell growth compared to cells carrying a mutated knockout DegP gene preventing DegP expression. Without wishing to be bound by theory improved cell growth may be exhibited due to the DegP protease retaining chaperone activity which may increase capacity of the cell to process all proteins which require chaperone activity. Accordingly, the production of correctly folded proteins necessary for the cell's growth and reproduction may be increased in one or more of the cells of the present invention compared to cells carrying a DegP knockout mutation thereby improving the cellular pathways regulating growth. Further, known DegP protease deficient strains are generally temperature-sensitive and do not typically grow at temperatures higher than about 28° C. However, the cells according to the present invention are not temperature-sensitive and may be grown at temperatures of 28° C. or higher, including temperatures of approximately 30° C. to approximately 37° C., which are typically used for industrial scale production of proteins from bacteria.

In one embodiment of the present invention the cell carries a mutated ptr gene. As used herein, "ptr gene" means a gene encoding Protease III, a protease which degrades high molecular weight proteins. The sequence of the non-mutated ptr gene is shown in SEQ ID NO: 4 and the sequence of the non-mutated Protease III protein is shown in SEQ ID NO: 5.

Reference to the mutated ptr gene or mutated ptr gene encoding Protease III, refers to either a mutated ptr gene encoding a Protease III protein having reduced protease activity or a knockout mutated ptr gene, unless otherwise indicated.

The expression "mutated ptr gene encoding a Protease III protein having reduced protease activity" in the context of the present invention means that the mutated ptr gene does not have the full protease activity compared to the wild-type non-mutated ptr gene.

Preferably, the mutated ptr gene encodes a Protease III having 50% or less, 40% or less, 30% or less, 20% or less, 10% or less or 5% or less of the protease activity of a wild-type non-mutated Protease III protein. More preferably, the mutated ptr gene encodes a Protease III protein having no protease activity. In this embodiment the cell is not deficient in chromosomal ptr i.e. the ptr gene sequence has not been deleted or mutated to prevent expression of any form of Protease III protein.

Any suitable mutation may be introduced into the ptr gene in order to produce a Protease III protein having reduced protease activity. The protease activity of a Protease III protein expressed from a gram-negative bacterium may be easily tested by a person skilled in the art by any suitable method in the art.

The expression "knockout mutated ptr gene" in the context of the present invention means that the gene comprises one or more mutations thereby causing no expression of the protein encoded by the gene to provide a cell deficient in the protein encoded by the knockout mutated gene. The knockout gene may be partially or completely transcribed but not translated into the encoded protein. The knockout mutated ptr gene may be mutated in any suitable way, for example by one or more deletion, insertion, point, missense, nonsense and frameshift mutations, to cause no expression of the protein. For example, the gene may be knocked out by insertion of a foreign DNA sequence, such as an antibiotic resistance marker, into the gene coding sequence.

In a preferred embodiment the gene is not mutated by insertion of a foreign DNA sequence, such as an antibiotic resistance marker, into the gene coding sequence. Preferably the Protease III gene comprise a mutation to the gene start codon and/or one or more stop codons positioned downstream of the gene start codon and upstream of the gene stop codon thereby preventing expression of the Protease III protein.

A mutation to the target knockout gene start codon causes loss of function of the start codon and thereby ensures that the target gene does not comprise a suitable start codon at the start of the coding sequence. The mutation to the start codon may be a missense mutation of one, two or all three of the nucleotides of the start codon. Alternatively or additionally the start codon may be mutated by an insertion or deletion frameshift mutation.

In a preferred embodiment the ptr gene is mutated to change the ATG start codon to ATT, as shown in FIG. 11a.

The knockout mutated ptr gene may alternatively or additionally comprise one or more stop codons positioned downstream of the gene start codon and upstream of the gene stop codon. Preferably the knockout mutated ptr gene comprises both a missense mutation to the start codon and one or more inserted stop codons.

The one or more inserted stop codons are preferably in-frame stop codons. However the one or more inserted stop codons may alternatively or additionally be out-of-frame stop codons. One or more out-of-frame stop codons may be required to stop translation where an out-of-frame start codon is changed to an in-frame start codon by an insertion or deletion frameshift mutation. The one or more stop codons may be introduced by any suitable mutation including a nonsense point mutation and a frameshift mutation. The one or more stop codons are preferably introduced by a frameshift mutation and/or an insertion mutation, preferably by replacement of a segment of the gene sequence with a sequence comprising a stop codon. For example an Ase I restriction site may be inserted, which comprises the stop codon TAA.

In a preferred embodiment the ptr gene is mutated to insert an in-frame stop codon by insertion of an Ase I restriction site, as shown in FIG. 11a. In a preferred embodiment the knockout mutated ptr gene has the DNA sequence of SEQ ID NO: 6. The mutations which have been made in the knockout mutated ptr gene sequence of SEQ ID NO: 6 are shown in FIG. 11a.

The above described knockout mutations are advantageous because they cause minimal or no disruption to the chromosomal DNA upstream or downstream of the target knockout gene site and do not require the insertion and retention of foreign DNA, such as antibiotic resistance markers, which may affect the cell's suitability for expressing a protein of interest, particularly therapeutic proteins. Accordingly, one or more of the cells according to the present invention may exhibit improved growth characteristics and/or protein expression compared to cells wherein the protease gene has been knocked out by insertion of foreign DNA into the gene coding sequence.

In one embodiment the cells according to the present invention carry a mutated OmpT gene. As used herein, "OmpT gene" means a gene encoding protease OmpT (outer membrane protease T) which is an outer membrane protease. The sequence of the wild-type non-mutated OmpT gene is SWISS-PROT P09169.

Reference to a mutated OmpT gene or mutated OmpT gene encoding OmpT, refers to either a mutated OmpT gene encoding a OmpT protein having reduced protease activity or a knockout mutated OmpT gene, unless otherwise indicated.

The expression "mutated OmpT gene encoding a OmpT protein having reduced protease activity" in the context of the present invention means that the mutated OmpT gene does not have the full protease activity compared to the wild-type non-mutated OmpT gene. The mutated OmpT gene may encode a OmpT protein having 50% or less, 40% or less, 30% or less, 20% or less, 10% or less or 5% or less of the protease activity of a wild-type non-mutated OmpT protein. The mutated OmpT gene may encode a OmpT protein having no protease activity. In this embodiment the cell is not deficient in chromosomal OmpT i.e. the OmpT gene sequence has not been deleted or mutated to prevent expression of any form of OmpT protein.

Any suitable mutation may be introduced into the OmpT gene in order to produce a protein having reduced protease activity. The protease activity of a OmpT protein expressed from a gram-negative bacterium may be easily tested by a person skilled in the art by any suitable method in the art, such as the method described in Kramer et al (Identification of essential acidic residues of outer membrane protease OmpT supports a novel active site, FEBS Letters 505 (2001) 426-430) and Dekker et al (Substrate Specificity of the Integral Membrane Protease OmpT Determined by Spatially Addressed Peptide Libraries, Biochemistry 2001, 40, 1694-1701).

OmpT has been reported in Kramer et al (Identification of active site serine and histidine residues in *Escherichia coli* outer membrane protease OmpT FEBS Letters 2000 468, 220-224) discloses that substitution of serines, histidines and acidic residues by alanines results in ~10-fold reduced activity for Glu27, Asp97, Asp208 or His101, ~500-fold reduced activity for Ser99 and ~10000-fold reduced activity for Asp83, Asp85, Asp210 or His212. Vandeputte-Rutten et al (Crystal Structure of the Outer Membrane Protease OmpT from *Escherichia coli* suggests a novel catalytic site, The EMBO Journal 2001, Vol 20 No 18 5033-5039) as having an active site comprising a Asp83-Asp85 pair and a His212-Asp210 pair. Further Kramer et al (Lipopolysaccharide regions involved in the activation of *Escherichia coli* outer membrane protease OmpT, Eur. J. Biochem. FEBS 2002, 269, 1746-1752) discloses that mutations D208A, D210A, H212A, H212N, H212Q, G216K/K217G, K217T and R218L in loop L4 all resulted in partial or virtually complete loss of enzymatic activity.

Accordingly, the OmpT mutation to produce a protein having reduced protease activity may comprise a mutation, such as a missense mutation to one or more of residues E27, D43, D83, D85, D97, S99, H101 E111, E136, E193, D206, D208, D210, H212 G216, K217, R218 & E250.

One or more of E27, D43, D83, D85, D97, S99, H101 E111, E136, E193, D206, D208, D210, H212 G216, K217, R218 & E250 may be mutated to any suitable amino acid which results in a protein having reduced protease activity. For example, one of more of E27, D43, D83, D85, D97, S99, H101 E111, E136, E193, D206, D208, D210, H212 G216, K217, R218 & E250 may be mutated to alanine. Examples of suitable mutations are E27A, D43A, D83A, D85A, D97A, S99A, H101A E111A, E136A, E193A, D206A, D208A, D210A, H212A, H212N, H212Q, G216K, K217G, K217T, R218L & E250A. In one embodiment the mutated OmpT gene comprises D210A and H212A mutations. A suitable mutated OmpT sequence comprising D210A and H212A mutations is shown in SEQ ID NO: 23.

The expression "knockout mutated OmpT gene" in the context of the present invention means that the gene comprises one or more mutations thereby causing no expression of the protein encoded by the gene to provide a cell deficient in the protein encoded by the knockout mutated gene. The knockout gene may be partially or completely transcribed but not translated into the encoded protein. The knockout mutated OmpT gene may be mutated in any suitable way, for example by one or more deletion, insertion, point, missense, nonsense and frameshift mutations, to cause no expression of the protein. For example, the gene may be knocked out by insertion of a foreign DNA sequence, such as an antibiotic resistance marker, into the gene coding sequence.

In one embodiment the OmpT gene comprises a mutation to the gene start codon and/or one or more stop codons positioned downstream of the gene start codon and upstream of the gene stop codon thereby preventing expression of the OmpT protein. The mutation to the start codon may be a missense mutation of one, two or all three of the nucleotides of the start codon. A suitable mutated knockout OmpT sequence is shown in SEQ ID NO: 24. Alternatively or additionally the start codon may be mutated by an insertion or deletion frameshift mutation.

In one embodiment the gram-negative bacterial cell according to the present invention does not carry a knockout mutated ompT gene, such as being deficient in chromosomal ompT.

In one embodiment the gram-negative bacterial cell according to the present invention does not carry a knockout mutated degP gene, such as being deficient in chromosomal degP. In one embodiment the gram-negative bacterial cell according to the present invention does not carry a mutated degP gene.

In one embodiment the gram-negative bacterial cell according to the present invention does not carry a knockout mutated ptr gene, such as being deficient in chromosomal ptr.

Many genetically engineered mutations including knockout mutations involve the use of antibiotic resistance markers which allow the selection and identification of successfully mutated cells. However, as discussed above, there are a number of disadvantages to using antibiotic resistance markers.

A further embodiment of the present invention overcomes the above disadvantages of using antibiotic resistance markers wherein the mutated Tsp gene, the mutated spr gene and optionally the mutated DegP gene and/or a mutated ptr gene and/or a mutated OmpT gene, are mutated to comprise one or more restriction marker sites. The restriction sites are genetically engineered into the gene and are non-naturally occurring. The restriction marker sites are advantageous because they allow screening and identification of correctly modified cells which comprise the required chromosomal mutations. Cells which have been modified to carry one or more of the mutated protease genes may be analyzed by PCR of genomic DNA from cell lysates using oligonucleotide pairs designed to amplify a region of the genomic DNA comprising a non-naturally occurring restriction marker site. The amplified DNA may then be analyzed by agarose gel electrophoresis before and after incubation with a suitable restriction enzyme capable of digesting the DNA at the non-naturally occurring restriction marker site. The presence of DNA fragments after incubation with the restriction enzyme confirms that the cells have been successfully modified to carry the one or more mutated genes.

In the embodiment wherein the cell carries a knockout mutated ptr gene having the DNA sequence of SEQ ID NO: 6, the oligonucleotide primer sequences shown in SEQ ID NO: 17 and SEQ ID NO:18 may be used to amplify the region of the DNA comprising the non-naturally occurring Ase I restriction site from the genomic DNA of transformed cells. The amplified genomic DNA may then be incubated with Ase I restriction enzyme and analyzed by gel electrophoresis to confirm the presence of the mutated ptr gene in the genomic DNA.

In the embodiment wherein the cell comprises a knockout mutated Tsp gene having the DNA sequence of SEQ ID NO: 3 or nucleotides 7 to 2048 of SEQ ID NO:3, the oligonucleotide primer sequences shown in SEQ ID NO: 15 and SEQ ID NO:16 may be used to amplify the region of the DNA comprising the non-naturally occurring Ase I restriction site from the genomic DNA of transformed cells. The amplified genomic DNA may then be incubated with Ase I restriction enzyme and analyzed by gel electrophoresis to confirm the presence of the mutated Tsp gene in the genomic DNA.

In the embodiment wherein the cell comprises a mutated DegP gene having the DNA sequence of SEQ ID NO: 9, the oligonucleotide primer sequences shown in SEQ ID NO: 19 and SEQ ID NO:20 may be used to amplify the region of the DNA comprising the non-naturally occurring Ase I restriction site from the genomic DNA of transformed cells. The amplified genomic DNA may then be incubated with Ase I restriction enzyme and analyzed by gel electrophoresis to confirm the presence of the mutated DegP gene in the genomic DNA.

The one or more restriction sites may be introduced by any suitable mutation including by one or more deletion, insertion, point, missense, nonsense and frameshift mutations. A restriction site may be introduced by the mutation of the start codon and/or mutation to introduce the one or more stop codons, as described above. This embodiment is advantageous because the restriction marker site is a direct and unique marker of the knockout mutations introduced.

A restriction maker site may be inserted which comprises an in-frame stop codon, such as an Ase I restriction site. This is particularly advantageous because the inserted restriction site serves as both a restriction marker site and a stop codon to prevent full transcription of the gene coding sequence. For example, in the embodiment wherein a stop codon is introduced to the ptr gene by introduction of an Ase I site, this also creates a restriction site, as shown in FIG. 11a. For example, in the embodiment wherein a stop codon is introduced to the Tsp gene at codon 21 by introduction of an Ase I site, this also creates a restriction site, as shown in FIG. 11b.

A restriction marker site may be inserted by the mutation to the start codon and optionally one or more further point mutations. In this embodiment the restriction marker site is preferably an EcoR I restriction site. This is particularly advantageous because the mutation to the start codon also creates a restriction marker site. For example, in the embodiment wherein the start codon of the ptr gene is changed to ATT, this creates an EcoR I marker site, as shown in FIG. 11a. For example, in the embodiment wherein the start codon (codon 3) of the Tsp gene is changed from ATG to TCG, as shown in FIG. 1b, a further point mutation of codon 2 from AAC to AAT and mutation of codon 3 ATG to TCG creates an EcoR I restriction marker site, as shown in FIG. 11b.

In the embodiment of the present invention wherein the cell carries a mutated OmpT gene, the one or more restriction sites may be introduced by any suitable mutation including by one or more deletion, insertion, point, missense, nonsense and frameshift mutations. For example, in the embodiment wherein the OmpT gene comprises the mutations D210A and H212A, these mutations introduce silent HindIII restriction site which may be used as a selection marker.

In the DegP gene or the spr gene, a marker restriction site may be introduced using silent codon changes. For example, an Ase I site may be used as a silent restriction marker site, wherein the TAA stop codon is out-of-frame, as shown in FIG. 11c for the mutated DegP gene.

In the embodiments of the present invention, wherein the ptr gene and/or the Tsp gene are mutated to encode a Protease III or Tsp having reduced protease activity, one or more marker restriction sites may be introduced using silent codon changes.

The recombinant gram-negative bacterial cell according to the present invention may be produced by any suitable means. The skilled person knows of suitable techniques which may be used to replace a chromosomal gene sequence with a mutated gene sequence. Suitable vectors may be employed which allow integration into the host chromosome by homologous recombination.

Suitable gene replacement methods are described, for example, in Hamilton et al (New Method for Generating Deletions and Gene Replacements in *Escherichia coli*, Hamilton C. M. et al., Journal of Bacteriology September 1989, Vol. 171, No. 9 p 4617-4622), Skorupski et al (Positive selection vectors for allelic exchange, Skorupski K and Taylor R. K., Gene, 1996, 169, 47-52), Kiel et al (A general method for the construction of *Escherichia coli* mutants by homologous recombination and plasmid segregation, Kiel J. A. K. W. et al, Mol Gen Genet. 1987, 207:294-301), Blomfield et al (Allelic exchange in *Escherichia coli* using the *Bacillus subtilis* sacB gene and a temperature sensitive pSC101 replicon, Blomfield I. C. et al., Molecular Microbiology 1991, 5(6), 1447-1457) and Ried et al. (An nptI-sacB-sacR cartridge for constructing directed, unmarked mutations in Gram-negative bacteria by marker exchange-eviction mutagenesis, Ried J. L. and Collmer A., Gene 57 (1987) 239-246). A suitable plasmid which enables homologous recombination/replacement is the pKO3 plasmid (Link et al., 1997, *Journal of Bacteriology*, 179, 6228-6237).

Successfully mutated strains may be identified using methods well known in the art including colony PCR DNA sequencing and colony PCR restriction enzyme mapping.

In the embodiment wherein the cell comprises two or more mutated chromosomal genes, the mutated genes may be introduced into the gram-negative bacterium on the same or different vectors.

In one embodiment the gram-negative bacterial cell according to the present invention does not carry a knockout mutated ompT gene, such as being deficient in chromosomal ompT.

The cell according to the present invention may further comprise a polynucleotide sequence encoding a protein of interest. The polynucleotide sequence encoding the protein of interest may be exogenous or endogenous. The polynucleotide sequence encoding the protein of interest may be integrated into the host's chromosome or may be non-integrated in a vector, typically a plasmid.

In one embodiment the cell according to the present invention expresses a protein of interest. "Protein of interest" in the context of the present specification is intended to refer to polypeptide for expression, usually a recombinant polypeptide. However, the protein of interest may be an endogenous protein expressed from an endogenous gene in the host cell.

As used herein, a "recombinant polypeptide" refers to a protein that is constructed or produced using recombinant DNA technology. The protein of interest may be an exogenous sequence identical to an endogenous protein or a mutated version thereof, for example with attenuated biological activity, or fragment thereof, expressed from an exogenous vector. Alternatively, the protein of interest may be a heterologous protein, not normally expressed by the host cell.

The protein of interest may be any suitable protein including a therapeutic, prophylactic or diagnostic protein.

In one embodiment the protein of interest is useful in the treatment of diseases or disorders including inflammatory diseases and disorders, immune disease and disorders, fibrotic disorders and cancers.

The term "inflammatory disease" or "disorder" and "immune disease or disorder" includes rheumatoid arthritis, psoriatic arthritis, still's disease, Muckle Wells disease, psoriasis, Crohn's disease, ulcerative colitis, SLE (Systemic Lupus Erythematosus), asthma, allergic rhinitis, atopic dermatitis, multiple sclerosis, vasculitis, Type I diabetes mellitus, transplantation and graft-versus-host disease.

The term "fibrotic disorder" includes idiopathic pulmonary fibrosis (IPF), systemic sclerosis (or scleroderma), kidney fibrosis, diabetic nephropathy, IgA nephropathy, hypertension, end-stage renal disease, peritoneal fibrosis (continuous ambulatory peritoneal dialysis), liver cirrhosis, age-related macular degeneration (ARMD), retinopathy, cardiac reactive fibrosis, scarring, keloids, burns, skin ulcers, angioplasty, coronary bypass surgery, arthroplasty and cataract surgery.

The term "cancer" includes a malignant new growth that arises from epithelium, found in skin or, more commonly, the lining of body organs, for example: breast, ovary, prostate, lung, kidney, pancreas, stomach, bladder or bowel. Cancers tend to infiltrate into adjacent tissue and spread (metastasise) to distant organs, for example: to bone, liver, lung or the brain.

The protein may be a proteolytically-sensitive polypeptide, i.e. proteins that are prone to be cleaved, susceptible to cleavage, or cleaved by one or more gram-negative bacterial, such as *E. coli*, proteases, either in the native state or during secretion. In one embodiment the protein of interest is proteolytically-sensitive to a protease selected from DegP, Protease III and Tsp. In one embodiment the protein of interest is proteolytically-sensitive to the protease Tsp. In one embodiment the protein of interest is proteolytically-sensitive to the proteases DegP and Protease III. In one embodiment the protein of interest is proteolytically sensitive to the proteases DegP and Tsp. In one embodiment the protein of interest is proteolytically-sensitive to the proteases Tsp and Protease III. In one embodiment the protein of interest is proteolytically sensitive to the proteases DegP, Protease III and Tsp.

Preferably the protein is a eukaryotic polypeptide.

The protein of interest expressed by the cells according to the invention may, for example be an immunogen, a fusion protein comprising two heterologous proteins or an antibody. Antibodies for use as the protein of interest include monoclonal, multi-valent, multi-specific, humanized, fully human or chimeric antibodies. The antibody can be from any species but is preferably derived from a monoclonal antibody, a human antibody, or a humanized fragment. The antibody can be derived from any class (e.g. IgG, IgE, IgM, IgD or IgA) or subclass of immunoglobulin molecule and may be obtained from any species including for example mouse, rat, shark, rabbit, pig, hamster, camel, llama, goat or human. Parts of the antibody fragment may be obtained from more than one species for example the antibody fragments may be chimeric. In one example the constant regions are from one species and the variable regions from another.

The antibody may be a complete antibody molecule having full length heavy and light chains or a fragment thereof, e.g. VH, VL, VHH, Fab, modified Fab, Fab', F(ab')$_2$, Fv, scFv fragment, Fab-Fv, or a dual specificity antibody, such as a Fab-dAb, as described in PCT/GB2008/003331.

The antibody may be specific for any target antigen. The antigen may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as (31 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD40L, CD45, CDW52, CD69, CD134 (OX40), ICOS, BCMP7, CD137, CD27L, CDCP1, CSF1 or CSF1-Receptor, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, KDR and VEGF, and where appropriate, receptors thereof.

Soluble antigens include interleukins such as IL-1, IL-2, IL-3, IL-4, IL-5, IL-6, IL-8, IL-12, IL-13, IL-14, IL-16 or IL-17, such as IL17A and/or IL17F, viral antigens for example respiratory syncytial virus or cytomegalovirus antigens, immunoglobulins, such as IgE, interferons such as interferon α, interferon β or interferon γ, tumour necrosis factor TNF (formerly known as tumour necrosis factor-α), tumor necrosis factor-β, colony stimulating factors such as G-CSF or GM-CSF, and platelet derived growth factors such as PDGF-α, and PDGF-β and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In one embodiment, the antibody may be used to functionally alter the activity of the antigen of interest. For example, the antibody may neutralize, antagonize or agonise the activity of said antigen, directly or indirectly.

The present invention also provides a recombinant gram-negative bacterial cell comprising a mutated Tsp gene, wherein the mutated Tsp gene encodes a Tsp protein having reduced protease activity or is a knockout mutated Tsp gene, a mutant spr gene encoding a mutant spr and a polynucleotide sequence encoding an antibody or an antigen binding fragment thereof specific for TNF.

In a preferred embodiment the protein of interest expressed by the cells according to the present invention is an anti-TNF antibody, more preferably an anti-TNF Fab', as described in WO01/094585 (the contents of which are incorporated herein by reference).

In a one embodiment the antibody having specificity for human TNFα, comprises a heavy chain wherein the variable domain comprises a CDR having the sequence shown in SEQ ID NO:26 for CDRH1, the sequence shown in SEQ ID NO:27 or SEQ ID NO:32 for CDRH2 or the sequence shown in SEQ ID NO:28 for CDRH3.

In one embodiment the antibody comprises a light chain wherein the variable domain comprises a CDR having the sequence shown in SEQ ID NO:29 for CDRL1, the sequence shown in SEQ ID NO:30 for CDRL2 or the sequence shown in SEQ ID NO:31 for CDRL3.

The CDRs given in SEQ IDS NOS:26 and 28 to 32 referred to above are derived from a mouse monoclonal antibody hTNF40. However, SEQ ID NO:27 consists of a hybrid CDR. The hybrid CDR comprises part of heavy chain CDR2 from mouse monoclonal antibody hTNF40 (SEQ ID NO:32) and part of heavy chain CDR2 from a human group 3 germline V region sequence.

In one embodiment the antibody comprises a heavy chain wherein the variable domain comprises a CDR having the sequence shown in SEQ ID NO:26 for CDRH1, the sequence shown in SEQ ID NO:27 or SEQ ID NO:32 for CDRH2 or the sequence shown in SEQ ID NO:28 for CDRH3 and a light chain wherein the variable domain comprises a CDR having the sequence shown in SEQ ID NO:29 for CDRL1, the sequence shown in SEQ ID NO:30 for CDRL2 or the sequence shown in SEQ ID NO:31 for CDRL3.

In one embodiment the antibody comprises SEQ ID NO:26 for CDRH1, SEQ ID NO: 27 or SEQ ID NO:32 for CDRH2, SEQ ID NO:28 for CDRH3, SEQ ID NO:29 for CDRL1, SEQ ID NO:30 for CDRL2 and SEQ ID NO:31 for CDRL3. Preferably the antibody comprises SEQ ID NO:27 for CDRH2.

The anti-TNF antibody is preferably a CDR-grafted antibody molecule. In a preferred embodiment the variable domain comprises human acceptor framework regions and non-human donor CDRs.

Preferably the antibody molecule has specificity for human TNF (formerly known as TNFα), wherein the light chain comprises the light chain variable region of SEQ ID NO: 11 and the heavy chain comprises the heavy chain variable region of SEQ ID NO: 12.

The anti-TNF antibody is preferably a Fab or Fab' fragment.

Preferably the antibody molecule having specificity for human TNF is a Fab' and has a light chain sequence comprising or consisting of SEQ ID NO: 13 and a heavy chain sequence comprising or consisting of SEQ ID NO: 14.

After expression, antibody fragments may be further processed, for example by conjugation to another entity such as an effector molecule.

The term effector molecule as used herein includes, for example, antineoplastic agents, drugs, toxins (such as enzymatically active toxins of bacterial or plant origin and fragments thereof e.g. ricin and fragments thereof) biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy. Effector molecular may be attached to the antibody or fragment thereof by any suitable method, for example an antibody fragment may be modified to attach at least one effector molecule as described in WO05/003171 or WO05/003170 (the contents of which are incorporated herein by reference). WO05/003171 or WO05/003170 also describe suitable effector molecules.

In one embodiment the antibody or fragment thereof, such as a Fab, is PEGylated to generate a product with the required properties, for example similar to the whole antibodies, if required. For example, the antibody may be a PEGylated anti-TNF-α Fab', as described in WO01/094585, preferably having attached to one of the cysteine residues at the C-terminal end of the heavy chain a lysyl-maleimide-derived group wherein each of the two amino groups of the lysyl residue has covalently linked to it a methoxypoly(ethyleneglycol) residue having a molecular weight of about 20,000 Da, such that the total average molecular weight of the methoxypoly(ethyleneglycol) residues is about 40,000 Da, more preferably the lysyl-maleimide-derived group is [1-[[[2-[[3-(2,5-dioxo-1-pyrrolidinyl)-1-oxopropyl]amino]ethyl]amino]-carbonyl]-1,5-pentanediyl]bis(iminocarbonyl).

The cell may also comprise further polynucleotide sequences encoding one or more further proteins of interest.

In one embodiment one or more *E. coli* host proteins that in the wild type are known to co-purify with the recombinant protein of interest during purification are selected for genetic modification, as described in Humphreys et al. "Engineering of *Escherichia coli* to improve the purification of periplasmic Fab' fragments: changing the pI of the chromosomally encoded PhoS/PstS protein", Protein Expression and Purification 37 (2004) 109-118 and WO04/035792 (the contents of which are incorporated herein by reference). The use of such modified host proteins improves the purification process for proteins of interest, especially antibodies, produced in *E. coli* by altering the physical properties of selected *E. coli* proteins so they no longer co-purify with the recombinant antibody. Preferably the *E. coli* protein that is altered is selected from one or more of Phosphate binding protein (PhoS/PstS), Dipeptide binding protein (DppA), Maltose binding protein (MBP) and Thioredoxin.

In one embodiment a physical property of a contaminating host protein is altered by the addition of an amino acid tag to the C-terminus or N-terminus. In a preferred embodiment the physical property that is altered is the isoelectric point and the amino acid tag is a poly-aspartic acid tag attached to the C-terminus. In one embodiment the *E. coli* proteins altered by the addition of said tag are Dipeptide binding protein (DppA), Maltose binding protein (MBP), Thioredoxin and Phosphate binding protein (PhoS/PstS). In one specific embodiment the pI of the *E. coli* Phosphate binding protein (PhoS/PstS) is reduced from 7.2 to 5.1 by the addition of a poly-aspartic acid tag (polyD), containing 6 aspartic acid residues to the C-terminus.

Also preferred is the modification of specific residues of the contaminating *E. coli* protein to alter its physical properties, either alone or in combination with the addition of N or C terminal tags. Such changes can include insertions or deletions to alter the size of the protein or amino acid substitutions to alter pI or hydrophobicity. In one embodiment these residues are located on the surface of the protein. In a preferred embodiment surface residues of the PhoS protein are altered in order to reduce the pI of the protein. Preferably residues that have been implicated to be important in phosphate binding (Bass, U.S. Pat. No. 5,304,472) are avoided in order to maintain a functional PhoS protein. Preferably lysine residues that project far out of the surface of the protein or are in or near large groups of basic residues are targeted. In one embodiment, the PhoS protein has a hexa poly-aspartic acid tag attached to the C-terminus whilst surface residues at the opposite end of the molecule are targeted for substitution. Preferably selected lysine residues are substituted for glutamic acid or aspartic acid to confer a greater potential pI change than when changing neutral residues to acidic ones. The designation for a substitution mutant herein consists of a letter followed by a number followed by a letter. The first letter designates the amino acid in the wild-type protein. The number refers to the amino acid position where the amino acid substitution is being made, and the second letter designates the amino acid that is used to replace the wild-type amino acid. In preferred mutations of PhoS in the present invention lysine residues (K) 275, 107, 109, 110, 262, 265, 266, 309, 313 are substituted for glutamic acid (E) or glutamine (Q), as single or combined mutations, in addition lysine(K)318 may be substituted for aspartic acid (D) as a single or combined mutation. Preferably the single mutations are K262E, K265E and K266E. Preferably the combined mutations are K265/266E and K110/265/266E. More preferably, all mutations are combined with the polyaspartic acid (polyD) tag attached at the C-terminus and optionally also with the K318D substitution. In a preferred embodiment the mutations result in a reduction in pI of at least 2 units. Preferably the mutations of the present invention reduce the pI of PhoS from 7.2 to between about 4 and about 5.5. In one embodiment of the present invention the pI of the PhoS protein of *E. coli* is reduced from 7.2 to about 4.9, about 4.8 and about 4.5 using the mutations polyD K318D, polyD K265/266E and polyD K110/265/266E respectively.

The polynucleotide encoding the protein of interest may be expressed as a fusion with another polypeptide, preferably a signal sequence or other polypeptide having a specific cleavage site at the N-terminus of the mature polypeptide. The heterologous signal sequence selected should be one that is recognized and processed by the host cell. For prokaryotic host cells that do not recognize and process the native or a eukaryotic polypeptide signal sequence, the signal sequence is substituted by a prokaryotic signal sequence. Suitable signal sequences include OmpA, PhoA, LamB, PelB, DsbA and DsbC.

Construction of suitable vectors containing one or more of the above-listed components employs standard ligation techniques. Isolated plasmids or DNA fragments are cleaved, tailored, and re-ligated in the form desired to generate the plasmids required.

In one embodiment an expression cassette is employed in the present invention to carry the polynucleotide encoding the protein of interest which typically comprises one or more protein coding sequences encoding one or more proteins of interest and one or more regulatory expression sequences. The one or more regulatory expression sequences may include a promoter. The one or more regulatory expression sequences may also include a 3' untranslated region such as a termination sequence. Suitable promoters are discussed in more detail below.

In one embodiment, the cell according to the present invention comprises a vector, such as plasmid. The vector preferably comprises one or more of the expression cassettes as defined above.

In the embodiment where the protein of interest is an antibody comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The vector for use in the present invention may be produced by inserting an expression cassette as defined above into a suitable vector. Alternatively, the regulatory expression sequences for directing expression of the polynucleotide sequence encoding a protein of interest may be contained in the vector and thus only the encoding region of the polynucleotide may be required to complete the vector.

Examples of vectors which may be employed to transform the host cell with a polynucleotide according to the invention include:

a plasmid, such as pBR322 or pACYC184, and/or
a viral vector such as bacterial phage
a transposable genetic element such as a transposon Many forms of expression vector are available. Such vectors usually comprise a plasmid origin of DNA replication, an antibiotic selectable marker a promoter and transcriptional terminator separated by a multi-cloning site (expression cassette) and a DNA sequence encoding a ribosome binding site.

The promoters employed in the present invention can be linked to the relevant polynucleotide directly or alternatively be located in an appropriate position, for example in a vector such that when the relevant polypeptide is inserted the relevant promoter can act on the same. In one embodiment the promoter is located before the encoding portion of the polynucleotide on which it acts, for example a relevant promoter before each encoding portion of polynucleotide. "Before" as used herein is intended to imply that the promoter is located at the 5 prime end in relation to the encoding polynucleotide portion.

The promoters may be endogenous or exogenous to the host cells. Suitable promoters include Lac, tac, trp, PhoA, Ipp, Arab, Tet and T7.

One or more promoters employed may be inducible promoters.

Expression units for use in bacterial systems also generally contain a Shine-Dalgarno (S. D.) ribosome sequence operably linked to the DNA encoding the polypeptide of interest.

In the embodiments of the present invention wherein a polynucleotide sequence comprises two or more encoding sequences for two or more proteins of interest, for example an antibody light chain and antibody heavy chain, the polynucleotide sequence may comprise one or more internal ribosome entry site (IRES) sequences which allows translation initiation in the middle of an mRNA. An IRES sequence may be positioned between encoding polynucleotide sequences to enhance separate translation of the mRNA to produce the encoded polypeptide sequences.

The expression vector preferably also comprises a dicistronic message for producing the antibody or antigen binding fragment thereof as described in WO 03/048208 or WO2007/039714 (the contents of which are incorporated herein by reference). Preferably the upstream cistron contains DNA coding for the light chain of the antibody and the downstream cistron contains DNA coding for the corresponding heavy chain, and the dicistronic intergenic sequence (IGS) preferably comprises a sequence selected from IGS1 (SEQ ID NO: 34), IGS2 (SEQ ID NO: 35), IGS3 (SEQ ID NO: 36) and IGS4 (SEQ ID NO: 37).

The terminators may be endogenous or exogenous to the host cells. A suitable terminator is rrnB.

Further suitable transcriptional regulators including promoters and terminators and protein targeting methods may be found in "Strategies for Achieving High-Level Expression of Genes in *Escherichia coli*" Savvas C. Makrides, Microbiological Reviews, September 1996, p 512-538.

The antibody molecule may be secreted from the cell or targeted to the periplasm by suitable signal sequences. Alternatively, the antibody molecules may accumulate within the cell's cytoplasm. Preferably the antibody molecule is targeted to the periplasm.

Embodiments of the invention described herein with reference to the polynucleotide apply equally to alternative embodiments of the invention, for example vectors, expression cassettes and/or host cells comprising the components employed therein, as far as the relevant aspect can be applied to same.

According to a third aspect of the present invention there is provided a method for producing a recombinant protein of interest comprising expressing the recombinant protein of interest in a recombinant gram-negative bacterial cell as described above in the first or second aspect of the present invention.

The gram negative bacterial cell and protein of interest preferably employed in the method of the present invention are described in detail above.

When the polynucleotide encoding the protein of interest is exogenous the polynucleotide may be incorporated into the host cell using any suitable means known in the art. Typically, the polynucleotide is incorporated as part of an expression vector which is transformed into the cell. Accordingly, in one aspect the cell according to the present invention comprises an expression cassette comprising the polynucleotide encoding the protein of interest.

The polynucleotide sequence can be transformed into a cell using standard techniques, for example employing rubidium chloride, PEG or electroporation.

The method according to the present invention may also employ a selection system to facilitate selection of stable cells which have been successfully transformed with the polynucleotide encoding the protein of interest. The selection system typically employs co-transformation of a polynucleotide sequence encoding a selection marker. In one embodiment, each polynucleotide transformed into the cell further comprises a polynucleotide sequence encoding one or more selection markers. Accordingly, the transformation of the polynucleotide encoding the protein of interest and the one or more polynucleotides encoding the marker occurs together and the selection system can be employed to select those cells which produce the desired proteins.

Cells able to express the one or more markers are able to survive/grow/multiply under certain artificially imposed conditions, for example the addition of a toxin or antibiotic, because of the properties endowed by the polypeptide/gene or polypeptide component of the selection system incorporated therein (e.g. antibiotic resistance). Those cells that cannot express the one or more markers are not able to survive/grow/multiply in the artificially imposed conditions. The artificially imposed conditions can be chosen to be more or less vigorous, as required.

Any suitable selection system may be employed in the present invention. Typically the selection system may be based on including in the vector one or more genes that provides resistance to a known antibiotic, for example a tetracycline, chloramphenicol, kanamycin or ampicillin resistance gene. Cells that grow in the presence of a relevant antibiotic can be selected as they express both the gene that gives resistance to the antibiotic and the desired protein.

In one embodiment, the method according to the present invention further comprises the step of culturing the transformed cell in a medium to thereby express the protein of interest.

An inducible expression system or a constitutive promoter may be used in the present invention to express the protein of interest. Suitable inducible expression systems and constitutive promoters are well known in the art.

Any suitable medium may be used to culture the transformed cell. The medium may be adapted for a specific selection system, for example the medium may comprise an antibiotic, to allow only those cells which have been successfully transformed to grow in the medium.

The cells obtained from the medium may be subjected to further screening and/or purification as required. The method may further comprise one or more steps to extract and purify the protein of interest as required.

The polypeptide may be recovered from the strain, including from the cytoplasm, periplasm, or supernatant.

The specific method (s) used to purify a protein depends on the type of protein. Suitable methods include fractionation on immuno-affinity or ion-exchange columns; ethanol precipitation; reversed-phase HPLC; hydrophobic-interaction chromatography; chromatography on silica; chromatography on an ion-exchange resin such as S-SEPHAROSE and DEAE; chromatofocusing; ammonium-sulfate precipitation; and gel filtration.

Antibodies may be suitably separated from the culture medium and/or cytoplasm extract and/or periplasm extract by conventional antibody purification procedures such as, for example, protein A-Sepharose, protein G chromatography, protein L chromatography, thiophilic, mixed mode resins, His-tag, FLAGTag, hydroxylapatite chromatography, gel electrophoresis, dialysis, affinity chromatography, Ammonium sulphate, ethanol or PEG fractionation/precipitation, ion exchange membranes, expanded bed adsorption chromatography (EBA) or simulated moving bed chromatography.

The method may also include a further step of measuring the quantity of expression of the protein of interest and selecting cells having high expression levels of the protein of interest.

The method may also including one or more further downstream processing steps such as PEGylation of the protein of interest, such as an antibody or antibody fragment.

One or more method steps described herein may be performed in combination in a suitable container such as a bioreactor.

EXAMPLES

Example 1

Generation Cell Strain MXE001 (ΔTsp)

The MXE001 strain was generated as follows:

The Tsp cassette was moved as Sal I, Not I restriction fragments into similarly restricted pKO3 plasmids. The pKO3 plasmid uses the temperature sensitive mutant of the pSC101 origin of replication (RepA) along with a chloramphenicol marker to force and select for chromosomal integration events. The sacB gene which encodes for levansucrase is lethal to *E. coli* grown on sucrose and hence (along with the chloramphenicol marker and pSC101 origin) is used to force and select for de-integration and plasmid curing events. This methodology had been described previously (Hamilton et al., 1989, *Journal of Bacteriology*, 171, 4617-4622 and Blomfield et al., 1991, *Molecular Microbiology*, 5, 1447-1457). The pKO3 system removes all selective markers from the host genome except for the inserted gene.

The following plasmids were constructed.

pMXE191 comprising the knockout mutated Tsp gene as shown in the SEQ ID NO: 3 comprising EcoR I and Ase I restriction markers.

The plasmid was then transformed into electro-competent competent *E. coli* W3110 cells prepared using the method found in Miller, E. M. and Nickoloff, J. A., "*Escherichia coli* electrotransformation," in Methods in Molecular Biology, vol. 47, Nickoloff, J. A. (ed.), Humana Press, Totowa, N.J., 105 (1995).

Day 1 40 μl of *E. coli* cells were mixed with (10 pg) 1 μl of pKO3 DNA in a chilled BioRad 0.2 cm electroporation cuvette before electroporation at 2500V, 25 μF and 200Ω. 1000 μl of 2×PY was added immediately, the cells recovered by shaking at 250 rpm in an incubator at 30° C. for 1 hour. Cells were serially 1/10 diluted in 2×PY before 100 μl aliquots were plated out onto 2×PY agar plates containing chloramphenicol at 20 μg/ml prewarmed at 30° C. and 43° C. Plates were incubated overnight at 30° C. and 43° C.

Day 2 The number of colonies grown at 30° C. gave an estimate of the efficiency of electroporation whilst colonies that survive growth at 43° C. represent potential integration events. Single colonies from the 43° C. plate were picked and resuspended in 10 ml of 2×PY. 100 μl of this was plated out onto 2×PY agar plates containing 5% (w/v) sucrose prewarmed to 30° C. to generate single colonies. Plates were incubated overnight at 30° C.

Day 3 Colonies here represent potential simultaneous de-integration and plasmid curing events. If the de-integration and curing events happened early on in the growth, then the bulk of the colony mass will be clonal. Single colonies were picked and replica plated onto 2×PY agar that contained either chloramphenicol at 20 μg/ml or 5% (w/v) sucrose. Plates were incubated overnight at 30° C.

Day 4 Colonies that both grow on sucrose and die on chloramphenicol represent potential chromosomal replacement and plasmid curing events. These were picked and screened by PCR with a mutation specific oligonucleotide. Colonies that generated a positive PCR band of the correct size were struck out to produce single colonies on 2×PY agar containing 5% (w/v) sucrose and the plates were incubated overnight at 30° C.

Day 5 Single colonies of PCR positive, chloramphenicol sensitive and sucrose resistant *E. coli* were used to make glycerol stocks, chemically competent cells and act as PCR templates for a PCR reaction with 5' and 3' flanking oligos to generate PCR product for direct DNA sequencing using Taq polymerase.

Cell strain MXE001 was tested to confirm successful modification of genomic DNA carrying the mutated Tsp gene by PCR amplification of the region of the Tsp gene comprising a non-naturally occurring Ase I restriction site, as shown in FIGS. 1a, 1b and 1c, using oligonucleotides primers. The amplified regions of the DNA were then analyzed by gel electrophoresis before and after incubation with Ase I restriction enzyme to confirm the presence of the non-naturally occurring Ase I restriction site in the mutated genes. This method was carried out as follows:

The following oligos were used to amplify, using PCR, genomic DNA from prepared *E. coli* cell lysates from MXE001 and W3110:

(SEQ ID NO: 15)
6284 Tsp 3'    5'-GCATCATAATTTTCTTTTTACCTC-3'

(SEQ ID NO: 16)
6283 Tsp 5'    5'-GGGAAATGAACCTGAGCAAAACGC-3'

The lysates were prepared by heating a single colony of cells for 10 minutes at 95° C. in 20 ul of 1×PCR buffer. The mixture was allowed to cool to room temperature then centrifugation at 13,200 rpm for 10 minutes. The supernatant was removed and labeled as 'cell lysate'.

Each strain was amplified using the Tsp oligos pair.

The DNA was amplified using a standard PCR procedure.

| | |
|---|---|
| 5 ul | Buffer ×10 (Roche) |
| 1 ul | dNTP mix (Roche, 10 mM mix) |
| 1.5 ul | 5' oligo (5 pmol) |
| 1.5 ul | 3' oligo (5 pmol) |
| 2 ul | Cell lysate |
| 0.5 ul | Taq DNA polymerase (Roche 5U/ul) |
| 38.5 ul | H2O |

PCR Cycle.

| 94° C. | 1 minute | |
| 94° C. | 1 minute | |
| 55° C. | 1 minute | repeated for 30 cycles |
| 72° C. | 1 minute | |
| 72° C. | 10 minutes | |

Once the reactions were complete 25 ul was removed to a new microfuge tube for digestion with Ase I. To the 25 ul of PCR reaction 19 ul of H2O, 5 ul of buffer 3 (NEB), 1 ul of Ase I (NEB) was added, mixed and incubated at 37° C. for 2 hours.

To the remaining PCR reaction 5 ul of loading buffer (×6) was added and 20 ul was loaded onto a 0.8% TAE 200 ml agarose gel (Invitrogen) plus Ethidium Bromide (5 ul of 10 mg/ml stock) and run at 100 volts for 1 hour. 10 ul of size marker (Perfect DNA marker 0.1-12 Kb, Novagen) was loaded in the final lane.

Once the Ase I digestions were complete 10 ul of loading buffer (×6) was added and 20 ul was loaded onto a 0.8% TAE agarose gel (Invitrogen) plus Ethidium Bromide (5 ul of 10 mg/ml stock) and run at 100 volts for 1 hour. 10 ul of size marker (Perfect DNA marker 0.1-12 Kb, Novagen) was loaded in the final lane. Both gels were visualized using UV transluminator.

The genomic fragment amplified showed the correct sized band of 2.8 Kb for Tsp. Following digestion with Ase I this confirmed the presence of the introduced Ase I sites in the Tsp deficient strain MXE001 but not in the W3110 control.

MXE001: genomic DNA amplified using the Tsp primer set and the resulting DNA was digested with Ase I to produce 2.2 and 0.6 Kbps bands.

W3110 PCR amplified DNA was not digested by Ase I restriction enzyme.

Example 2

Generation of spr Mutants

The spr mutations were generated and selected for using a complementation assay.

The spr gene was mutated using the Clontech® random mutagenesis diversity PCR kit which introduced 1 to 2 mutations per 1000 bp. The mutated spr PCR DNA was cloned into an inducible expression vector [pTTO CDP870] which expresses CDP870 Fab' along with the spr mutant. This ligation was then electro-transformed into an *E. coli* strain MXE001 (ΔTsp) prepared using the method found in Miller, E. M. and Nickoloff, J. A., "*Escherichia coli* electrotransformation," in Methods in Molecular Biology, vol. 47, Nickoloff, J. A. (ed.), Humana Press, Totowa, N.J., 105 (1995). The following protocol was used, 40 ul of electro competent MXE001, 2.5 ul of the ligation (100 pg of DNA) was added to a 0.2 cm electroporation cuvette, electro-transformation was performed using as BioRad Genepulser Xcell with the following conditions, 2500V, 25 µF and 200Ω. After the electro-transformation 1 ml of SOC (Invitrogen) (pre-warmed to 37° C.) was added and the cells left to recover at 37° C. for 1 hour with gentle agitation.

The cells where plated onto Hypotonic agar (5 g/L Yeast extract, 2.5 g/L Tryptone, 15 g/L Agar (all Difco)) and incubated at 40° C. Cells which formed colonies were re-plated onto HLB at 43° C. to confirm restoration of the ability to grow under low osmotic conditions at high temperature to the MXE001 strain. Plasmid DNA was prepared from the selected clones and sequenced to identify spr mutations.

Using this method eight single, one double mutation and two multiple mutations in the spr protein were isolated which complemented the ΔTsp phenotype as follows:
1. V98E
2. D133A
3. V135D
4. V135G
5. G147C
6. S95F and Y115F
7. I70T
8. N31T, Q73R, R100G, G140C
9. R62C, Q99P, R144C
10. L108S
11. L136P Example 3

Generation of Mutant *E. coli* Cell Strains Carrying spr Mutations

The individual mutations 1 to 5 identified in Example 2 and three catalytic triad mutations of spr (C94A, H145A, H157A) and W174R were used to generate new strains using either the wild-type W3110 *E. coli* strain (genotype: F-LAM-IN (rrnD-rrnE)1 rph1 (ATCC no. 27325)) to create spr mutated strains or MXE001 strain from Example 1 to make combined ΔTsp/mutant spr strains.

The following mutant *E. coli* cell strains were generated using a gene replacement vector system using the pKO3 homologous recombination/replacement plasmid (Link et al., 1997, *Journal of Bacteriology*, 179, 6228-6237), as described in Example 1 for the generation of MXE001.

TABLE 1

| Mutant *E. coli* Cell Strain | Genotype | Spr Vectors |
|---|---|---|
| MXE001 | ΔTsp | — |
| MXE008 | ΔTsp, spr D133A | pMXE339, pK03 spr D133A (-SalI) |
| MXE009 | ΔTsp, spr H157A | pMXE345, pK03 spr H157A (-SalI) |
| MXE010 | spr G147C | pMXE338, pK03 spr G147C (-SalI) |
| MXE011 | spr C94A | pMXE343, pK03 spr C94A (-SalI) |
| MXE012 | spr H145A | pMXE344, pK03 spr H145A (-SalI) |
| MXE013 | spr W174R | pMXE346, pK03 spr W174R (-SalI) |
| MXE014 | ΔTsp, spr V135D | pMXE340, pK03 spr V135D (-SalI) |
| MXE015 | ΔTsp, spr V98E | pMXE342, pK03 spr V98E (-SalI) |
| MXE016 | ΔTsp, spr C94A | pMXE343, pK03 spr C94A (-SalI) |
| MXE017 | ΔTsp, spr H145A | pMXE344, pK03 spr H145A (-SalI) |
| MXE018 | ΔTsp, spr V135G | pMXE341, pK03 spr V135G (-SalI) |

The mutant spr integration cassettes were moved as SalI, Not I restriction fragments into similarly restricted pKO3 plasmids.

The plasmid uses the temperature sensitive mutant of the pSC101 origin of replication (RepA) along with a chloramphenicol marker to force and select for chromosomal integration events. The sacB gene which encodes for levansucrase is lethal to *E. coli* grown on sucrose and hence (along with the chloramphenicol marker and pSC101 origin) is used to force and select for de-integration and plasmid curing events. This methodology had been described previously (Hamilton et al., 1989, *Journal of Bacteriology*, 171, 4617-4622 and Blomfield et al., 1991, *Molecular Microbiology*, 5, 1447-1457). The pKO3 system removes all selective markers from the host genome except for the inserted gene.

The pK03 vectors listed below were constructed, comprising the mutated spr genes including a silent mutation within the spr sequence which removes a SalI restriction site for clone identification.

pMXE336, pK03 spr S95F (−SalI)
pMXE337, pK03 spr Y115F (−SalI)
pMXE338, pK03 spr G147C (−SalI)
pMXE339, pK03 spr D133A (−SalI)
pMXE340, pK03 spr V135D (−SalI)
pMXE341, pK03 spr V135G (−SalI)
pMXE342, pK03 spr V98E (−SalI)
pMXE343, pK03 spr C94A (−SalI)
pMXE344, pK03 spr H145A (−SalI)
pMXE345, pK03 spr H157A (−SalI)
pMXE346, pK03 spr W174R (−SalI)

These plasmids were then transformed into chemically competent E. coli W3110 cells prepared using the method found in Miller, E. M. and Nickoloff, J. A., "Escherichia coli electrotransformation," in Methods in Molecular Biology, vol. 47, Nickoloff, J. A. (ed.), Humana Press, Totowa, N.J., 105 (1995) or into MXE001 strain from Example 1 to make combined ΔTsp/mutant spr strains, as shown in Table 1.

Day 1 40 μl of electro-competent E. coli cells or MXE001 cells were mixed with (10 pg) 1 μl of pKO3 DNA in a chilled BioRad 0.2 cm electroporation cuvette before electroporation at 2500V, 25 μF and 200Ω. 1000 μl of 2×PY was added immediately, the cells recovered by shaking at 250 rpm in an incubator at 30° C. for 1 hour. Cells were serially 1/10 diluted in 2×PY before 100 μl aliquots were plated out onto 2×PY agar plates containing chloramphenicol at 20 μg/ml pre-warmed at 30° C. and 43° C. Plates were incubated overnight at 30° C. and 43° C.

Day 2 The number of colonies grown at 30° C. gave an estimate of the efficiency of electroporation whilst colonies that survive growth at 43° C. represent potential integration events. Single colonies from the 43° C. plate were picked and resuspended in 10 ml of 2×PY. 100 μl of this was plated out onto 2×PY agar plates containing 5% (w/v) sucrose pre-warmed to 30° C. to generate single colonies. Plates were incubated overnight at 30° C.

Day 3 Colonies here represent potential simultaneous de-integration and plasmid curing events. If the de-integration and curing events happened early on in the growth, then the bulk of the colony mass will be clonal. Single colonies were picked and replica plated onto 2×PY agar that contained either chloramphenicol at 20 μg/ml or 5% (w/v) sucrose. Plates were incubated overnight at 30° C.

Day 4 Colonies that both grow on sucrose and die on chloramphenicol represent potential chromosomal replacement and plasmid curing events. These were picked and screened by PCR plus restriction digest for the loss of a SalI site. Colonies that generated a positive PCR band of the correct size and resistance to digestion by SalI were struck out to produce single colonies on 2×PY agar containing 5% (w/v) sucrose and the plates were incubated overnight at 30° C.

Day 5 Single colonies of PCR positive, chloramphenicol sensitive and sucrose resistant E. coli were used to make glycerol stocks, chemically competent cells and act as PCR templates for a PCR reaction with 5' and 3' flanking oligos to generate PCR product for direct DNA sequencing using $Tac_t$ polymerase to confirm the correct mutation.

Example 4

Expression of Anti-TNF Fab' in the spr Mutant Strains

The spr mutant strains MXE008, MXE009, MXE012 and MXE017 provided in Example 3 and the MXE001 strain provided in Example 1 were transformed with plasmid pMXE117 (pTTO CDP870 IGS2), an expression vector for the CDP870 Fab' (an anti-TNF Fab' having a light chain sequence shown in SEQ ID NO: 13 and a heavy chain sequence shown in SEQ ID NO: 14), was constructed using conventional restriction cloning methodologies which can be found in Sambrook et al 1989, Molecular cloning: a laboratory manual. CSHL press, N.Y. The plasmid pMXE117 (pTTO CDP870 or 40.4 IGS17) contained the following features; a strong tac promoter and lac operator sequence. The Fab light and heavy chain genes were transcribed as a single dicistronic message. DNA encoding the signal peptide from the E. coli OmpA protein was fused to the 5 end of both light and heavy chain gene sequences, which directed the translocation of the polypeptides to the E. coli periplasm. Transcription was terminated using a dual transcription terminator rrnB t1t2. The lacIq gene encoded the constitutively expressed Lac I repressor protein. This repressed transcription from the tac promoter until de-repression was induced by the presence of allolactose or IPTG. The origin of replication used was p15A, which maintained a low copy number. The plasmid contained a tetracycline resistance gene for antibiotic selection.

The transformation of the strains was carried out using the method found in Chung C. T et al Transformation and storage of bacterial cells in the same solution. PNAS 86:2172-2175 (1989).

Example 5

Expression of an Anti-TNFα Fab' in Mutated E. coli Strains Using Shake Flask Cultures Strains spr mutant strains MXE008, MXE009, MXE012 and MXE017 were tested in a shake flask experiment comparing growth and expression of an anti-TNFα Fab' against W3110 and MXE001.

The shake flask experimental protocol used was performed as follows:
5 ml Shake flask Experiment A single colony was picked into 5 ml LB plus tetracycline at 10 ug/ml and grown overnight at 30° C. with shaking at 250 rpm.

The overnight culture was use to inoculate 100 ml plus tetracycline to 0.1 OD600. (i.e. for OD of 4, 100/4×01=2.5 mls in 100 ml.)

3×5 ml culture tubes were set up for every time point required using this master culture. 1 reference culture was set up to sample for OD measurement.

The cultures were shaken at 30° C. 250 rpm monitoring growth visually at first, then by sampling the reference culture to catch cultures at 0.5 OD 600 (usually about 2 hrs). IPTG was added to each culture tube to a concentration of 200 uM (25 ul of 0.04M) once the culture had achieved an OD greater than 0.5.

The culture tubes were removed at the required time points e.g. 1 hr, 2 hr, post induction and kept on ice.

After centrifugation at 13,200 rpm for 5 minutes the cell pellet was re-suspended in 200 ul of periplasmic extraction buffer (100 mM Tris.Cl/10 mM EDTA pH 7.4). Periplasmic extracts were agitated at 250 rpm over night at 30° C. The next day, the extracts were centrifuged for 10 minutes at 13,200 rpm, the supernatant decanted off and stored at −20° C. as 'periplasmic extract'. The spent cell pellet was discarded.
ELISA Quantification.

96 well ELISA plates were coated overnight at 4° C. with AB141 (rabbit anti-human CH1, UCB) at 2 μgml-1 in PBS. After washing 3× with 300 ul of sample/conjugate buffer (PBS, BSA 0.2% (w/v), Tween 20 0.1% (v/v)), serial 1/2 dilutions of samples and standards were performed on the plate in 100 µl of sample/conjugate buffer, and the plate agitated at 250 r.p.m at room temperature for 1 hour. After washing 3× with 300 ul of wash buffer (PBS, Tween 20 0.1% (v/v)), 100 µl of the revealing antibody 6062 (rabbit anti-human kappa HRP conjugated, The Binding Site, Birmingham, U.K.) was added, after dilution at 1/1000 in sample/conjugate buffer. The plate was then agitated at 250 r.p.m at room temperature for 1 hour. After washing with 3×300 ul of wash buffer, 100 µl of TMB substrate was added (50:50 mix of TMB solution (Calbiochem): dH2O) and the $A_{630}$ recorded using an automated plate reader. The concentration of Fab' in the periplasmic extracts were calculated by comparison with purified Fab' standards of the appropriate isotype.

FIG. 1 shows improved growth of MXE008 and MXE009 compared to the wild type W3110 and MXE001.

Figure 2:
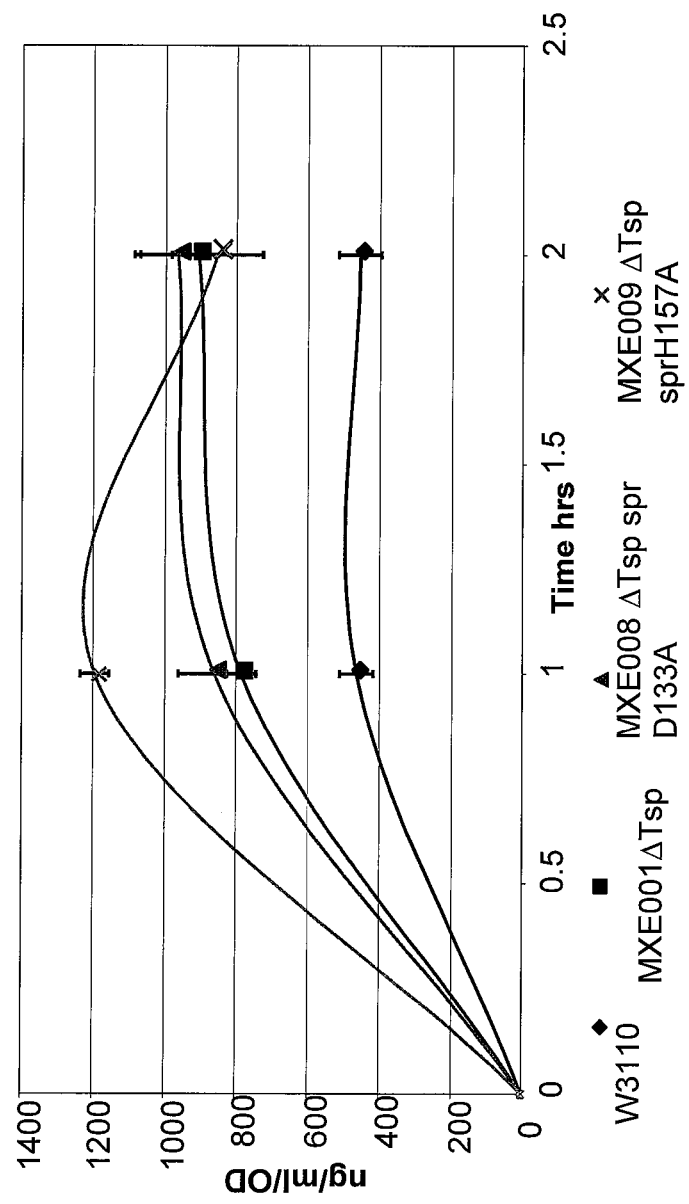
FIG. 2 shows the expression of anti-TNFα Fab' from MXE008 and MXE009 strains compared to the wild type W3110 and MXE001.

FIG. 2 shows improved expression of the Fab' from MXE008 and MXE009 strains compared to the wild type W3110 and MXE001.

Figure 5:
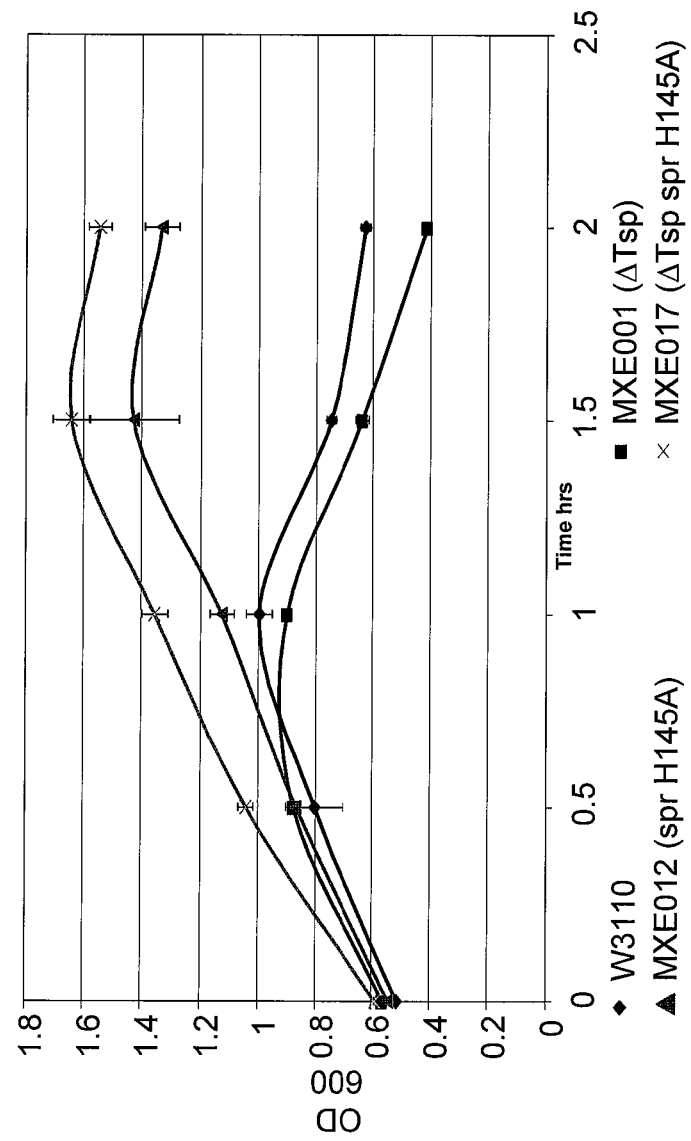
FIG. 5 shows the growth profile of anti-TNFα Fab' expressing strains MXE0012 and MXE017 compared to the anti-TNFα Fab' expressing strains wild-type W3110 and MXE001.

FIG. 5 shows the improved growth of MXE0012 and MXE017 compared to the wild-type W3110 and MXE001.

Figure 6:
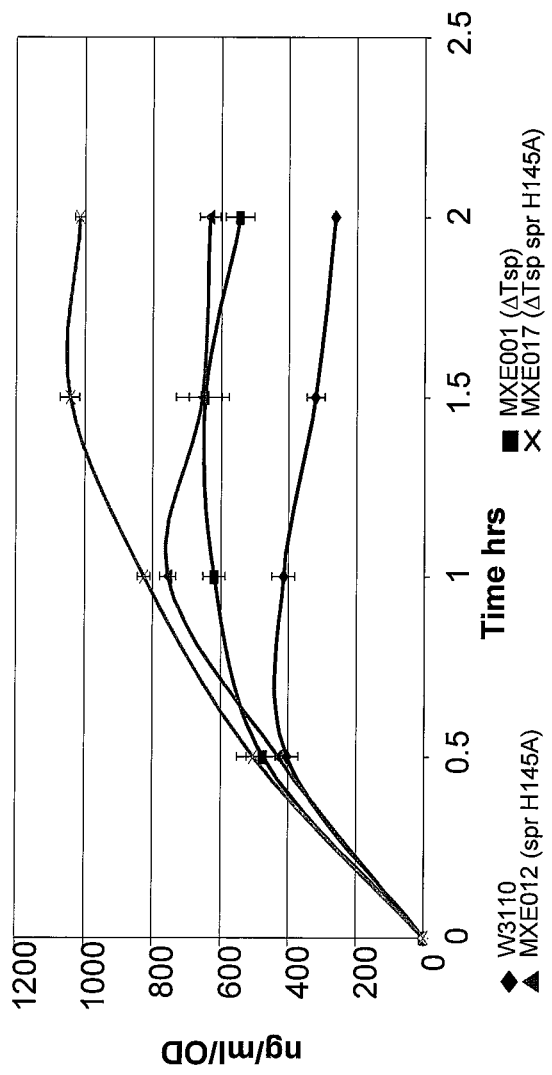
FIG. 6 shows the expression of anti-TNFα Fab' in MXE0012 and MXE017 compared to the wild-type W3110 and MXE001.

FIG. 6 shows improved expression of the Fab' in MXE0012 and MXE017 compared to the wild-type W3110 and MXE001.

Example 6

Growth of spr Mutated *E. coli* Strains and Expression of Fab' in Mutated *E. coli* Strains Using High Density Fermentations Strains MXE008, MXE009, MXE001 and wild type W3110 cells were transformed with plasmid pMXE117 tested in fermentation experiments comparing growth and expression of an anti-TNFα Fab'.

Growth Medium.

The fermentation growth medium was based on SM6E medium (described in Humphreys et al., 2002, Protein Expression and Purification, 26, 309-320) with 3.86 g/l $NaH_2PO_4.H_2O$ and 112 g/l glycerol.

Inoculum.

Inoculum cultures were grown in the same medium supplemented with 10 µg/ml tetracycline. Cultures were incubated at 30° C. with agitation for approximately 22 hours.

Fermentation.

Fermenters (2.5 liters total volume) were seeded with inoculum culture to 0.3-0.5 $OD_{600}$. Temperature was maintained at 30° C. during the growth phase and was reduced to 25° C. prior to induction. The dissolved oxygen concentration was maintained above 30% air saturation by variable agitation and airflow. Culture pH was controlled at 7.0 by automatic titration with 15% (v/v) $NH_4OH$ and 10% (v/v) conc. $H_2SO_4$. Foaming was controlled by the addition of 10% (v/v) Struktol J673 solution (Schill and Seilacher). A number of additions were made at different stages of the fermentation. When biomass concentration reached approximately 40 $OD_{600}$, magnesium salts and $NaH_2PO_4.H_2O$ were added. Further additions of $NaH_2PO_4.H_2O$ were made prior to and during the induction phase to ensure phosphate was maintained in excess. When the glycerol present at the beginning of fermentation had depleted (approximately 75 $OD_{600}$) a continuous feed of 80% (w/w) glycerol was applied. At the same point in the fermentation an IPTG feed at 170 µM was applied. The start of IPTG feeding was taken as the start of induction. Fermentations were typically run for 64-120 hours at glycerol feed rates (ranging between 0.5 and 2.5 ml/h).

Measurement of Biomass Concentration and Growth Rate.

Biomass concentration was determined by measuring the optical density of cultures at 600 nm.

Periplasmic Extraction.

Cells were collected from culture samples by centrifugation. The supernatant fraction was retained (at −20° C.) for further analysis. The cell pellet fraction was resuspended to the original culture volume in extraction buffer (100 mM Tris-HCl, 10 mM EDTA; pH 7.4). Following incubation at 60° C. for approximately 16 hours the extract was clarified by centrifugation and the supernatant fraction retained (at −20° C.) for analysis.

Fab' Quantification.

Fab' concentrations in periplasmic extracts and culture supernatants were determined by Fab' assembly ELISA as described in Humphreys et al., 2002, Protein Expression and Purification, 26, 309-320 and using Protein G hplc. A HiTrap Protein-G HP 1 ml column (GE-Healthcare or equivalent) was loaded with analyte (approximately neutral pH, 30° C., 0.2 um filtered) at 2 ml/min, the column was washed with 20 mM phosphate, 50 mM NaCl pH 7.4 and then Fab' eluted using an injection of 50 mM Glycine/HCl pH 2.7. Eluted Fab' was measured by A280 on a Agilent 1100 or 1200 HPLC system and quantified by reference to a standard curve of a purified Fab' protein of known concentration.

Figure 3:
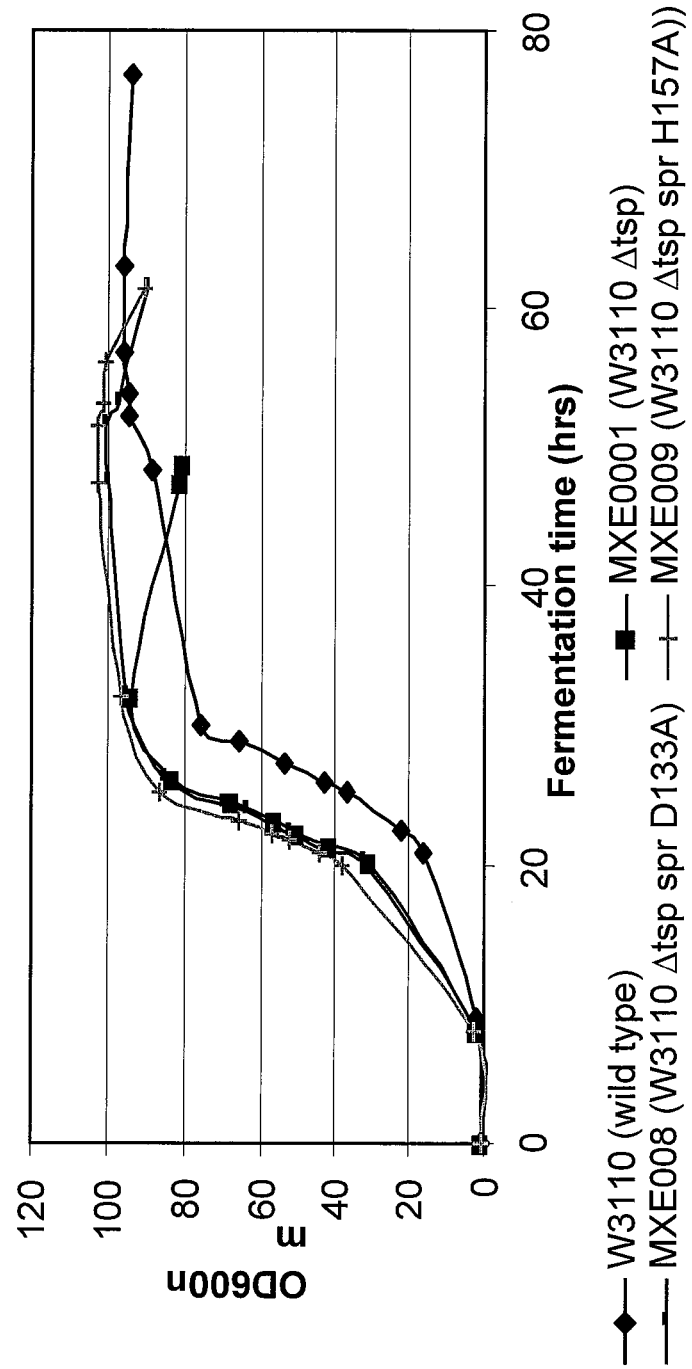
FIG. 3 shows the growth profile of anti-TNFα Fab' expressing strains MXE008 and MXE009 compared to anti-TNFα Fab' expressing strains control W3110 and MXE001.

FIG. 3 shows the growth profile of MXE008 and MXE009 compared to control W3110 and MXE001, which shows that the growth profiles are substantially the same for MXE001, MXE008 and MXE009 over the first ~26 hours and are all higher compared to W3110. After ~26 hours the growth rate for MXE001 drops due to cell lysis. However the spr mutant cell strains MXE008 and MXE009 continue to show a good growth rate and do not lyse after 26 hours.

Figure 4:
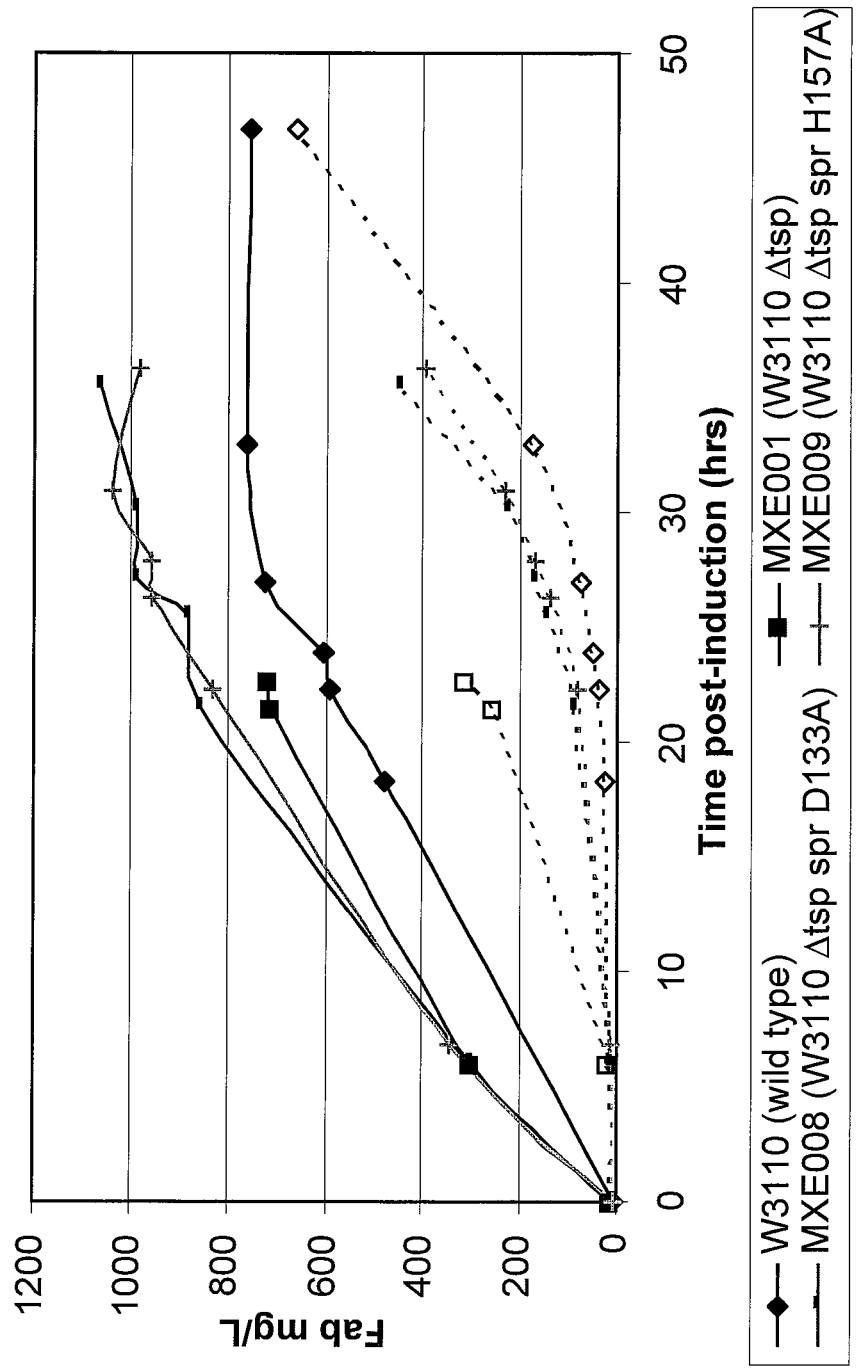
FIG. 4 shows anti-TNFα Fab' yield from the periplasm (shaded symbols) and supernatant (open unshaded symbols) from *E. coli* strains MXE008 and MXE009 compared to control W3110 and MXE001.

FIG. 4 shows total Fab' yield from the periplasm (shaded symbols) and supernatant (open unshaded symbols) from *E. coli* strains MXE008 and MXE009 compared to control W3110 and MXE001. The MXE008 and MXE009 strains show higher periplasmic Fab' expression compared to MXE001 and W3110. Further, MXE001 and also MXE008 and MXE009 show lower supernatant Fab' levels compared to MXE001, which shows reduced cell lysis in MXE008 and MXE009 compared to MXE001.

Figure 7:
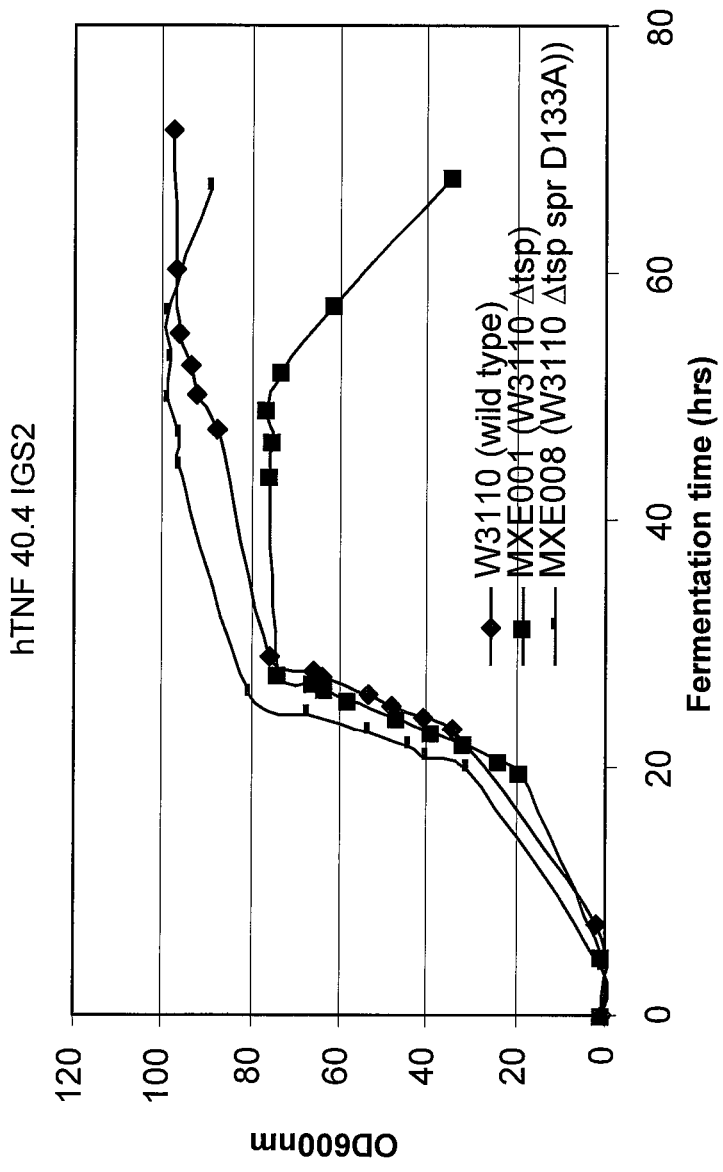
FIG. 7 shows the growth profile of W3110, MXE001 and MXE008 during an anti-TNFα Fab' producing fermentation.

FIG. 7 shows the growth profile of MXE001 and MXE008 during a Fab' producing fermentation. The data illustrates a small increase in initial growth rate of the Δtsp spr mutant strain MXE008 relative to the Δtsp strain MXE001 during biomass accumulation and very significantly increased survival of MXE008 relative to MXE001 strain in the last ~20 hours of the fermentation.

Figure 8:
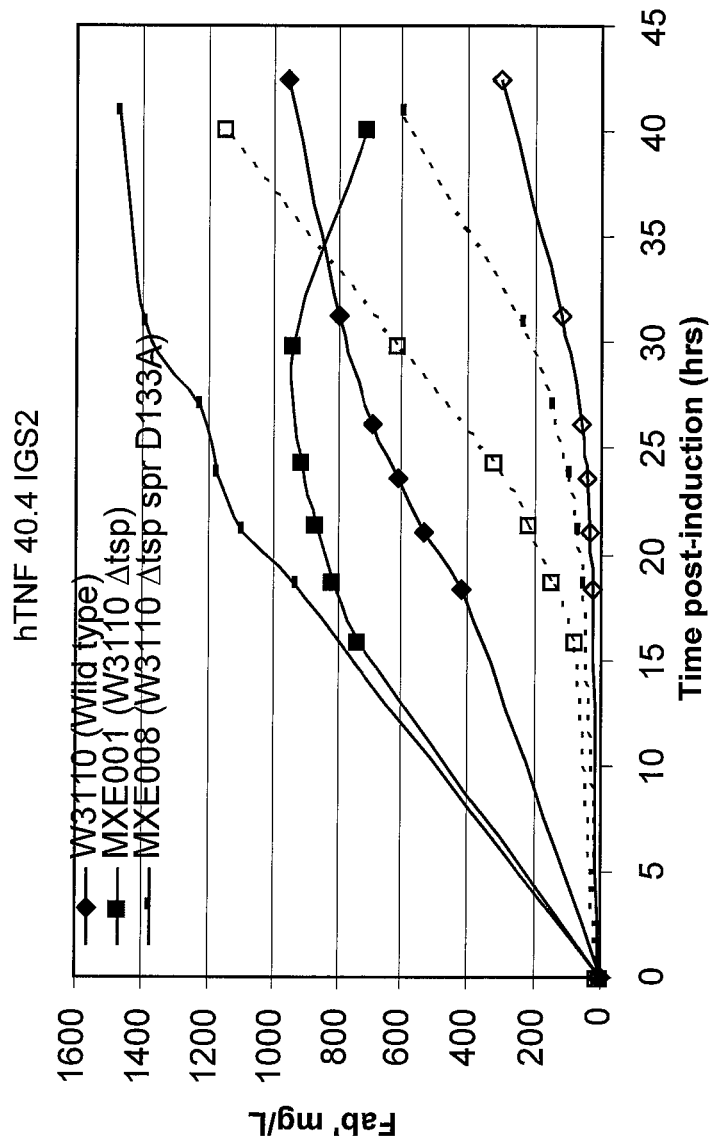
FIG. 8 shows periplasmic anti-TNFα Fab' accumulation (filled lines and symbols) and media anti-TNFα Fab' accumulation (dashed lines and open symbols) for W3110, MXE001 (Δtsp) and MXE008 (Δtsp spr D112A) during an anti-TNFα Fab' producing fermentation.

FIG. 8 shows periplasmic Fab' accumulation (filled lines and symbols) and media Fab' accumulation (dashed lines and open symbols) for W3110, MXE001 (Δtsp) and MXE008 (Δtsp spr D112A) during a Fab' producing fermentation. The data illustrates a small increase in initial periplasmic Fab' accumulation for the MXE008 strain relative to the MXE001 strain which becomes more pronounced during the second half of the Fab' accumulation phase. Addition of the spr mutation in MXE008 to the Δtsp mutation in MXE001 substantially counteracts the 'leaky' phenotype observed with Δtsp MXE001 strains. This improved performance results in a higher periplasmic yield for the MXE008 strain relative to the MXE001 strain and reduced accumulation of Fab' leaked into the culture media for the MXE008 strain relative to the MXE001 strain.

Example 7

Figure 9:
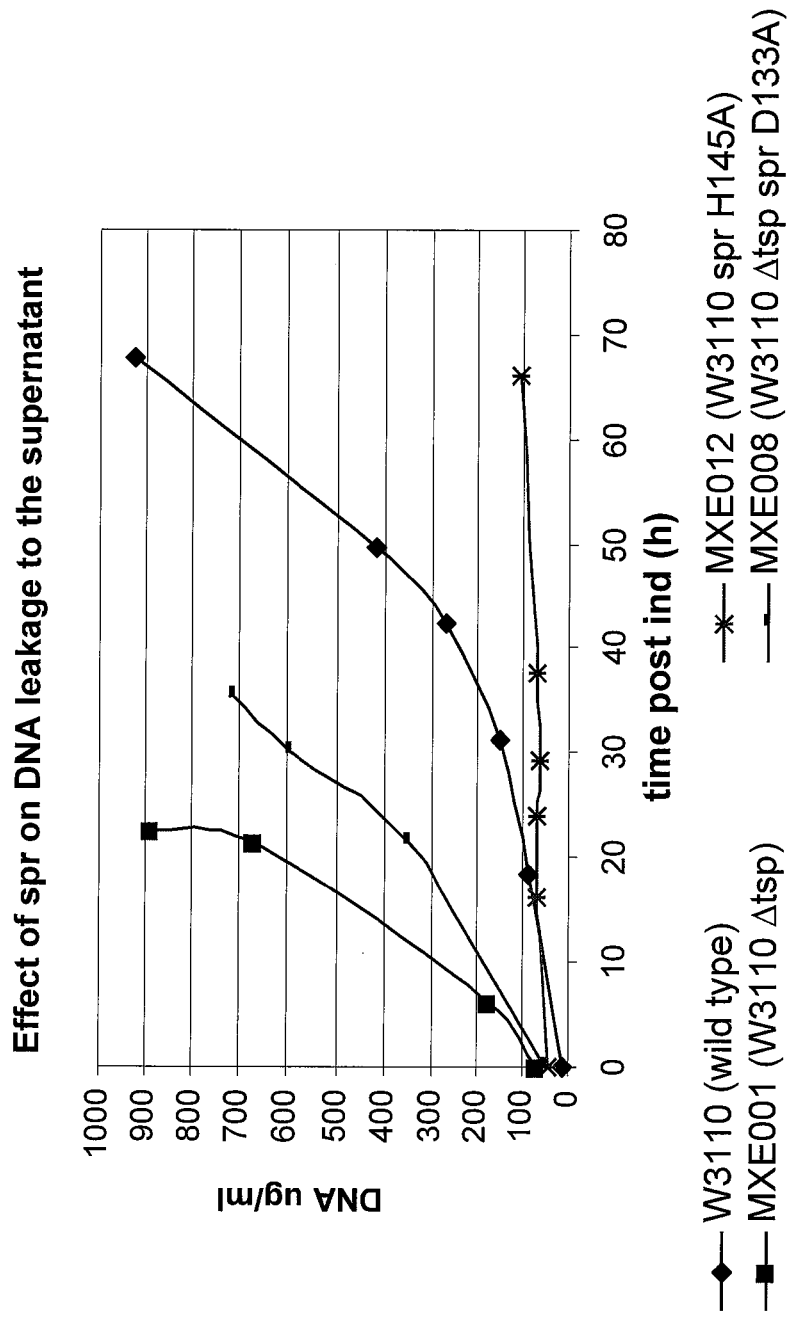
FIG. 9 shows the results of a dsDNA assay of strains W3110, MXE001, MXE008 and MXE012.

Determination of DNA Leakage and Total Protein Quantity in Strains dsDNA Assay The double-stranded DNA leakage into the supernatant of strains W3110, MXE001, MXE008 and MXE012 was determined using the Quant-IT Picogreen dsDNA assay kit (Invitrogen, Ref: P11496). A standard curve was prepared by diluting the DNA standard provided in the range of 1-1000 ng/mL. Samples were diluted in TE buffer, so that the fluorescence reading fell within the linear range of the method (500 to 1000 times). In a 96-well plate, 100 μL of diluted sample or standard were mixed with 100 μL of the Picogreen reagent, and the plate was incubated for 5 minutes at room temperature, protected from light. The fluorescence counts were measured for 0.1 s using a 485 nm excitation filter, and a 535 nm emission filter. The results are shown in FIG. 9.

Figure 10:
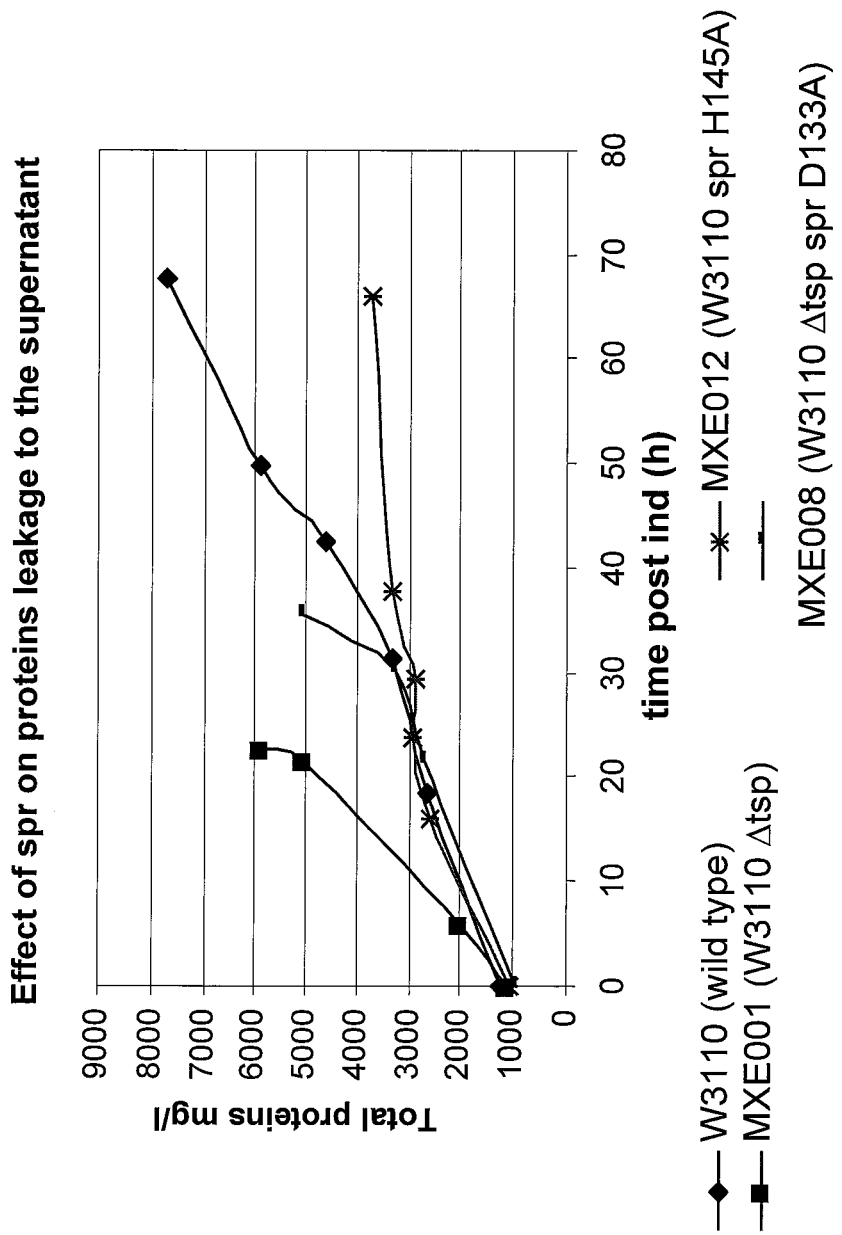
FIG. 10 shows the results of a protein assay of strains W3110, MXE001, MXE008 and MXE012.

Protein Assay:

The total proteins concentration of strains W3110, MXE001, MXE008 and MXE012 was determined using the Coomassie Plus Bradford assay kit (Pierce, Ref: 23236). A standard curve was made by diluting Bovine Serum Albumin standard over a range of 25-1000 μg/mL. Samples were diluted in water so that the optical density fell within the linear range of the method (5 to 10 times), and 33 μL of sample or standard were mixed with 1 mL of Coomassie reagent. After incubating for 10 minutes at room temperature, the $OD_{595nm}$ was read on a spectrophotometer with Coomassie reagent as a blank. The total proteins concentration was calculated based on the standard curve. The results are shown in FIG. 10.

While this invention has been particularly shown and described with reference to preferred embodiments, it will be understood to those skilled in the art that various changes in form and detail may be made without departing from the scope of the invention as defined by the appendant claims.

The invention claimed is:

1. A recombinant gram-negative bacterial cell comprising: a mutant spr gene that encodes a mutant spr protein having a mutation that is an amino acid substitution at one or more amino acids within the spr protein selected from the group consisting of D133, H145, H157, N31, R62, I70, Q73, C94, S95, V98, Q99, R100, L108, Y115, V135, L136, G140, R144, and G147, wherein the wild type spr protein has the sequence of SEQ ID NO: 21, and a mutation in the Tsp gene that encodes a mutated Tsp protein having reduced protease activity or a mutation in the Tsp gene or regulatory sequence of the Tsp gene that reduces or eliminates expression of the Tsp protein, wherein said mutant spr protein reduces lysis of cells containing the mutated Tsp gene.

2. The cell according to claim 1, wherein the mutant spr gene encodes a mutant spr protein having one or more mutations selected from the group consisting of D133A, H145A, H157A, N31Y, R62C, I70T, Q73R, C94A, S95F, V98E, Q99P, R100G, L108S, Y115F, V135D, V135G, L136P, G140C, R144C, and G147C, wherein the wild type spr protein has the sequence of SEQ ID NO: 21.

3. The cell according to claim 2, wherein the mutant spr gene encodes a mutant spr protein having one or more mutations selected from the group consisting of S95F, V98E, Y115F, D133A, V135D, V135G, and G147C, wherein the wild type spr protein has the sequence of SEQ ID NO: 21.

4. The cell according to claim 3, wherein the mutant spr gene encodes a mutant spr protein having the mutations S95F and Y115F, wherein the wild type spr protein has the sequence of SEQ ID NO: 21.

5. The cell according to claim 2, wherein the mutant spr gene encodes a mutant spr protein having a mutation selected from D133A, H145A, and H157A, wherein the wild type spr protein has the sequence of SEQ ID NO: 21.

6. The cell according to claim 1, wherein the cell further comprises one or more of the following mutated genes:
   a) a mutated DegP gene encoding a DegP protein having chaperone activity and reduced protease activity;
   b) a mutated ptr gene, wherein the mutated ptr gene encodes a Protease III protein having reduced protease activity or is a knockout mutated ptr gene; and
   c) a mutated OmpT gene, wherein the mutated OmpT gene encodes a OmpT protein having reduced protease activity or is a knockout mutated OmpT gene.

7. The cell according to claim 1, wherein the mutation in the Tsp gene that eliminates expression of the Tsp protein comprises a knockout mutation of the Tsp gene.

8. The cell according to claim 7, wherein the cell's genome is isogenic to a wild-type bacterial cell except for the mutated spr gene and the mutation in the Tsp gene that encodes a mutated Tsp protein having reduced protease activity or the mutation in the Tsp gene or regulatory sequence of the Tsp gene that reduces or eliminates expression of the Tsp protein.

9. The cell according to claim 1, said cell further comprising a polynucleotide encoding a protein of interest.

10. The cell according to claim 9, wherein the protein of interest is an antibody or an antigen binding fragment thereof.

11. The cell according to claim 10, wherein the antibody or antigen binding fragment thereof is specific for TNF.

12. A recombinant gram-negative bacterial cell comprising:
   a mutant spr gene that encodes a mutant spr protein having a mutation that is an amino acid substitution at one or more amino acids within the spr protein, and
   a mutation in the Tsp gene that encodes a mutated Tsp protein having reduced protease activity or a mutation in the Tsp gene or regulatory sequence of the Tsp gene that reduces or eliminates expression of the Tsp gene, and
   optionally, a polynucleotide encoding a protein of interest,
   wherein the cell's genome is isogenic to a wild-type bacterial cell except for the modification required to reduce Tsp protein activity as compared to the wild-type cell, the mutated spr gene and optionally, the presence of a polynucleotide encoding a protein of interest,
   wherein said mutant spr protein reduces lysis of cells containing the mutated Tsp gene.

13. The cell according to claim 12, wherein the wild-type spr protein has the sequence of SEQ ID NO: 21, and wherein the mutant spr gene encodes a mutant spr protein having:
   a) one or more mutations at one or more amino acids selected from the group consisting of N31Y, R62C, I70T, Q73R, C94A, S95F, V98E, Q99P, R100G, L108S, Y115F, D133A, V135D, V135G, L136P, G140C, R144C, H145A, G147C, H157A, and W174R;

b) one or more mutations at one or more amino acids selected from the group consisting of D133, H145, H157, N31, R62, I70, Q73, C94, S95, V98, Q99, R100, L108, Y115, V135, L136, G140, R144, and G147 and wherein the cell has reduced Tsp protein activity compared to a wild-type cell;

c) one or more mutations at one or more amino acids selected from the group consisting of D133A, H145A, H157A, N31Y, R62C, I70T, Q73R, C94A, S95F, V98E, Q99P, R100G, L108S, Y115F, V135D, V135O, L136P, G140C, R144C, and G147C;

d) one or more mutations at one or more amino acids selected from the group consisting of S95F, V98E, Y115F, D133A, V135D, V135O, and G147C;

e) the mutations S95F and Y115F; or f) a mutation selected from D133A, H145A, and H157A.

14. The cell according to claim 12, wherein the cell has a mutation in the Tsp gene that eliminates expression of the Tsp protein comprising a knockout mutation of the Tsp gene, wherein the knockout mutation comprises a mutation to the Tsp gene start codon and/or one or more stop codons positioned downstream of the Tsp gene start codon and upstream of the Tsp gene stop codon.

15. The cell according to claim 14, wherein the knockout mutation of the Tsp gene comprises a restriction marker site created by a missense mutation to the Tsp gene start codon and optionally one or more further point mutations.

16. The cell according to claim 15, wherein the knockout mutated Tsp gene comprises SEQ ID NO:3.

17. The cell according to claim 12, wherein the cell is *E. coli*.

18. The cell according to claim 12, wherein the cell further comprises a polynucleotide sequence encoding a protein of interest.

19. The cell according to claim 18, wherein the protein of interest is an antibody or an antigen binding fragment thereof.

20. The cell according to claim 19, wherein the antibody or antigen binding fragment thereof is specific for TNF.

21. A recombinant gram-negative bacterial cell comprising:
a mutant spr gene that encodes a mutant spr protein having a mutation that is an amino acid substitution at one or more amino acids within the spr protein, and
a mutation in the Tsp gene that encodes a mutated Tsp protein having reduced protease activity or a mutation in the Tsp gene or regulatory sequence of the Tsp gene that reduces or eliminates expression of the Tsp gene, and
a polynucleotide encoding an antibody or an antigen binding fragment thereof specific for TNF,
wherein said mutant spr protein reduces lysis of cells containing a the mutated Tsp gene.

22. The cell according to claim 21, wherein the cell comprises a mutation in the Tsp gene that reduces or eliminates expression of the Tsp protein, said mutation comprising a knockout mutation of the Tsp gene.

23. A method for producing a protein of interest comprising culturing a recombinant gram-negative bacterial cell as defined in claim 9 in a culture medium under conditions effective to express the recombinant protein of interest and recovering the recombinant protein of interest from the periplasm of the recombinant gram-negative bacterial cell and/or the culture medium.

24. The method according to claim 23, wherein the method further comprises recovering the protein of interest from the cell.

25. The method according to claim 24, wherein the protein of interest is recovered from the periplasm and/or the culture supernatant obtained by separating the cultured recombinant bacterial cell from the culture medium.

26. The method according to claim 23, wherein the protein of interest is an antibody or an antigen binding fragment thereof.

27. The method according to claim 26, wherein the antibody or antigen binding fragment thereof is specific for TNF.

* * * * *

UNITED STATES PATENT AND TRADEMARK OFFICE
CERTIFICATE OF CORRECTION

PATENT NO. : 8,969,039 B2
APPLICATION NO. : 13/522087
DATED : March 3, 2015
INVENTOR(S) : Mark Ellis and David Paul Humphreys It is certified that error appears in the above-identified patent and that said Letters Patent is hereby corrected as shown below:

In the specification

Column 1,
Line 56, "coli-12;" should read --coli K-12;--.

Column 4,
Line 32, "H2CDR" should read --H2 CDR--.

Column 11,
Line 56, "5430;" should read --S430;--.
Line 62, "5430," should read --S430,--.

Column 23,
Line 17, "(31" should read --β1--.

Column 31,
Line 32, "Ase Ito" should read --Ase I to--.

Column 33,
Line 56, "$Tac_i$;" should read --Taq--.

Column 34,
Line 11, "5 end" should read --5' end--.
Line 49, "OD 600" should read --OD600--.

Column 37,
Line 4, "Quantity in Strains dsDNA Assay" should read
--Quantity in Strains
dsDNA assay:--.

Signed and Sealed this
Twenty-second Day of December, 2015

Michelle K. Lee
*Director of the United States Patent and Trademark Office*

In the claims

Column 79,
Line 45, "V1350," should read --V135G,--.
Line 51, "V1350," should read --V135G,--.

Column 80,
Line 66, "V1350," should read --V135G,--.

Column 81,
Line 10, "V1350," should read --V135G,--.
Line 14, "V1350," should read --V135G,--.